United States Patent [19]
Yamashita et al.

[11] Patent Number: 5,883,121
[45] Date of Patent: Mar. 16, 1999

[54] EPOXYSUCCINAMIDE DERIVATIVE OR SALT THEREOF, AND MEDICINE COMPRISING THE SAME

[75] Inventors: Tomohiro Yamashita, Hidaka; Yoshimitsu Suda, Tokorozawa; Yukio Tada, Higashimatsuyama; Nobuhiko Katunuma, Tokushima; Tetsuji Asao, Tokorozawa, all of Japan

[73] Assignee: Taiho Pharmaceutical Co., Ltd., Tokyo, Japan

[21] Appl. No.: 894,050

[22] PCT Filed: Dec. 10, 1996

[86] PCT No.: PCT/JP96/03603

§ 371 Date: Aug. 12, 1997

§ 102(e) Date: Aug. 12, 1997

[87] PCT Pub. No.: WO97/21694

PCT Pub. Date: Jun. 19, 1997

[30] Foreign Application Priority Data

Dec. 12, 1995 [JP] Japan .................................. 7-322971

[51] Int. Cl.$^6$ ....................... A61K 31/335; C07D 303/46
[52] U.S. Cl. ..................... 514/475; 549/548; 549/552; 549/553
[58] Field of Search ................... 549/548, 552, 549/553; 514/475

[56] References Cited

U.S. PATENT DOCUMENTS 5,556,853 9/1996 Tsubotani et al. .................... 514/231.5

*Primary Examiner*—Ba K. Trinh
*Attorney, Agent, or Firm*—Sughrue, Mion, Zinn, Macpeak & Seas, PLLC

[57] ABSTRACT

The invention relates an epoxysuccinamide derivative represented by the general formula (1)

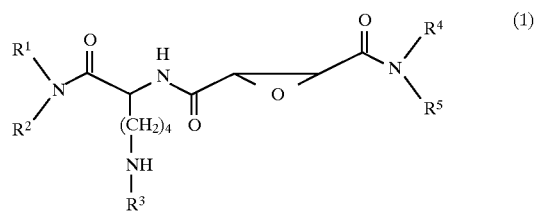

wherein $R^1$ and $R^2$ are the same or different from each other and independently represent H or an aromatic hydrocarbon group or aralkyl group which may be substituted, or $R^1$ and $R^2$ may form a nitrogen-containing heterocyclic ring together with the adjacent nitrogen atoms, $R^3$ is H or an acyl group, $R^4$ is H or an aralkyl group, and $R^5$ is an aromatic hydrocarbon group or aralkyl group which may be substituted, or $R^5$ may form an amino acid residue, which may be protected, together with the adjacent nitrogen atom, or a salt thereof, and a medicine comprising the derivative as an active ingredient; and this compound has an inhibiting activity against cathepsin, and particularly, specifically inhibits cathepsin L and is hence useful for prevention and treatment of osteopathy such as osteoporosis.

10 Claims, 2 Drawing Sheets

EPOXYSUCCINAMIDE DERIVATIVE OR SALT THEREOF, AND MEDICINE COMPRISING THE SAME

This application is a 371 of PCT/JP96/03603 dated Dec. 10, 1996.

TECHNICAL FIELD

The present invention relates to novel epoxysuccinamide derivatives or salts thereof, which exhibit inhibitory activity against cathepsin, and medicines comprising such a derivative or salt.

BACKGROUND ART

On the current trend toward the aging society, abnormal acceleration of bone resorption in a man advanced in years involves many of various senile diseases. In particular, senile osteoporosis is prominent and about to become a great social problem. When the present pharmacotherapy for this senile osteoporosis is viewed, it is conducted to administer (1) estrogen, (2) protein anabolic hormone, (3) calcitonin or (4) vitamin D. However, their effects are found only in improvement of subjective symptom, and hence there is no critical therapy under the circumstances.

On the other hand, it is considered that factors causing osteoporosis include two of calcification and decalcification, and abnormal decomposition of supporting tissue, collagen. However, the development of pharmaceutical agents by paying attention to the abnormal acceleration of collagen decomposition is only now under way. It is reported that this collagen decomposition is involved by a group of cathepsins which are certain kinds of cysteine proteases, and particularly cathepsin L among the group of cathepsins deeply involves the decomposition [FEBS Letters, Vol. 269, No. 1, pp. 189–193 (1990), "Intracellular Proteolysis" (Tokyo Kagaku Dojin)]. It is also proposed to use a cysteine protease inhibitor as a substance, which inhibits decreases of calcium salts and collagen fibers at the same time, in treatment for absorptive osteopathy (Japanese Patent Application Laid-Open Nos. 284127/1988 and 218610/1990). As to compounds which inhibit cathepsin B and cathepsin L, epoxysuccinic acid derivatives are reported in, for example, European Patent Publication No. 655447A1. However, these compounds inhibit cathepsin L and cathepsin B at substantially the same inhibition coefficients, and does not selectively inhibit cathepsin L which is said to involve bone resorption.

It is therefore an object to provide a novel compound which inhibits cathepsin L and family enzymes thereof at a concentration lower than against other cathepsin groups and is useful as an agent for preventing and treating osteopathy such as osteoporosis or hypercalcemia.

DISCLOSURE OF THE INVENTION

In view of the foregoing circumstances, the present inventors have carried out an extensive investigation as to epoxysuccinamide derivatives which specifically inhibit cathepsin L and family enzymes thereof. As a result, the inventors have succeed in inventing compounds satisfying the desired object, thus leading to completion of the present invention.

Namely, the present invention provides an epoxysuccinamide derivative represented by the general formula (1)

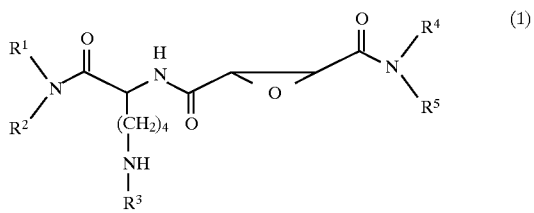

wherein $R^1$ and $R^2$ are the same or different from each other and independently represent a hydrogen atom or an aromatic hydrocarbon group or aralkyl group which may be substituted, or $R^1$ and $R^2$ may form a nitrogen-containing heterocyclic ring together with the adjacent nitrogen atoms, $R^3$ is a hydrogen atom or an acyl group, $R^4$ is a hydrogen atom or an aralkyl group, and $R^5$ is an aromatic hydrocarbon group or aralkyl group which may be substituted, or $R^5$ may form an amino acid residue, which may be protected, together with the adjacent nitrogen atom, or a salt thereof, and a preparation process thereof.

The present invention also provides a medicine comprising the above-described epoxysuccinamide derivative (1) or a salt thereof as an active ingredient.

The present invention further provides a medicinal composition comprising the above-described epoxysuccinamide derivative (1) or a salt thereof and a pharmaceutically acceptable carrier.

The present invention still further provides use of the above-described epoxysuccinamide derivative (1) or a salt thereof for a medicine.

The present invention yet still further provides a method of treating osteopathy, which comprises administering an effective amount of the above-described epoxysuccinamide derivative (1) or a salt thereof to a patient.

The epoxysuccinamide derivative (1) or a salt thereof (the invention compound) has an inhibitory activity against cathepsin L and family enzymes thereof, cathepsin B and cathepsin H. More preferably, the inhibitory effect of the invention compound on cathepsin L and family enzymes thereof is extremely stronger than on other cathepsin groups. Accordingly, the invention compound is useful as a pharmaceutical agent for diseases caused by cathepsins, such as muscular dystrophy, muscular atrophy, myocardial infarction, apoplectic stroke, Alzheimer disease, disturbance of consciousness and dyskinesis upon head injury, multiple sclerosis, peripheral nerve neuropathy, cataract, inflammation, allergy, fulminant hepatitis, osteoporosis, (malignant) hypercalcemia, Paget disease, breast cancer, prostatic cancer, and prostate hypertrophy, or an agent for inhibiting cancerous proliferation and preventing metastasis and a platelet aggregation inhibitor, and especially as an agent for preventing and treating osteopathy such as osteoporosis, malignant hypercalcemia or Paget disease, particularly as an agent for preventing and treating osteoporosis because the invention compound specifically inhibits cathepsin L and family enzymes thereof to inhibit bone resorption.

BEST MODE FOR CARRYING OUT THE INVENTION

Figure 1:
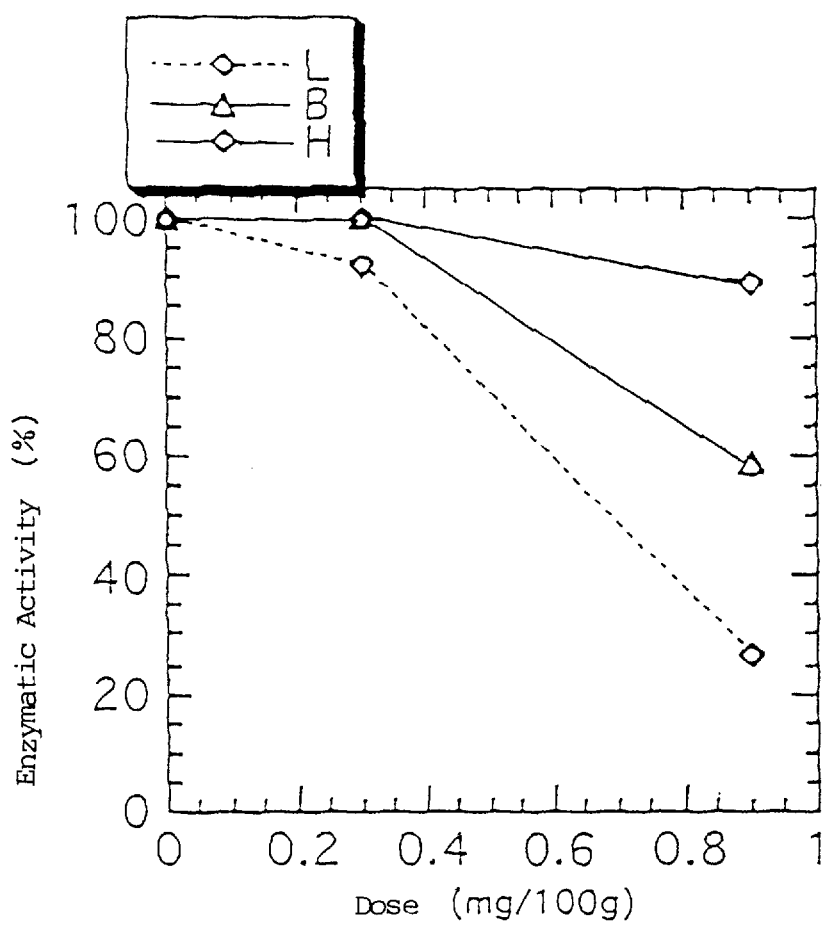
FIG. 1 illustrates an in vivo effect of a compound according to Example 2 on rat hepatic cathepsin.
Figure 2:
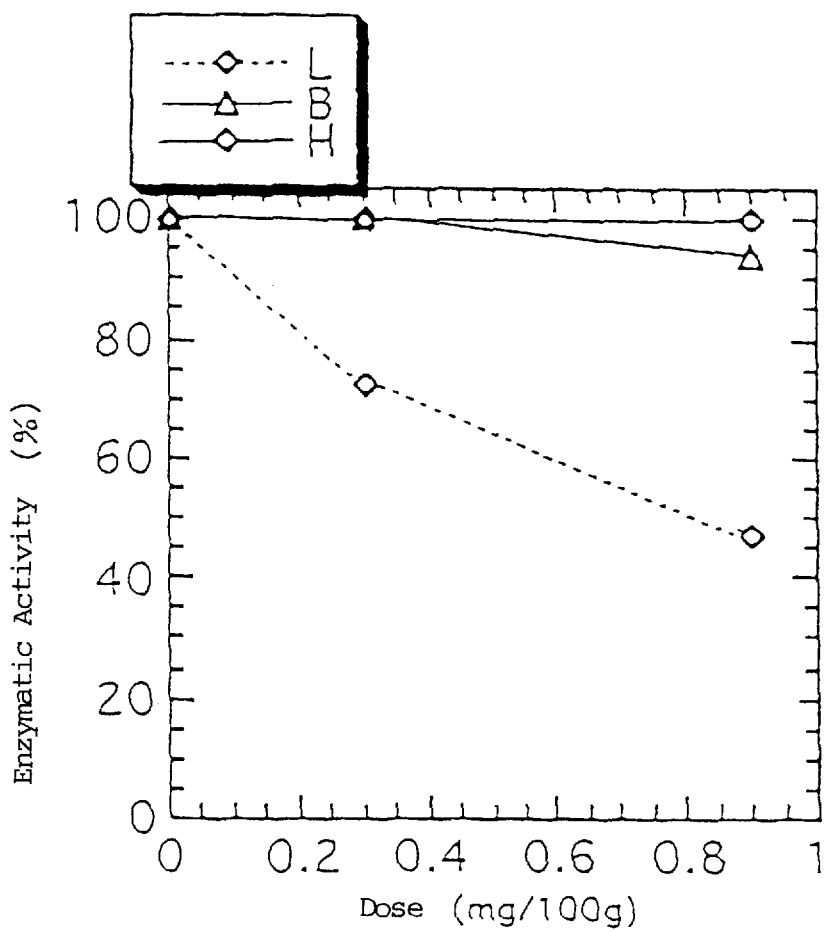
FIG. 2 illustrates an in vivo effect of a compound according to Example 14 on rat hepatic cathepsin.

The aromatic hydrocarbon groups of the aromatic hydrocarbon groups which are represented by $R^1$, $R^2$ and $R^5$ and may be substituted are preferably cyclic aromatic hydrocarbon groups having 6–14 carbon atoms and include, for example, phenyl, naphthyl, dihydronaphthyl, tetrahydronaphthyl, anthryl, pentalenyl, indanyl, indenyl, phenanthryl, azulenyl, acenaphthynyl, acenaphthenyl, indacenyl, biphenylenyl and fluorenyl. These aromatic hydrocarbon groups may have 1–3 substituents selected from an alkyl group (methyl, ethyl, propyl, isopropyl, butyl, pentyl, hexyl or the like) having 1–6 carbon atoms, an alkoxy group (methoxy, ethoxy, propyloxy, isopropyloxy, butoxy, pentyloxy, hexyloxy or the like) having 1–6 carbon atoms, a halogen atom (fluorine, chlorine, bromine or the like), a nitro group or a trifluoromethyl group.

The aralkyl groups represented by $R^1$, $R^2$, $R^4$ and $R^5$ are preferably aralkyl groups having 7–20 carbon atoms and include, for example, benzyl, phenylethyl, phenylpropyl, phenylbutyl, naphthylmethyl, naphthylethyl, anthrylmethyl, 1,2-dihydronaphthyl methyl, 1,2,3,4-tetrahydronaphthyl methyl, 1,2-dihydroanthrylmethyl, 1,2,3,4-tetrahydroanthrylmethyl, 9,10-dihydroanthrylmethyl, diphenylmethyl, diphenylethyl and trityl groups.

$R^1$ and $R^2$ may form a nitrogen-containing heterocyclic ring together with the adjacent nitrogen atom. The nitrogen-containing heterocyclic ring is preferably a 5-, 6- or 7-membered monocyclic or 8-, 9-, 10-, 11- or 12-membered bicyclic heterocyclic group which has a nitrogen atom and may further have an oxygen or sulfur atom. Specific examples thereof include pyrrolidinyl, pyrrolinyl, pyrrolyl, piperazinyl, indolinyl, indolyl, morpholino and piperidino groups. Of these, particularly preferred is the case where $R^1$ and $R^2$ form an indolinyl group together with the adjacent nitrogen atom.

The acyl group represented by $R^3$ is an acyl group, from the synthetic point of view, which generally protects an amino group, or an acyl group which is easily deacylated in vivo. Specific examples thereof include alkanoyl groups (formyl, acetyl, trifluoroacetyl, propionyl, butyryl, isobutyryl, isovaleryl, pivaloyl and heptanoyl groups, etc.) which may be substituted by 1–3 halogen atoms and have 1–7 carbon atoms; benzoyl groups (benzoyl, 4-chlorobenzoyl, 4-nitrobenzoyl, 4-bromobenzoyl and 4-methoxybenzoyl groups, etc.) which may have 1–3 substituents selected from an alkyl group (methyl, ethyl, propyl, isopropyl, butyl, pentyl, hexyl or the like) having 1–6 carbon atoms, an alkoxy group (methoxy, ethoxy, propyloxy, isopropyloxy, butoxy, pentyloxy, hexyloxy or the like) having 1–6 carbon atoms, a halogen atom (fluorine, chlorine, bromine or the like), a nitro group, an amino group or an acylamino group (acetylamino, benzoylamino or the like); benzyloxycarbonyl groups (benzyloxycarbonyl, 4-chlorobenzyloxycarbonyl, 4-nitrobenzyloxycarbonyl, 4-bromobenzyloxycarbonyl and 4-methoxybenzyloxycarbonyl groups, etc.) which may have 1–3 substituents selected from an alkyl group (methyl, ethyl, propyl, isopropyl, butyl, pentyl, hexyl or the like) having 1–6 carbon atoms, an alkoxy group (methoxy, ethoxy, propyloxy, isopropyloxy, butoxy, pentyloxy, hexyloxy or the like) having 1–6 carbon atoms, a halogen atom (fluorine, chlorine, bromine or the like), a nitro group, an amino group or an acylamino group (acetylamino, benzoylamino or the like); and alkoxycarbonyl groups (methoxycarbonyl, ethoxycarbonyl and t-butoxycarbonyl groups, etc.) having 2–7 carbon atoms. Of these, a hydrogen atom, an alkanoyl group having 1–7 carbon atoms, a benzoyl group, an alkoxycarbonyl group having 2–7 carbon atoms or a benzyloxycarbonyl group is more preferred as $R^3$, with a hydrogen atom being particularly preferred.

The amino acid residue which is formed by $R^5$ together with the nitrogen atom adjacent to the carbonyl is such that the amino group of the amino acid residue corresponds to the nitrogen atom adjacent to the carbonyl. Such an amino acid is a naturally occurring or synthetic compound having at least an amino group and a carboxyl group, which may be protected, in its molecule, and includes amino acids having 2–20 carbon atoms. The naturally occurring amino acids include constituent amino acids for proteins in organisms, for example, alanine, isoleucine, norleucine, glycine, serine, threonine, valine, leucine, arginine, hydroxylysine, lysine, asparagin, aspartic acid, glutamine, glutamic acid, cystine, cysteine, methionine, phenylalanine, triptophan, histidine, hydroxyproline, proline and tyrosine. Examples of other naturally occurring amino acids and synthetic amino acids, which are not constituent amino acids for vital proteins, but play an important role in the vital body, include amino acids such as sarcosine, creatine, homocysteine, cysteine sulfonic acid, norleucine, isoserine, homoserine, oxylysine, norvaline, dehydrovaline, ornithine, arginosuccinic acid, dopa, 3-monoiodotyrosine, 3,5-diiodotyrosine, thyroxine, α,γ-diaminobutyric acid, 2,3-diaminosuccinic acid, α-aminoadipic acid, α,β-diaminopropionic acid, sacchropine, β-alanine, γ-aminobutyric acid, β-aminobutyric acid, ε-aminocaproic acid, acediasulfone, agaristine, alanosine, hadacidin, melphalan and ibotenic acid.

Of these, the naturally occurring amino acids are more preferred, with phenylalanine being particularly preferred.

The carboxyl group of the amino acid residue may be protected by an amino group which may have 1 or 2 substituents such as alkyl groups (methyl, ethyl, propyl, isopropyl, butyl, isobutyl, pentyl, hexyl, etc.) having 1–6 carbon atoms, alkenyl groups (ethenyl, propenyl, butenyl, pentenyl, hexenyl, etc.) having 2–6 carbon atoms, alkynyl groups (ethynyl, propynyl, butynyl, pentynyl, hexynyl, etc.) having 2–6 carbon atoms, cycloalkyl groups (cyclopropyl, cyclobutyl, cyclopentyl, cyclohexyl, etc.) having 3–6 carbon atoms, cycloalkenyl groups (cyclobutenyl, cyclopentenyl, cyclohexenyl, etc.) having 3–6 carbon atoms, hydroxyalkyl groups (hydroxymethyl, hydroxyethyl, hydroxypropyl, hydroxybutyl, etc.) having 1–6 carbon atoms, aromatic hydrocarbon groups (phenyl, naphthyl, anthranyl, etc.) which may be substituted, or aralkyl groups (benzyl, phenylethyl, phenylpropyl, diphenylmethyl, diphenylethyl, naphthylmethyl, naphthylethyl, trityl, etc.) having 7–20 carbon atoms. Preferred substituents of the amino group which protects the carboxyl group of the amino acid residue are one or two of the alkyl groups having 1–6 carbon atoms, the cycloalkyl group having 3–6 carbon atoms, the aromatic hydrocarbon groups which may be substituted, and the aralkyl groups having 7–20 carbon atoms. Methyl, ethyl, propyl, isopropyl, cyclohexyl, phenyl and phenylethyl groups are particularly preferred. Particularly preferred amino acid residues include a phenylalanine residue and phenylalanine residues the carboxyl groups of which have been protected by the above-described amino group which may have the substituents.

The epoxysuccinamide derivative according to the present invention can form a pharmaceutically acceptable salt. As specific examples thereof, an alkali or alkaline earth metal salt such as the lithium salt, sodium salt, potassium salt, magnesium salt, calcium salt; or an ammonium salt such as the ammonium salt, methylammonium salt, dimethylammonium salt, trimethylammonium salt may be formed when, for example, an acid group is present. When a basic group is present, a mineral acid salt such as the hydrochloride, hydrobromide, sulfate, nitrate, phosphate; or an organic acid salt such as the acetate, propionate, tartarate, fumarate, maleate, malate, citrate, methanesulfonate, p-toluenesulfonate may be formed. The epoxysuccinamide derivative or the salt thereof according to the present invention may be present in the form of a solvate typified by a hydrate.

With respect to the stereochemistry as to the epoxy moiety of the epoxysuccinamide derivative according to the present invention represented by the general formula (1), four configurations of (R,R), (S,R), (R,S) and (S,S) can be taken depending on the configuration of epoxysuccinic acid used as a starting material. The present invention include all of these stereoisomers. With respect to asymmetric carbon atoms other than the above, both R and S are included.

In the invention compounds, more preferred are compounds in which $R^1$ and $R^2$ are independently a hydrogen atom; a phenyl, naphthyl, indanyl, indolinyl or fluorenyl group which may be substituted; a benzyl group; a phenylethyl group; or a diphenylethyl or phenylpropyl group; $R^4$ and $R^5$ are independently a hydrogen atom; a phenyl, naphthyl, indanyl or fluorenyl group which may be substituted; a benzyl group; a phenylethyl group; a diphenylethyl group; a phenylpropyl group; or a residue of a naturally occurring amino acid having 2–20 carbon atoms, the carboxyl group of the amino acid residue may being protected by an amino group which may have 1 or 2 substituents such as alkyl groups having 1–6 carbon atoms, cycloalkyl groups having 3–6 carbon atoms, aromatic hydrocarbon groups which may be substituted, or aralkyl groups having 7–20 carbon atoms. Further preferred compounds are the following compound groups:

(a) compounds in which $R^1$ is a hydrogen atom; and $R^2$ is a phenyl or naphthyl group which may be substituted;

(b) compounds in which $R^4$ is a hydrogen atom; and $R^5$ is a naphthyl group which may be substituted; and (c) compounds in which the amino acid residue of $R^5$ is a phenylalanine residue or a phenylalanine residue the carboxyl group of which has been protected by an amino group (protecting group: amino, methylamino, dimethylamino, ethylamino, propylamino, isopropylamino, cyclohexylamino, benzylamino, phenylethylamino or phenylamino).

Most preferred compounds include the following compounds (1) to (25).

(1) Nα-[L-3-trans-(2-phenylethylcarbamoyl)oxirane-2-carbonyl]-L-lysine-1-naphthylamide (Example 2).
(2) Nα-[L-3-trans-(2-indanylcarbamoyl)oxirane-2-carbonyl]-L-lysine-1-naphthylamide (Example 12).
(3) Nα-{L-3-trans-[(S)-1-carbamoyl-2-phenylethylcarbamoyl]oxirane-2-carbonyl}-L-lysine-1-naphthylamide (Example 14).
(4) Nα-{L-3-trans-[(S)-1-carbamoyl-2-phenylethylcarbamoyl]oxirane-2-carbonyl}-L-lysine dibenzylamide (Example 16).
(5) Nα-{L-3-trans-[(S)-1-(2-phenylethylcarbamoyl)-2-phenylethylcarbamoyl]oxirane-2-carbonyl}-L-lysine-1-naphthylamide (Example 24).
(6) Nα-{L-3-trans-[(S)-1-benzylcarbamoyl-2-phenylethylcarbamoyl]oxirane-2-carbonyl}-L-lysine-1-naphthylamide (Example 26).
(7) Nα-[L-3-trans-(1-naphthylcarbamoyl)oxirane-2-carbonyl]-L-lysine-1-naphthylamide (Example 30).
(8) Nα-{L-3-trans-[(S)-1-(2-phenylethylcarbamoyl)-2-phenylethylcarbamoyl]oxirane-2-carbonyl}-Nε-acetyl-L-lysine-1-naphthylamide (Example 32).
(9) Nα-{L-3-trans-[(S)-1-(2-phenylethylcarbamoyl)-2-phenylethylcarbamoyl]oxirane-2-carbonyl}-Nε-propanoyl-L-lysine-1-naphthylamide (Example 33).
(10) Nα-{L-3-trans-[(S)-1-(2-phenylethylcarbamoyl)-2-phenylethylcarbamoyl]oxirane-2-carbonyl}-L-lysine anilide (Example 35).
(11) Nα-{L-3-trans-[(S)-1-carbamoyl-2-phenylethylcarbamoyl]oxirane-2-carbonyl}-L-lysine-2-methoxyanilide (Example 37).
(12) Nα-{L-3-trans-[(S)-1-(2-phenylethylcarbamoyl)-2-phenylethylcarbamoyl]oxirane-2-carbonyl}-L-lysine-2-methoxyanilide (Example 39).
(13) Nα-{L-3-trans-[(S)-1-(2-phenylethylcarbamoyl)-2-phenylethylcarbamoyl]oxirane-2-carbonyl}-L-lysine-2-trifluoromethylanilide (Example 43).
(14) Nα-{L-3-trans-[(S)-1-(2-phenylethylcarbamoyl)-2-phenylethylcarbamoyl]oxirane-2-carbonyl}-L-lysine indolinylamide (Example 47).
(15) Nα-{L-3-trans-[(S)-1-carbamoyl-2-phenylethylcarbamoyl]oxirane-2-carbonyl}-L-lysine-1-(4-chloronaphthyl)amide (Example 48).
(16) Nα-{L-3-trans-[(S)-1-propylcarbamoyl-2-phenylethylcarbamoyl]oxirane-2-carbonyl}-L-lysine-1-naphthylamide (Example 51).
(17) Nα-{L-3-trans-[(R)-1-(2-phenylethylcarbamoyl)-2-phenylethylcarbamoyl]oxirane-2-carbonyl}-L-lysine-1-naphthylamide (Example 53).
(18) Nα-{L-3-trans-[(S)-1-carbamoyl-2-phenylethylcarbamoyl]oxirane-2-carbonyl}-L-lysine anilide (Example 55).
(19) Nα-{L-3-trans-[(S)-1-phenylcarbamoyl-2-phenylethylcarbamoyl]oxirane-2-carbonyl}-L-lysine-1-naphthylamide (Example 57).
(20) Nα-{L-3-trans-[(S)-1-propylcarbamoyl-2-phenylethylcarbamoyl]oxirane-2-carbonyl}-L-lysine anilide (Example 59).
(21) Nα-{L-3-trans-[(S)-1-isopropylcarbamoyl-2-phenylethylcarbamoyl]oxirane-2-carbonyl}-L-lysine anilide (Example 61).
(22) Nα-{L-3-trans-[(S)-1-methylcarbamoyl-2-phenylethylcarbamoyl]oxirane-2-carbonyl}-L-lysine anilide (Example 63).
(23) Nα-{L-3-trans-[(S)-1-dimethylcarbamoyl-2-phenylethylcarbamoyl]oxirane-2-carbonyl}-L-lysine anilide (Example 65).
(24) Nα-{L-3-trans-[(S)-1-ethylcarbamoyl-2-phenylethylcarbamoyl]oxirane-2-carbonyl}-L-lysine anilide (Example 67).
(25) Nα-{L-3-trans-[(S)-1-cyclohexylcarbamoyl-2-phenylethylcarbamoyl]oxirane-2-carbonyl}-L-lysine anilide (Example 69).

The epoxysuccinamide derivatives according to the present invention can be synthesized in accordance with, for example, the following process.

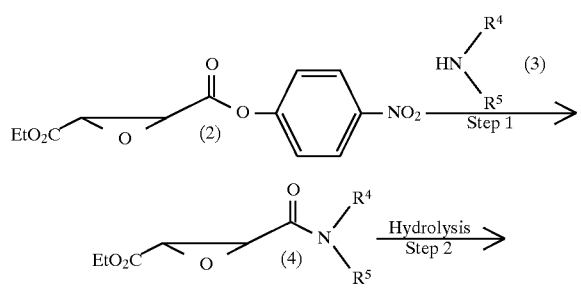

-continued

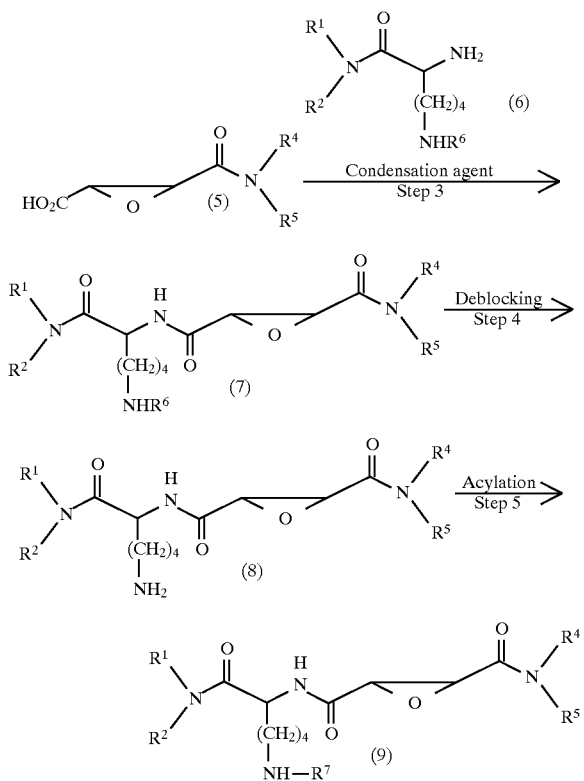

wherein in the individual general formulae, $R^1$, $R^2$, $R^4$ and $R^5$ have the same meanings as defined above, $R^6$ is an acyl group, and specifically is a t-butoxycarbonyl, benzyloxycarbonyl, fluorenylmethylcarbonyl or phthalimide group, and $R^7$ represents the same acyl group as exemplified in $R^3$.

The individual steps will hereinafter be described.

<Step 1>

A compound (2) easily obtained in accordance with the process already known from a literature (Chemical and Pharmaceutical Bulletin, Vol. 35, p. 1098, 1987) is reacted with a compound represented by the general formula (3) in a proper solvent, thereby obtaining an amide derivative represented by the general formula (4). No particular limitation is imposed on the proper solvent so far as it does not affect the reaction. Examples thereof include dichloromethane, chloroform, ethyl acetate, tetrahydrofuran, dioxane, diethyl ether, isopropyl ether, benzene, toluene, N,N-dimethylformamide and dimethyl sulfoxide. These solvents may be used either singly or in any combination thereof. Most of the compounds represented by the general formula (3) are known, and novel compounds may also be synthesized in accordance with methods known per se in the art.

<Step 2>

The amide derivative (4) obtained in the step 1 is hydrolyzed, thereby obtaining a carboxylic acid represented by the general formula (5). As a reaction reagent, an inorganic base is used. Preferable examples thereof include lithium hydroxide, sodium hydroxide, potassium hydroxide, calcium hydroxide, barium hydroxide, lithium carbonate, sodium carbonate and potassium carbonate. No particular limitation is imposed on a solvent used so far as it does not affect the reaction. Examples thereof include tetrahydrofuran, dioxane, diethyl ether, isopropyl ether, benzene, toluene, N,N-dimethylformamide, dimethyl sulfoxide, methanol, ethanol, n-propanol, 2-propanol and water. These solvents may be used either singly or in any combination thereof.

<Step 3>

The carboxylic acid (5) obtained in the step 2 is reacted with an amine represented by the general formula (6) in the presence of a condensation agent in a proper solvent, thereby obtaining a condensate represented by the general formula (7). Examples of a solvent used in the reaction include dichloromethane, chloroform, ethyl acetate, tetrahydrofuran, dioxane, diethyl ether, benzene, toluene, N,N-dimethylformamide and dimethyl sulfoxide. These solvents may be used either singly or in any combination thereof. The condensation agent means a general condensation agent used in organic synthetic reactions. Examples thereof include N,N-dicyclohexylcarbodiimide, 1-ethyl-3-(3-dimethylaminopropyl)carbodiimide hydrochloride, 1,1-carbonyldiimidazole, 2-chloro-1,3-dimethylimidazolinium chloride, pivaloyl chloride, thionyl chloride and trifluoroacetic anhydride.

The compound (6) used in the step 3 is synthesized in the following manner.

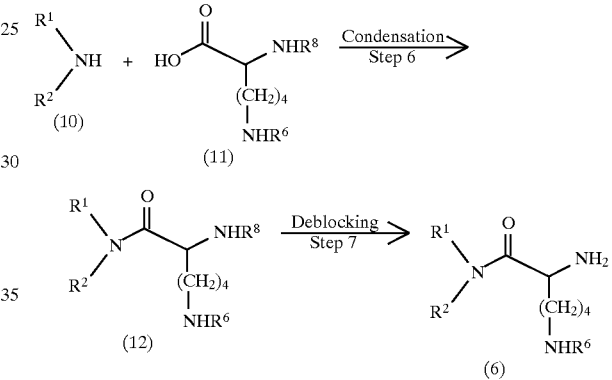

wherein $R^1$, $R^2$ and $R^6$ have the same meanings as defined above, and $R^8$ is a protecting group for the amino group and may be separated without affecting $R^6$. Examples thereof include benzyloxycarbonyl, fluorenylmethyloxycarbonyl and t-butoxycarbonyl groups.

<Step 6>

An amine compound represented by the general formula (10) is reacted with protected lysine represented by the general formula (11) in the presence of a condensation agent in a solvent, thereby synthesizing a condensate represented by the general formula (12). The solvent used in this reaction may be any solvent without particular limitations so far as it does not affect the reaction. Examples thereof include dichloromethane, chloroform, ethyl acetate, tetrahydrofuran, dioxane, diethyl ether, isopropyl ether, benzene, toluene, N,N-dimethylformamide and dimethyl sulfoxide. These solvents may be used either singly or in any combination thereof. The condensation agent means a general condensation agent used in organic synthetic reactions. For examples, N,N-dicyclohexylcarbodiimide, 1-ethyl-3-(3-dimethylaminopropyl)carbodiimide hydrochloride, 1,1-carbonyldiimidazole, 2-chloro-1,3-dimethylimidazolinium chloride, pivaloyl chloride, thionyl chloride and trifluoroacetic anhydride may be used.

<Step 7>

When the amino-protecting group $R^8$ is separated from the condensate (12) obtained in the step 6, the amine represented by the general formula (6) is obtained. The reaction conditions depend on $R^8$. When $R^8$ is a t-butoxycarbonyl group, the reaction can be carried out by treating the condensate with a dilute acid in a proper solvent. No particular limitation is imposed on the proper solvent so far as it does not affect the reaction. Examples thereof include dichloromethane, chloroform, ethyl acetate, tetrahydrofuran, dioxane, diethyl ether, isopropyl ether, benzene, toluene, N,N-dimethylformamide and dimethyl sulfoxide. These solvents may be used either singly or in any combination thereof. Examples of the acid include mineral acids such as hydrochloric acid, hydrobromic acid, sulfuric acid and nitric acid, and organic acids such as trifluoroacetic acid, p-toluenesulfonic acid and methanesulfonic acid.

When $R^8$ is a benzyloxycarbonyl group, the object can be achieved by catalytic hydrogenation. Examples of a catalyst used in the catalytic hydrogenation include palladium on carbon, palladium on alumina, palladium black, platinum on carbon, platinum oxide, platinum on alumina and platinum black. The amount of the catalyst used is desirably within a range of from 10% to 200% of the weight of the substrate. Examples of a solvent used include methanol, ethanol, water, acetic acid, tetrahydrofuran, dioxane, diethyl ether, diisopropyl ether, ethyl acetate, dichloromethane and chloroform. These solvents may be used either singly or in any combination thereof.

When $R^8$ is a fluorenylmethyloxycarbonyl group, the condensate is treated with a basic compound in a proper solvent, whereby the intended amine compound can be derived. No particular limitation is imposed on the solvent so far as it does not affect the reaction. Examples thereof include dichloromethane, chloroform, ethyl acetate, tetrahydrofuran, dioxane, diethyl ether, isopropyl ether, benzene, toluene, N,N-dimethylformamide and dimethyl sulfoxide. These solvents may be used either singly or in any combination thereof. The basic compound is desirably an organic amine. Examples thereof include diethylamine, triethylamine, piperidine, pyrrolidine, diisopropylethylamine, N,N-dimethylaminopyridine and 1,8-diazabicyclo[5,4,0]-7-undecene.

<Step 4>

The condensate (7) obtained in the step 3 can be optionally subjected to deblocking, thereby converting it into a compound represented by the general formula (8). As the conditions for the deblocking, the process as described in the step 7 may be used.

<Step 5>

Into the compound (8) obtained in the step 4 can be introduced an acyl group represented by $R^7$ as needed. More specifically, the compound (8) is reacted with an acid anhydride such as acetic anhydride, propionic anhydride, trifluoroacetic anhydride or benzoic anhydride, or an acid chloride such as acetyl chloride, propionyl chloride, trifluoroacetyl chloride or benzoyl chloride in the presence of a basic compound in a proper solvent, or reacted with a fatty acid having 1–7 carbon atoms, such as formic acid, acetic acid, propionic acid, butyric acid, isobutyric acid, isovaleric acid, pivalic acid or heptanoic acid, or unsubstituted or substituted benzoic acid such as benzoic acid, 4-nitrobenzoic acid or 4-methoxybenzoic acid in the presence of a condensation agent, whereby the acyl group represented by $R^7$ can be introduced.

As the condensation agent, any of those mentioned in the step 3 may be used. No particular limitation is imposed on the solvent so far as it does not affect the reaction. Examples thereof include dichloromethane, chloroform, ethyl acetate, tetrahydrofuran, dioxane, diethyl ether, isopropyl ether, benzene, toluene, N,N-dimethylformamide and dimethyl sulfoxide. The basic compound is desirably an organic amine. Examples thereof include triethylamine, pyridine, N,N-dimethylaminopyridine, diisopropylethylamine and 1,8-diazabicyclo[5,4,0]-7-undecene.

The intermediates for preparation and invention compound thus obtained can be purified in accordance with separating means generally used in synthetic chemistry, such as recrystallization, distillation and column chromatography.

As apparent from the pharmacological test, which will be described subsequently, the invention compounds have an inhibitory activity against cathepsin L and family enzymes thereof, cathepsin B and cathepsin H. More preferably, $IC_{50}$ (50% inhibitory concentration) of the invention compounds against cathepsin L is about $1/100$ to $1/200,000$ of its $IC_{50}$ against cathepsin B, so that the inhibitory selectivity of the invention compounds is specific for cathepsin L and family enzymes thereof. Accordingly, the invention compounds are useful as pharmaceutical agents for diseases caused by cathepsins, such as muscular dystrophy, muscular atrophy, myocardial infarction, apoplectic stroke, Alzheimer disease, disturbance of consciousness and dyskinesis upon head injury, multiple sclerosis, peripheral nerve neuropathy, cataract, inflammation, allergy, fulminant hepatitis, osteoporosis, (malignant) hypercalcemia, Paget disease, breast cancer, prostatic cancer, and prostatic hypertrophy, or agents for inhibiting cancerous proliferation and preventing metastasis and platelet aggregation inhibitors. Especially, the invention compounds are useful as agents for preventing and treating osteopathy such as osteoporosis, malignant hypercalcemia or Paget disease because they specifically inhibits cathepsin L and family enzymes thereof to inhibit bone resorption.

When the invention compound or the salt thereof is used in the prevention and treatment of the above-described diseases, including osteoporosis, of mammals including the human, it is orally or parenterally administered. The dose thereof varies depending on the age, sex, weight and condition of a patient to be administered. However, when the invention compound is administered to an adult patient 50 kg in weight, it is orally or parenterally administered in the range of generally from about 0.1 mg to 1,000 mg, preferably from about 1 mg to 1,000 mg, more preferably from about 5 mg to 500 mg, per day in terms of an active ingredient. Meanwhile, the administration may be divided into 2–3 times per day, or may be once per day.

The invention compound can be orally or parenterally administered in the form of a solid preparation such as tablets, capsules, granules or powder, or a liquid preparation such as syrup or injection by blending an effective amount of the invention compound with a pharmaceutically acceptable carriers. As the pharmaceutically acceptable carriers, there may be used various kinds of organic or inorganic carriers commonly used as preparation materials. They are incorporated as excipients, lubricants, binders and disintegrators for solid preparations, or as solvents, solubilizing agents, suspending agents, isotonicity agents, buffers and analgesics for liquid preparations. Additives for preparations, such as antiseptics, antioxidants, colorants and sweetners may also be used as needed.

Suitable examples of the excipient include lactose, D-mannitol, starch, crystalline cellulose and precipitated anhydrous silicic acid. Suitable examples of the lubricants include magnesium stearate, calcium stearate, talc and colloidal silica. Suitable examples of the binders include crystalline cellulose, sucrose, D-mannitol, dextrin, hydroxypropyl cellulose, hydroxypropylmethyl cellulose and polyvinyl pyrrolidone. Suitable examples of the disintegrators include starch, carboxymethyl cellulose, calcium carboxymethyl cellulose, sodium crosscalmelol and sodium carboxymethyl starch. Suitable examples of the solvents include water for injections, alcohol, propylene glycol, macrogol, sesame oil and corn oil. Suitable examples of the solubilizers include polyethylene glycol, propylene glycol, D-mannitol, benzyl benzoate, ethanol, trisaminomethane, cholesterol, triethanolamine, sodium carbonate and sodium citrate. Suitable examples of the suspending agents include surfactants such as triethanolamine stearate, sodium lauryl sulfate, laurylaminopropionic acid, lecithin, benzalkonium chloride, benzethonium chloride and glycerol monostearate, and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Suitable examples of the buffers include phosphates, acetates, carbonates and citrates. Suitable examples of the analgesics include benzyl alcohol. Suitable examples of the antiseptics include p-hydroxybenzoic acid esters, chlorobutanol, benzyl alcohol, phenethyl alcohol, dehydroacetic acids and sorbic acid. Suitable examples of the antioxidants include sulfites and ascorbates.

EXAMPLES

The present invention will hereinafter be described in detail by the following Examples. However, the present invention is not limited to these Examples.

Preparation Example 1

Ethyl L-3-trans-(2-phenylethylcarbamoyl)oxirane-2-carboxylate

An ethyl acetate solution (7 ml) of 3.45 g (28.51 mmol) of 2-phenylethylamine was added dropwise to an ethyl acetate solution (50 ml) of 8.0 g (28.47 mmol) of ethyl 4-nitrophenyl L-trans-epoxysuccinate under cooling with ice water. After completion of the addition, the mixture was stirred at room temperature for 5 hours. The reaction mixture was washed with a 2% solution of sodium hydroxide until the yellow color of an organic layer vanished, and further washed with 1N hydrochloric acid and saturated saline. After the organic layer was dried over magnesium sulfate and filtered, the solvent was distilled off under reduced pressure. The thus-obtained crude product was recrystallized from hexane-ethyl acetate to obtain 5 g of the title compound.

m.p.: 102°–103° C.

$^1$H-NMR (CDCl$_3$) δ: 7.40–7.15(5H,m), 4.25(2H,dq,J=7.8,2.0 Hz), 3.64(1H,d,J=2.0 Hz), 3.53(2H,m), 3.23(1H,d, J=2.0 Hz), 2.82(2H,dt,J=6.8,3.6 Hz), 1.30(3H,t,J=7.2 Hz).

Mass: FAB(+) m/e 264 (MH)$^+$ FAB(-) m/e 262 (M-H)$^-$.

Preparation Example 2

L-3-trans-(2-Phenylethylcarbamoyl)oxirane-2-carboxylic acid

A 50% aqueous ethanol solution (50 ml) of 1.32 g (20.0 mmol) of 85% potassium hydroxide was added dropwise to an ethanol solution (50 ml) of 5 g (19.02 mmol) of the compound obtained in Preparation Example 1. After completion of the addition, the mixture was stirred at room temperature for 1 hour. The reaction mixture was concentrated under reduced pressure, and each 30 ml of water and ethyl acetate were added to the residue to conduct extraction. After an aqueous layer was acidified with 6N hydrochloric acid, the extraction was conducted again with ethyl acetate, and an organic layer was washed with saturated brine. After the organic layer was dried over magnesium sulfate and filtered, the solvent was distilled off under reduced pressure to obtain 3.34 g of the title compound.

$^1$H-NMR (CDCl$_3$) δ: 7.87–7.15(5H,m), 6.28(1H,t,J=6.0 Hz), 3.70(1H,d,J=2.0 Hz), 3.54(2H,m), 3.35(1H,d,J=2.0 Hz), 2.28(2H,m).

Mass: FAB(-) m/e 234 (M-H)$^-$.

Preparation Example 3

Ethyl L-3-trans-(2-indanylcarbamoyl)oxirane-2-carboxylate

Following a process similar to the process of Preparation Example 1, 595 mg of the title compound were obtained from 1.0 g (3.56 mmol) of ethyl 4-nitrophenyl L-trans-epoxysuccinate and 626 mg (4.70 mmol) of 2-aminoindane.

m.p.: 92°–95° C.

$^1$H-NMR (DMSO-d$_6$) δ: 8.75(1H,d,J=5.8 Hz), 7.35(4H, m), 4.47(1H,m), 4.15(2H,m), 3.60(1H,d,J=1.0 Hz), 3.58(1H, d,J=1.0 Hz), 3.12(2H,ddd,J=16.1,7.3,4.2 Hz), 2.80(2H,dd, J=16.1,5.6 Hz), 1.21(3H,t,J=7.1 Hz).

Mass: FAB(+) m/e 276 (MH)$^+$.

Preparation Example 4

L-3-trans-(2-Indanylcarbamoyl)oxirane-2-carboxylic acid

Following a process similar to the process of Preparation Example 2, 590 mg (2.15 mmol) of the compound obtained in Preparation Example 3 were hydrolyzed to obtain a crude product. The crude product was recrystallized from ethyl acetate-hexane to obtain 380 mg of the title compound.

m.p.: 161°–164° C.

$^1$H-NMR (DMSO-d$_6$) δ: 13.45(1H,br.s), 8.75(1H,d,J=7.1 Hz), 7.22–7.14(4H,m), 4.53–4.45(1H,m), 3.54(1H,d,J=2.0 Hz), 3.49(1H,d,J=1.7 Hz), 3.20(2H,dd,J=7.6,4.5 Hz), 3.16 (1H,dd,J=7.3,2.7 Hz), 2.83(1H,d,J=5.6 Hz), 2.89(1H,d,J= 5.6 Hz).

Mass: FAB(-) m/e 246 (M-H)$^-$.

Preparation Example 5

Ethyl L-3-trans-[(S)-1-carbamoyl-2-phenylethylcarbamoyl]oxirane-2-carboxylate

Following a process similar to the process of Preparation Example 1, 7.0 g of the title compound were obtained from 8.0 g (28.47 mmol) of ethyl 4-nitrophenyl L-trans-epoxysuccinate and 4.7 g (28.47 mmol) of L-phenylalanine amide.

m.p.: 166°–169° C.

$^1$H-NMR (DMSO-d$_6$) δ: 8.60(1H,d,J=8.4 Hz), 7.60(1H, s), 7.30–7.20(5H,m), 7.17(1H,s), 4.51–4.45(1H,m), 4.20–4.13(2H,m), 3.63(1H,d,J=2.0 Hz), 3.40(1H,d,J=1.6 Hz), 3.06(2H,dd,J=13.6,4.4 Hz), 2.79(1H,dd,J=13.6,10.0 Hz), 1.22(3H,t,J=6.8 Hz).

Mass: FAB(+) m/e 307 (MH)$^+$.

Preparation Example 6

L-3-trans-[(S)-1-Carbamoyl-2-phenylethylcarbamoyl]oxirane-2-carboxylic acid

Following a process similar to the process of Preparation Example 2, 7.0 g of the compound obtained in Preparation Example 5 were hydrolyzed to obtain 3.0 g of the title compound.

m.p.: 181°–198° C. (dec.).

$^1$H-NMR (DMSO-d$_6$) δ: 13.47(1H,br.s), 8.54(1H,d,J=8.4 Hz), 7.59(1H,s), 7.30–7.15(5H,m), 7.14(1H,s), 4.50–4.45 (1H,m), 3.57(1H,d,J=1.2 Hz), 3.26(1H,d,J=1.6 Hz), 3.05 (1H,dd,J=13.6,4.4 Hz), 2.79(1H,dd,J=13.6,10.0 Hz).

Preparation Example 7

Ethyl L-3-trans-(3-phenylpropylcarbamoyl)oxirane-2-carboxylate

Following a process similar to the process of Preparation Example 1, 485 mg of the title compound (oily substance) were obtained from 500 mg (1.78 mmol) of ethyl 4-nitrophenyl L-trans-epoxysuccinate and 288 mg (2.31 mmol) of 3-phenyl-1-propylamine.

$^1$H-NMR (CDCl$_3$) δ: 7.32–7.16(5H,m), 6.01(1H,br.s), 4.26(2H,m), 3.64(1H,d,J=2.0 Hz), 3.35(1H,d,J=2.0 Hz), 3.30(2H,dt,J=7.1,6.1 Hz), 2.64(2H,t,J=7.6 Hz), 1.85(2H,tt, J=7.6,7.3 Hz), 1.32(3H,t,J=7.1 Hz).

Mass: FAB(+) m/e 278 (MH)$^+$.

Preparation Example 8

Ethyl L-3-trans-(2,2-diphenylethylcarbamoyl)oxirane-2-carboxylate

Following a process similar to the process of Preparation Example 1, 1.35 g of the title compound (oily substance) were obtained from 1 g (3.56 mmol) of ethyl 4-nitrophenyl L-trans-epoxysuccinate and 701 mg (3.56 mmol) of 2,2-diphenylethylamine.

$^1$H-NMR (CDCl$_3$) δ: 7.40(10H,m), 5.98(1H,br.s), 4.22 (2H,dq,J=7.1,1.4 Hz), 4.18(1H,t,J=8.8 Hz), 4.03–3.95(1H, m), 3.83–3.77(1H,m), 3.59(1H,d,J=2.0 Hz), 3.06(1H,d,J= 2.0 Hz), 1.29(3H,t,J=7.1 Hz).

Mass: FAB(+) m/e 340 (MH)$^+$.

Preparation Example 9

Ethyl L-3-trans-benzylcarbamoyloxirane-2-carboxylate

Following a process similar to the process of Preparation Example 1, 259 mg of the title compound were obtained from 500 mg (1.80 mmol) of ethyl 4-nitrophenyl L-trans-epoxysuccinate and 190 mg (1.80 mmol) of benzylamine.

m.p.: 95°–97° C.

$^1$H-NMR (CDCl$_3$) δ: 7.36–7.24(5H,m), 6.43(1H,br.s), 4.46–4.43(2H,m), 4.31–4.23(2H,m), 3.74(1H,d,J=1.9 Hz), 3.49(1H,d,J=2.0 Hz), 1.31(3H,t,J=7.1 Hz).

Mass: FAB(+) m/e 250 (MH)$^+$.

Preparation Example 10

L-3-trans-Benzylcarbamoyloxirane-2-carboxylic acid

Following a process similar to the process of Preparation Example 2, 259 mg (1.04 mmol) of the compound obtained in Preparation Example 9 were hydrolyzed to obtain 215 mg of the title compound.

m.p.: 123°–124.5° C.

$^1$H-NMR (CDCl$_3$) δ: 7.38–7.24(5H,m), 6.34(1H,br.s), 4.46(2H,d,J=5.9 Hz), 3.78(1H,d,J=1.7 Hz), 3.53(1H,d,J=2.0 Hz).

Mass: FAB(−) m/e 222 (M−H)$^-$.

Preparation Example 11

N-Benzyloxycarbonyl-L-phenylalanine-2-phenylethylamide

Following a process similar to the process of Preparation Example 1, 1.9 g of the title compound were obtained from 2.0 g (4.8 mmol) of N-benzyloxycarbonyl-L-phenylalanine 4-nitrophenyl ester and 577 mg (4.8 mmol) of 2-phenylethylamine.

m.p.: 137°–138.5° C.

$^1$H-NMR (CDCl$_3$) δ: 7.34–7.01(15H,m), 5.60(1H,br.s), 5.28(1H,br.s), 5.07(2H,s), 4.29(1H,dd,J=2.0,14.6 Hz), 3.50–3.36(2H,m), 3.09(1H,dd,J=6.8,14.6 Hz), 2.99(1H,dd, J=8.0,13.6 Hz), 2.70–2.58(2H,m).

Mass: FAB(+) m/e 403 (MH)$^+$.

Preparation Example 12

L-Phenylalanine-2-phenylethylamide hydrochloride

The condensate (1.65 g, 4.3 mmol) obtained in Preparation Example 11 was dissolved in a mixed solvent (100:1) of methanol-chloroform, and 10% palladium on carbon (1.65 g) was added to the solution. The mixture was stirred at room temperature for 1 hour in a hydrogen atmosphere. After completion of the reaction, the catalyst was separated by filtration, and the filtrate was concentrated under reduced pressure to obtain 1.13 g of the title compound.

m.p.: 64°–67° C.

$^1$H-NMR (CDCl$_3$) δ: 7.90(1H,br.t,J=6.0 Hz), 7.28–7.15 (10H,m), 3.41–3.25(1H,m), 2.88(1H,dd,J=5.1,13.3 Hz), 2.66(2H,t,J=7.3 Hz), 2.58(1H,dd,J=8.2,13.3 Hz), 1.91(2H, br.s).

Mass: FAB(+) m/e 269 (MH)$^+$.

Preparation Example 13

Ethyl L-3-trans-[(S)-1-(2-phenylethylcarbamoyl)-2-phenylethylcarbamoyl]oxirane-2-carboxylate Following a process similar to the process of Preparation Example 1, 1.20 g of the title compound were obtained from 1.10 g (3.90 mmol) of ethyl 4-nitrophenyl L-trans-epoxysuccinate and 1.0 g (3.90 mmol) of L-phenylalanine-2-phenylethylamide hydrochloride.

m.p.: 151°–155° C.

$^1$H-NMR (DMSO-d$_6$) δ: 8.70(1H,d,J=8.8 Hz), 8.26(1H, t,J=5.4 Hz), 7.30–7.18(10H,m), 4.52–4.47(1H,m), 4.20–4.14(2H,m), 3.64(1H,d,J=1.5 Hz), 3.43(1H,d,J=1.5 Hz), 3.36–3.35(2H,m), 2.94(1H,dd,J=13.7,4.9 Hz), 2.75 (1H,dd,J=13.7,9.8 Hz), 2.67(2H,t,J=7.3 Hz), 1.22(3H,t,J= 7.3 Hz).

Mass: FAB(+) m/e 411 (MH)$^+$.

Preparation Example 14

L-3-trans-[(S)-1-(2-Phenylethylcarbamoyl)-2-phenylethylcarbamoyl]oxirane-2-carboxylic acid Following a process similar to the process of Preparation Example 2, 1.20 g (2.90 mmol) of the compound obtained in Preparation Example 13 were hydrolyzed to obtain 1.10 g of the title compound.

m.p.: 154°–155.5° C.

$^1$H-NMR (DMSO-d$_6$) δ: 8.66(1H,d,J=8.8 Hz), 8.25(1H, br.t,J=5.4 Hz), 7.30–7.18(10H,m), 4.52–4.47(1H,m), 3.58 (1H,d,J=1.3 Hz), 3.29(1H,d,J=2.0 Hz), 3.28–3.21(2H,m), 2.94(1H,dd,J=13.7,4.9 Hz), 2.75(1H,dd,J=13.2,9.8 Hz), 2.67(2H,t,J=7.3 Hz).

Mass: FAB(−) m/e 381 (M−H)$^-$.

Preparation Example 15

N-Benzyloxycarbonyl-L-phenylalanine benzylamide

Following a process similar to the process of Preparation Example 1, 1.65 g of the title compound were obtained from 2.0 g (4.8 mmol) of N-benzyloxycarbonyl-L-phenylalanine 4-nitrophenyl ester and 510 mg (4.8 mmol) of benzylamine.

m.p.: 160°–162° C.

$^1$H-NMR (DMSO-d$_6$) δ: 7.34–7.06(15H,m), 5.90(1H, br.s), 5.33(1H,br.s), 5.08(2H,s), 4.42–4.37(1H,m), 4.34(2H, d,J=5.9 Hz), 3.16(1H,dd,J=5.8,13.6 Hz), 3.04(1H,dd,J=7.8, 13.7 Hz).

Mass: EI$^+$ m/e 388 (M)$^+$.

Preparation Example 16

L-Phenylalanine benzylamide hydrochloride

Following a process similar to the process of Preparation Example 12, 1.65 g (4.25 mmol) of N-benzyloxycarbonyl-L-phenylalanine benzylamide were catalytically hydrogenated to obtain 1.1 g of the title compound.

m.p.: 166°–170° C.

$^1$H-NMR (DMSO-d$_6$) δ: 8.89(1H,br.s), 8.29(2H,br.s), 7.33–7.07(10H,m), 4.34(1H,dd,J=5.9,15.1 Hz), 4.22(1H,dd, J=6.2,15.6 Hz), 4.19–4.00(1H,m), 3.05(2H,d,J=6.7 Hz).

Mass: FAB(+) m/e 255 (MH)$^+$.

Preparation Example 17

Ethyl L-3-trans-[(S)-1-benzylcarbamoyl-2-phenylethylcarbamoyl]oxirane-2-carboxylate Following a process similar to the process of Preparation Example 1, 1.22 g of the title compound were obtained from 1.0 g (3.70 mmol) of 4-nitrophenyl L-trans-epoxysuccinate and 1.10 g (3.70 mmol) of L-phenylalanine benzylamide hydrochloride obtained in Preparation Example 16.

m.p.: 165°–170° C.

$^1$H-NMR (DMSO-d$_6$) δ: 8.78(1H,d,J=8.8 Hz), 8.67(1H, t,J=5.9 Hz), 7.31–7.14(10H,m), 4.62–4.57(1H,m), 4.32–4.23(2H,m), 4.19–4.15(2H,m), 3.65(1H,d,J=1.5 Hz), 3.43(1H,d,J=1.5 Hz), 3.05(1H,dd,J=13.2,4.9 Hz), 2.84(1H, dd,J=13.7,9.8 Hz), 1.21(3H,t,J=8.3 Hz).

Mass: FAB(+) m/e 397 (MH)$^+$.

Preparation Example 18

L-3-trans-[(S)-1-Benzylcarbamoyl-2-phenylethylcarbamoyl]oxirane-2-carboxylic acid Following a process similar to the process of Preparation Example 2, 1.23 g (3.10 mmol) of the compound obtained in Preparation Example 17 were hydrolyzed to obtain 1.1 g of the title compound.

m.p.: 137°–149° C.

$^1$H-NMR (DMSO-d$_6$) δ: 8.62–8.60(2H,m), 7.30–7.15 (10H,m), 4.62–4.56(1H,m), 4.33–4.22(2H,m), 3.59(1H,d,J= 1.7 Hz), 3.37(1H,d,J=1.2 Hz), 3.06(1H,dd,J=13.4,4.9 Hz), 2.84(1H,dd,J=13.7,9.5 Hz).

Mass: FAB(+) m/e 369 (MH)$^+$.

Preparation Example 19

Ethyl L-3-trans-dibenzylcarbamoyloxirane-2-carboxylate

Following a process similar to the process of Preparation Example 1, 436 mg of the title compound were obtained from 500 mg (1.80 mmol) of ethyl 4-nitrophenyl L-trans-epoxysuccinate and 351 mg (1.80 mmol) of dibenzylamine.

m.p.: 83°–85° C.

$^1$H-NMR (DMSO-d$_6$) δ: 7.37–7.18(10H,m), 4.80(1H,d, J=13.7 Hz), 4.65(1H,d,J=14.1 Hz), 4.63(1H,d,J=12.1 Hz), 4.51(1H,d,J=12.1 Hz), 4.09(1H,d,J=1.6 Hz), 4.05(1H,q,J= 5.9 Hz), 3.57(1H,d,J=1.6 Hz), 1.14(3H,t,J=5.9 Hz).

Mass: FAB(+) m/e 340 (MH)$^+$.

Preparation Example 20

L-3-trans-Dibenzylcarbamoyloxirane-2-carboxylic acid

Following a process similar to the process of Preparation Example 2, 430 mg (1.3 mmol) of the compound obtained in Preparation Example 19 were hydrolyzed to obtain 400 mg of the title compound (oily substance). $^1$H-NMR (DMSO-d$_6$) δ: 7.38–7.20(10H,m), 4.76(1H,d,J=13.7 Hz), 4.67(1H,d,J=13.7 Hz), 4.55(2H,d,J=12.5 Hz), 4.50(1H,d,J= 12.1 Hz), 4.05(1H,s), 3.52(1H,s).

Mass: FAB(+) m/e 312 (MH)$^+$.

Preparation Example 21

Ethyl L-3-trans-(1-naphthylcarbamoyl)oxirane-2-carboxylate

Following a process similar to the process of Preparation Example 1, 4.92 g of the title compound were obtained from 6.2 g (21.9 mmol) of ethyl 4-nitrophenyl L-trans-epoxysuccinate and 626 mg (21.9 mmol) of 1-aminonaphthalene.

m.p.: 117°–120° C.

$^1$H-NMR (DMSO-d$_6$) δ: 8.23(1H,br.s), 8.00(1H,d,J=7.6 Hz), 7.89(1H,d,J=7.6 Hz), 7.76–7.73(2H,m), 7.59–7.48(3H, m), 4.36–4.30(2H,m), 3.97(1H,d,J=2.0 Hz), 3.78(1H,d,J= 1.7 Hz), 1.36(3H,t,J=7.3 Hz).

Mass: FAB(−) m/e 284 (M−H)$^-$.

Preparation Example 22

L-3-trans-(1-naphthylcarbamoyl) oxirane-2-carboxylic acid

Following a process similar to the process of Preparation Example 2, 4.9 g (18.3 mmol) of the compound obtained in Preparation Example 21 were hydrolyzed to obtain 4.92 g of the title compound.

m.p.: 188°–195° C. (dec.).

$^1$H-NMR (DMSO-d$_6$) δ: 8.1–8.07(1H,m), 7.98–7.95(1H, m), 7.82(1H,d,J=8.0 Hz), 7.73(1H,d,J=7.6 Hz), 7.61–7.50 (3H,m), 4.04(1H,d,J=1.0 Hz), 3.70(1H,d,J=0.8 Hz).

Mass: FAB(+) m/e 258 (MH)$^+$.

Preparation Example 23

Nα-Fluorenylmethyloxycarbonyl-Nε-t-butoxycarbonyl-L-lysine-1-naphthylamide

Under cooling with ice water, 2.97 g (22 mmol) of 1-hydroxybenzotriazole and 4.60 g (24 mmol) of 1-ethyl-3-(3-dimethylaminopropyl)carbodiimide hydrochloride were added to an ethyl acetate solution (50 ml) of 9.37 g (20.0 mmol) of Nα-fluorenylmethyloxycarbonyl-Nε-t-butoxycarbonyl-L-lysine and 2.86 g (20.0 mmol) of 1-aminonaphthalene. The mixture was stirred overnight as it was. Water was added to the reaction mixture, and a solid deposited was collected by filtration, washed with ethyl acetate and dried, thereby obtaining 7.95 g of the title compound.

m.p.: 183°–184° C.

$^1$H-NMR (CDCl$_3$) δ: 8.57(1H,br.s), 8.0–6.7(15H,m), 5.64 (1H,br.s), 4.75–4.35(3H,m), 4.21(1H,t,J=6.9 Hz), 3.17(2H, br.s), 2.19–2.02(1H,m), 1.95–1.50(5H,m), 1.49(9H,s).

Mass: FAB(+) m/e 616 (M+Na)$^+$.

Preparation Example 24

Nε-t-Butoxycaronyl-L-lysine-1-naphthylamide

Dissolved in 50 ml of chloroform were 1.04 g (1.76 mmol) of the condensate obtained in Preparation Example 23, and 10 ml of piperidine were added to the solution at room temperature, followed by stirring for 1 hour. After completion of the reaction, the solvent was distilled off, and the residue was added with methanol and washed several times with n-hexane. Methanol was distilled off to obtain 679 mg of the title compound (oily substance).

$^1$H-NMR (DMSO-d$_6$) δ: 8.06(1H,d,J=8.5 Hz), 7.97(1H, d,J=7.5 Hz), 7.80(1H,d,J=8.1 Hz), 7.75(1H,d,J=7.3 Hz), 7.62–7.56(3H,m), 6.08(1H,s), 3.92(1H,br.t,J=6.1 Hz), 3.00–2.92(3H,m), 1.90–1.70(2H,m), 1.65(2H,br.s), 1.45 (3H,br.s), 1.35(9H,s).

Mass: EI(+) m/e 371 (M)$^+$.

Preparation Example 25

Nα-t-Butoxycarbonyl-Nε-benzyloxycarbonyl-L-lysine-2-indanylamide

Following a process similar to the process of Preparation Example 23, 30.8 g of the title compound were obtained from 28.53 g (75.08 mmol) of Nα-t-butoxycarbonyl-Nε-benzyloxycarbonyl-L-lysine and 10.0 g (75.08 mmol) of 2-aminoindane.

m.p.: 105°–106° C.

$^1$H-NMR (DMSO-d$_6$) δ: 8.05(1H,d,J=7.1 Hz), 7.32–7.28 (5H,m), 7.22–7.12(5H,m), 6.71(1H,d,J=8.3 Hz), 4.99(2H,s), 4.44(1H,dtt,J=7.6,7.1,6.1 Hz), 3.82(1H,m), 3.15(2H,dd,J= 15.6,7.4 Hz), 2.95(2H,dt,J=6.6,6.3 Hz), 2.75(1H,dd,J=15.1, 5.9 Hz), 2.71(2H,dd,J=16.6,5.6 Hz), 1.57–1.11(6H,m), 1.36 (9H,s).

Mass: FAB(+) m/e 496 (MH)$^+$.

Preparation Example 26

Nε-Benzyloxycarbonyl-L-lysine-2-indanylamide hydrochloride

Dissolved in 100 ml of ethyl acetate were 15.0 g (30.3 mmol) of the condensate obtained in Preparation Example 25, and 100 ml of 4N hydrochloric acid were added under cooling with ice water, followed by stirring for 2 hours. After completion of the reaction, the solvent was distilled off under reduced pressure to obtain 12.03 g of the title compound (amorphous substance).

$^1$H-NMR (DMSO-d$_6$) δ: 8.06(1H,d,J=8.5 Hz), 7.37–7.11 (9H,m), 5.00(2H,s), 4.56(1H,dtt,J=6.5,5.9,5.8 Hz), 3.82(1H, m), 3.20(2H,dd,J=16.0,7.4 Hz), 2.96(2H,dt,J=6.3,6.3 Hz), 2.86–2.71(2H,m), 1.46–1.21(4H,m).

Mass: FAB(+) m/e 396 (MH)$^+$.

Preparation Example 27

Nα-t-Butoxycarbonyl-Nε-benzyloxycarbonyl-L-lysine-9-fluorenylamide

Following a process similar to the process of Preparation Example 23, 18.9 g of the title compound were obtained from 19.0 g (50.0 mmol) of Nα-t-butoxycarbonyl-Nε-benzyloxycarbonyl-L-lysine and 11.42 g (50.0 mmol) of 9-aminoflurorene hydrochloride.

m.p.: 155°–157° C.

$^1$H-NMR (DMSO-d$_6$) δ: 8.40(1H,d,J=8.8 Hz), 7.86(2H, d,J=8.0 Hz), 7.46–7.23(12H,m), 6.82(1H,d,J=7.8 Hz), 6.00 (1H,d,J=8.5 Hz), 5.00(2H,s), 3.94(1H,m), 2.97(2H,m), 1.75–1.55(2H,m), 1.54–0.98(4H,m), 1.39(9H,s).

Mass: FAB(+) m/e 566 (MH)$^+$.

Preparation Example 28

Nε-Benzyloxycarbonyl-L-lysine-9-fluorenylamide hydrochloride

Following a process similar to the process of Preparation Example 26, 18.4 g (33.89 mol) of the condensate obtained in Preparation Example 27 was deblocked to obtain 14.5 g of the title compound.

m.p.: 234°–238° C.

$^1$H-NMR (DMSO-d$_6$) δ: 9.05(1H,d,J=8.3 Hz), 8.33(3H, br.s), 7.87(2H,d,J=7.3 Hz), 7.55(1H,d,J=7.3 Hz), 7.46–7.25 (10H,m), 6.02(1H,d,J=8.1 Hz), 4.99(2H,s), 3.86(1H,m), 2.98(2H,m), 1.78–1.76(2H,m), 1.42–1.37(4H,m).

Mass: FAB(+) m/e 444 (MH)$^+$.

Preparation Example 29

Nα-t-Butoxycarbonyl-Nε-benzyloxycarbonyl-L-lysine-dibenzylamide

Following a process similar to the process of Preparation Example 23, 8.9 g of the title compound were obtained from 11.40 g (30.0 mmol) of Nα-t-butoxycarbonyl-Nε-benzyloxycarbonyl-L-lysine and 6.21 g (31.5 nmol) of dibenzylamine.

m.p.: 117°–118° C.

$^1$H-NMR (DMSO-d$_6$) δ: 7.36–7.12(17H,m), 4.98(2H,s), 4.66(1H,d,J=16.9 Hz), 4.69(2H,dd,J=15.4,14.9 Hz), 4.44 (1H,d,J=15.4 Hz), 4.34(1H,dt,J=9.0,4.2 Hz), 2.86(2H,m), 1.60–0.98(6H,m), 1.36(9H,s).

Mass: FAB(+) m/e 560 (MH)$^+$.

Preparation Example 30

Nε-Benzyloxycarbonyl-L-lysine dibenzylamide hydrochloride

Following a process similar to the process of Preparation Example 26, 8.8 g (15.74 mmol) of the condensate obtained in Preparation Example 29 was deblocked to obtain 6.51 g of the title compound (oily substance).

$^1$H-NMR (DMSO-d$_6$) δ: 8.27(2H,br.s), 7.44–7.11(15H, m), 5.00(2H,s), 4.74(1H,d,J=14.9 Hz), 4.71(1H,d,J=16.6 Hz), 4.43(1H,d,J=16.6 Hz), 4.22(1H,d,J=14.9 Hz), 2.92(2H, m), 1.77–1.56(2H,m), 1.39–1.21(4H,m).

Mass: FAB(+) m/e 460 (MH)$^+$.

Preparation Example 31

Nα-Benzyloxycarbonyl-Nε-t-butoxycarbonyl-L-lysine-3-chloroanilide

Dissolved in 20 ml of DMF were 1.52 g (4.0 mmol) of Nα-benzyloxycarbonyl-Nε-t-butoxycarbonyl-L-lysine and 510 mg (4.0 mmol) of 3-chloroanilide, and 595 mg (4.4 mmol) of 1-hydroxybenzotriazole and 920 mg (4.8 mmol) of 1-ethyl-3-(3-dimethylaminopropyl)carbodiimide hydrochloride were added to the solution under cooling with ice water, followed by stirring at room temperature for 24 hours. The reaction mixture was diluted with ethyl acetate, washed with water, dilute hydrochloric acid, a saturated aqueous solution of sodium hydrogencarbonate, water and saturated brine in that order, and dried over anhydrous magnesium sulfate. The desiccant was separated by filtration, and the filtrate was then concentrated under reduced pressure to obtain 1.898 g of the title compound.

m.p.: 101°–106° C.

$^1$H-NMR (DMSO-$d_6$) δ: 10.21(1H,s), 7.82(1H,s), 7.59–7.10(9H,m), 6.77(1H,br.s), 5.03(2H,s), 4.08(1H,br.d, J=5.6 Hz), 2.89(2H,br.s), 1.71–1.53(2H,m), 1.33(9H,s), 1.44–1.22(4H,m).

Mass:

FAB(+) m/e 490 (MH)$^+$.

Preparation Example 32

Nε-t-Butoxycaronyl-L-lysine anilide

Dissolved in 100 ml of methanol were 1.89 g (3.86 mmol) of the compound obtained in Preparation Example 31, and 378 mg of 10% palladium on carbon were added to the solution. The mixture was stirred at room temperature for 2 hours in a hydrogen atmosphere. The catalyst was separated by filtration, and the filtrate was concentrated under reduced pressure to obtain 1.468 g of the title compound.

$^1$H-NMR (DMSO-$d_6$) δ: 10.77(1H,s), 8.36(2H,br.s), 7.65–7.09(4H,m), 6.76(1H,br.t,J=5.6 Hz), 3.99(1H,br.t,J=6.6 Hz), 2.89(1H,br.dd,J=6.8,12.2 Hz), 1.81(2H,br.dd,J=3.9, 7.6 Hz), 1.45–1.28(4H,m), 1.34(9H,s).

Mass: FAB(+) m/e 322 (MH)$^+$.

Preparation Example 33

Nα-Benzyloxycarbonyl-Nε-t-butoxycarbonyl-L-lysine-2-methoxyanilide

Following a process similar to the process of Preparation Example 31, 1.12 g of the title compound were obtained from 1.5 g (3.94 mmol) of Nα-benzyloxycarbonyl-Nε-t-butoxycarbonyl-L-lysine and 738 mg (6.0 mmol) of 2-methoxyaniline.

m.p.: 107°–108° C.

$^1$H-NMR (DMSO-$d_6$) δ: 9.07(1H,s), 8.00(1H,d,J=7.6 Hz), 7.68(1H,d,J=7.1 Hz), 7.40–7.18(5H,m), 7.09–7.03(2H, m), 6.90(1H,dt,J=5.4,1.8 Hz), 6.77(1H,t,J=5.8 Hz), 5.06(2H, q,J=12.5 Hz), 4.20(1H,m), 3.8(3H,s), 2.89(2H,m), 1.76–1.51(2H,m), 1.50–1.20(4H,m), 1.36(9H,s).

Mass: FAB(+) m/e 508 (M+Na)$^+$.

Preparation Example 34

Nε-t-Butoxycarbonyl-L-lysine-2-methoxyanilide

Following a process similar to the process of Preparation Example 32, 720 mg of the title compound were obtained from 1.0 g (2.06 mmol) of the compound obtained in Preparation Example 33.

$^1$H-NMR (DMSO-$d_6$) δ: 10.14(1H,br.s), 8.28(1H,d,J=7.6 Hz), 7.06–6.86(3H,m), 6.76(1H,t,J=5.1 Hz), 3.58(3H,s), 3.28(1H,dd,J=8.1,3.9 Hz), 2.89(2H,m), 2.22(2H,br.s), 1.78–1.66(1H,m), 1.52–1.25(5H,m), 1.36(9H,s).

Mass: FAB(+) m/e 352 (MH)$^+$.

Preparation Example 35

Nα-Benzyloxycarbonyl-Nε-t-butoxycarbonyl-L-lysine-2-trifluoromethylanilide

Following a process similar to the process of Preparation Example 31, 138 mg of the title compound were obtained from 1.52 g (4.0 mmol) of Nα-benzyloxycarbonyl-Nε-t-butoxycarbonyl-L-lysine and 645 mg (4.0 mmol) of 2-trifluoromethylaniline.

m.p.: 136°–139° C.

$^1$H-NMR (DMSO-$d_6$) δ: 9.52(1H,s), 7.73(1H,d,J=7.8 Hz), 7.68(1H,dd,J=7.8,7.8 Hz), 7.56(1H,d,J=7.8 Hz), 7.52 (1H,d,J=7.8 Hz), 7.44(1H,dd,J=7.8,7.8 Hz), 7.40(5H,m), 6.78(1H,br.t,J=5.8 Hz), 5.05(2H,s), 4.25–4.15(1H,m), 2.50 (2H,br.d,J=5.2 Hz), 1.78–1.67(2H,m), 1.67–1.54(2H,m), 1.46–1.25(4H,m), 1.36(9H,s).

Mass: FAB(−) m/e 522 (M−H)$^-$.

Preparation Example 36

Nε-t-Butoxycarbonyl-L-lysine-2-trifluoromethylanilide

Following a process similar to the process of Preparation Example 32, 99 mg of the title compound were obtained from 130 mg (0.25 mmol) of the compound obtained in Preparation Example 35.

$^1$H-NMR (DMSO-$d_6$) δ: 8.24(1H,d,J=8.0 Hz), 7.71(1H, d,J=7.8 Hz), 7.67(1H,t,J=8.1 Hz), 7.31(1H,d,J=7.3 Hz), 6.77 (1H,br.t,J=4.9 Hz), 5.02(2H,br.s), 2.90(2H,d,J=5.8 Hz), 1.79–1.68(1H,m), 1.54–1.26(5H,m), 1.36(9H,s).

Mass: FAB(+) m/e 390 (MH)$^+$.

Preparation Example 37

Nα-Benzyloxycarbonyl-Nε-t-butoxycarbonyl-L-lysineindolinylamide

Following a process similar to the process of Preparation Example 31, 5.07 g of the title compound were obtained from 5.0 g (12.89 mmol) of Nα-benzyloxycarbonyl-Nε-t-butoxycarbonyl-L-lysine and 1.53 g (12.89 mmol) of indoline.

$^1$H-NMR (DMSO-$d_6$) δ: 8.08(1H,d,J=7.8 Hz), 7.69(1H, d,J=7.3 Hz), 7.42–7.28(5H,m), 7.25(1H,d,J=7.1 Hz), 7.15 (1H,dd,J=8.0,7.1 Hz), 7.01(1H,dd,J=8.1,7.1 Hz), 6.78(1H,t, J=5.5 Hz), 5.03(2H,s), 4.31(1H,m), 4.25(1H,dt,J=9.3,9.0 Hz), 4.17(1H,dt,J=9.3,8.6 Hz), 3.17(2H,t,J=8.1 Hz), 2.89 (2H,br.s), 1.72–1.22(6H,m), 1.35(9H,s).

Mass: FAB(+) m/e 504 (M+Na)$^+$.

Preparation Example 38

Nε-t -Butoxycarbonyl-L-lysineindolinylamide

Following a process similar to the process of Preparation Example 32, 1.80 g of the title compound were obtained from 2.50 g (5.20 mmol) of the compound obtained in Preparation Example 37.

$^1$H-NMR (DMSO-$d_6$) δ: 8.10(1H,d,J=7.8 Hz), 7.27(1H, d,J=7.3 Hz), 7.18(1H,dd,J=7.8,7.6 Hz), 7.04(1H,dd,J=7.6, 7.3 Hz), 6.78(1H,t,J=5.0 Hz), 4.25(1H,dt,J=9.3,8.7 Hz), 4.10(1H,dt,J=9.3,8.7 Hz), 3.86(1H,t,J=5.0 Hz), 3.17(2H,t,J= 8.1 Hz), 2.90(2H,m), 1.77–1.66(1H,m), 1.63–1.47(1H,m), 1.47–1.27(4H,m), 1.34(9H,s).

Mass: FAB(+) m/e 348 (MH)$^+$.

Preparation Example 39

Nα-Benzyloxycarbonyl-Nε-t-butoxycarbonyl-L-lysine-1-(4-chloronaphthyl)amide

Following a process similar to the process of Preparation Example 31, 1.08 g of the title compound were obtained from 1.52 g (4.0 mmol) of Nα-benzyloxycarbonyl-Nε-t-butoxycarbonyl-L-lysine and 711 mg (4.0 mmol) of 1-amino-4-chloronaphthalene.

m.p.: 157°–159° C.

$^1$H-NMR (DMSO-d$_6$) δ: 10.11(1H,s), 8.21(1H,d,J=8.1 Hz), 8.13(1H,d,J=8.3 Hz), 7.75–7.61(5H,m), 7.40–7.20(5H, m), 6.80(1H,br.t,J=5.9 Hz), 5.07(2H,s), 4.32(1H,br.dd,J= 9.0,13.2 Hz), 2.92(2H,br.s), 1.85–1.64(2H,m), 1.52–1.31 (4H,m), 1.37(9H,s).

Mass: FAB(+) m/e 539 (MH)$^+$.

Preparation Example 40

Nε-t-Butoxycarbonyl-L-lysine-1-(4-chloronaphthyl) amide

Following a process similar to the process of Preparation Example 32, 568 mg of the title compound were obtained from 816 mg (1.51 mmol) of the compound obtained in Preparation Example 39.

$^1$H-NMR (DMSO-d$_6$) δ: 8.24–7.14(6H,m), 6.81(1H,br.s), 4.01(1H,br.dd,J=7.1,14.2 Hz), 2.94(2H,br.d,J=3.7 Hz), 1.94–1.75(2H,m), 1.53–1.38(4H,m), 1.34(9H,s).

Mass: FAB(−) m/e 404 (M−H)$^−$.

Preparation Example 41

Nα-Benzyloxycarbonyl-Nε-t-butoxycarbonyl-L-lysine- 1naphthylamide

Following a process similar to the process of Preparation Example 31, 3.79 g of the title compound were obtained from 3.80 g (10.0 mmol) of Nα-benzyloxycarbonyl-Nε-t-butoxycarbonyl-L-lysine and 1.43 g (10.0 mmol) of 1-naphthylamine.

m.p.: 154°–156° C.

$^1$H-NMR (DMSO-d$_6$) δ: 9.98(1H,s), 8.02–8.05(1H,m), 7.92–7.94(1H,m), 7.77(1H,d,J=8.1 Hz), 7.46–7.62(5H,m), 7.30–7.37(5H,m), 6.79(1H,br.t,J=5.1 Hz), 5.07(2H,s), 4.33 (1H,br.dd,J=8.1,5.8 Hz), 2.92(2H,m), 1.64–1.86(2H,m), 1.36(9H,s), 1.29–1.51(4H,m).

Mass: FAB(+) m/e 544 (M+K)$^+$.

Preparation Example 42

Nε-t-Butoxycarbonyl-L-lysine-1-naphthylamide

Following a process similar to the process of Preparation Example 32, 1.5 g (3.0 mmol) of the compound obtained in Preparation Example 41 was catalytically hydrogenated to obtain 1.18 g of the title compound (oily substance).

$^1$H-NMR (DMSO-d$_6$) δ: 7.89–8.00(3H,m), 7.73(1H,d,J= 8.0 Hz), 7.74–7.61(4H,m), 6.79(1H,br.t,J=5.5 Hz), 3.45(1H, dd,J=5.1,7.6 Hz), 2.93(2H,d,J=5.4 Hz), 1.70–1.82(1H,m), 1.48–1.60(1H,m), 1.36(9H,s), 1.31–1.49(4H,m).

Mass: FAB(+) m/e 372 (MH)$^+$.

Preparation Example 43

L-Phenylalanine propylamide hydrochloride

Following a process similar to the process of Preparation Example 31, a condensate was obtained from 15 g (56.5 mmol) of N-t-butoxycarbonyl-L-phenylalanine and 3.5 g (58.4 mmol) of n-propylamine. Using 6 g of this condensate, deblocking was conducted in accordance with a process similar to the process of Preparation Example 26, thereby obtaining 4.7 g of the title compound.

m.p.: 154°–155° C.

$^1$H-NMR (DMSO-d$_6$) δ: 8.44(1H,t,J=5.6 Hz), 8.32(2H, br.s), 7.20–7.40(5H,m), 3.95(1H,t,J=6.4 Hz), 2.98–3.13(3H, m), 2.86–2.97(1H,m), 1.26–1.38(2H,m), 0.74(3H,t,J=11.2 Hz).

Mass: FAB(+) m/e 207 (MH)$^+$.

Preparation Example 44

Ethyl L-3-trans-[(S)-1-propylcarbamoyl-2-phenylethylcarbamoyl]oxirane-2-carboxylate Following a process similar to the process of Preparation Example 1, 2.6 g of the title compound were obtained from 2.2 g (7.9 mmol) of ethyl 4-nitrophenyl L-trans-epoxysuccinate and 2.0 g (8.2 mmol) of the compound obtained in Preparation Example 43.

m.p.: 149°–151° C.

$^1$H-NMR (DMSO-d$_6$) δ: 8.64(1H,d,J=8.3 Hz), 8.07(1H, t,J=5.6 Hz), 7.18–7.29(5H,m), 4.48–4.54(1H,m), 4.13–4.21 (2H,m), 3.64(1H,d,J=1.7 Hz), 3.43(1H,d,J=1.7 Hz), 2.90–3.08(3H,m), 2.80(1H,dd,J=9.5,13.7 Hz), 1.30–1.45 (4H,m), 1.22(3H,t,J=7.1 Hz), 0.79(1H,t,J=7.6 Hz).

Mass: FAB(+) m/e 349 (MH)$^+$.

Preparation Example 45

L-3-trans-[(S)-1-propylcarbamoyl-2-phenylethylcarbamoyl]oxirane-2-carboxylic acid Following a process similar to the process of Preparation Example 2, 2.6 g (7.3 mmol) of the compound obtained in Preparation Example 44 were hydrolyzed to obtain 1.8 g of the title compound.

m.p.: 184°–186° C.

$^1$H-NMR (DMSO-d$_6$) δ: 8.58(1H,d,J=8.6 Hz), 8.06(1H, t,J=5.6 Hz), 7.17–7.30(5H,m), 4.48–4.55(1H,m), 3.59(1H, d,J=1.7 Hz), 3.29(1H,d,J=1.7 Hz), 2.92–3.08(3H,m), 2.80 (1H,dd,J=9.5,13.6 Hz), 1.31–1.41(2H,m), 0.79(1H,t,J=7.3 Hz).

Mass: FAB(+) m/e 321 (MH)$^+$.

Preparation Example 46

D-Phenylalanine-2-phenylethylamide hydrochloride

Following a process similar to the process of Preparation Example 31, a condensate was obtained from 2 g (6.7 mmol) of N-benzyloxycarbonyl-D-phenylalanine and 1.1 g (9.1 mmol) of 2-phenylethylamine. The condensate was deblocked in accordance with a process similar to the process of Preparation Example 32, thereby obtaining 1.7 g of the title compound.

m.p.: 67°–69° C.

$^1$H-NMR (DMSO-d$_6$) δ: 7.89(1H,t,J=5.6 Hz), 7.10–7.35 (10H,m), 3.30–3.38(1H,m), 3.27(2H,dt,J=5.6,7.3 Hz), 2.89 (1H,dd,J=5.1,13.4 Hz), 2.66(2H,t,J=7.3 Hz), 2.58(1H,dd,J= 8.1,13.4 Hz), 1.60(2H,s).

Mass: FAB(+) m/e 269 (MH)$^+$.

Preparation Example 47

Ethyl L-3-trans-[(R)-1-(2-phenylethylcarbamoyl)-2-phenylethylcarbamoyl]oxirane-2-carboxylate Following a process similar to the process of Preparation Example 1, 1.0 g of the title compound were obtained from 1.0 g (3.5 mmol) of ethyl 4-nitrophenyl L-transepoxysuccinate and 1.0 g (3.7 mmol) of the compound obtained in Preparation Example 46.

m.p.: 148°–151° C.

$^1$H-NMR (DMSO-d$_6$) δ: 8.67(1H,d,J=8.6 Hz), 8.19(1H, t,J=5.8 Hz), 7.13–7.32(10H,m), 4.48(1H,m), 4.18(2H,q,J=7.1 Hz), 3.66(1H,d,J=1.7 Hz), 3.43(1H,d,J=1.7 Hz), 3.20–3.36(2H,m), 2.95(1H,dd,J=4.9,13.6 Hz), 2.74(1H,dd, J=9.5,13.6 Hz), 2.67(2H,t,J=7.3 Hz), 1.23(3H,t,J=7.1 Hz).

Mass: FAB(+) m/e 411 (MH)$^+$.

Preparation Example 48

L-3-trans-[(R)-1-(2-phenylethylcarbamoyl)-2-phenylethylcarbamoyl]oxirane-2-carboxylic acid Following a process similar to the process of Preparation Example 2, 1.0 g (2.4 mmol) of the compound obtained in Preparation Example 47 were hydrolyzed to obtain 890 mg of the title compound (frothy substance).

$^1$H-NMR (DMSO-d$_6$) δ: 8.68(1H,d,J=8.6 Hz), 8.18(1H, t,J=5.6 Hz), 7.20–7.35(10H,m), 4.43–4.52(1H,m), 3.60(1H, d,J=1.7 Hz), 3.25–3.37(3H,m), 2.95(1H,dd,J=4.9,13.4 Hz), 2.75(1H,dd,J=9.3,13.4 Hz), 2.67(3H,t,J=7.1 Hz).

Mass: FAB(+) m/e 384 (MH)$^+$.

Preparation Example 49

Nα-Benzyloxycarbonyl-Nε-t-butoxycarbonyl-L-lysine anilide

Following a process similar to the process of Preparation Example 31, 7.94 g of the title compound were obtained from 1.00 g (26.29 mmol) of Nα-benzyloxycarbonyl-Nε-t-butoxycarbonyl-L-lysine and 2.54 g (26.54 mmol) of aniline.

m.p.: 140°–142° C.

$^1$H-NMR (DMSO-d$_6$) δ: 9.98(1H,s), 7.59(1H,d,J=7.8 Hz), 7.52(1H,d,J=7.6 Hz), 7.28–7.37(6H,m), 7.04(1H,dd,J=7.3,7.3 Hz), 6.76(1H,br.t,J=5.1 Hz), 5.03(2H,s), 4.11(1H,dd, J=8.0,13.2 Hz), 2.82–2.95(2H,m), 1.53–1.73(2H,m), 1.33 (9H,s), 1.17–1.48(4H,m).

Mass: FAB(+) m/e 494 (M+K)$^+$.

Preparation Example 50

Nε-t-Butoxycarbonyl-L-lysine anilide

Following a process similar to the process of Preparation Example 32, 7.9 g (17.34 mmol) of the product obtained in Preparation Example 49 was deblocked to obtain 5.57 g of the title compound.

m.p.: 72°–74.5° C.

$^1$H-NMR (DMSO-d$_6$) δ: 9.98(1H,s), 9.80(1H,br.s), 8.02–8.05(1H,m), 7.92–7.94(1H,m), 7.63(2H,d,J=7.8 Hz), 7.29(2H,dd,J=8.0,8.0 Hz), 7.03(1H,dd,J=7.1,7.1 Hz), 6.75 (1H,br.t,J=5.4 Hz), 3.26(1H,dd,J=5.6,7.6 Hz), 2.89(2H,dd, J=6.3,12.4 Hz), 1.90(2H,br.s), 1.57–1.67(1H,m), 1.36(9H,s), 1.22–1.47(5H,m).

Mass: FAB(+) m/e 322 (MH)$^+$.

Preparation Example 51

L-Phenylalanine anilide hydrochloride

Following a process similar to the process of Preparation Example 23, a condensate was obtained from 25 g (94.0 mmol) of N-t-butoxycarbonyl-L-phenylalanine and 9.7 g (103.7 mmol) of aniline. Using 10.0 g of this condensate, deblocking was conducted in accordance with a process similar to the process of Preparation Example 26, thereby obtaining 7.3 g of the title compound.

m.p.: 189°–192° C.

$^1$H-NMR (DMSO-d$_6$) δ: 10.50(1H,s), 8.26(2H,br.s), 7.49–7.61(2H,m), 7.24–7.39(8H,m), 7.12(1H,t,J=7.3 Hz), 4.14–4.25(1H,m), 3.18(1H,dd,J=6.8,13.2 Hz), 3.09(1H,dd, J=7.1,13.2 Hz).

Mass: FAB(+) m/e 241 (MH)$^+$.

Preparation Example 52

Ethyl L-3-trans-[(S)-1-phenylcarbamoyl-2-phenylethylcarbamoyl]oxirane-2-carboxylate Following a process similar to the process of Preparation Example 1, 592 mg of the title compound were obtained from 1.0 g (3.6 mmol) of ethyl 4-nitrophenyl L-trans-epoxysuccinate and 1.2 g (4.3 mmol) of the compound obtained in Preparation Example 51.

m.p.: 176°–177° C.

$^1$H-NMR (DMSO-d$_6$) δ: 10.19(1H,s), 8.86(1H,d,J=8.3 Hz), 7.54–7.90(1H,m), 7.27–7.34(6H,m), 7.16–7.25(1H,m), 7.04–7.09(1H,m), 4.14–4.21(1H,m), 3.68(1H,d,J=1.7 Hz), 3.46(1H,d,J=1.7 Hz), 3.09(1H,dd,J=5.1,13.9 Hz), 2.91(1H, dd,J=9.8,13.9 Hz), 1.22(3H,t,J=7.1 Hz).

Mass: FAB(+) m/e 383 (MH)$^+$.

Preparation Example 53

L-3-trans-[(S)-1-phenylcarbamoyl-2-phenylethylcarbamoyl]oxirane-2-carboxylic acid Following a process similar to the process of Preparation Example 2, 5.74 g (1.5 mmol) of the compound obtained in Preparation Example 52 were hydrolyzed to obtain 4.78 g of the title compound.

m.p.: 169°–172° C.

$^1$H-NMR (DMSO-d$_6$) δ: 13.47(1H,br.s), 10.17(1H,s), 8.80(1H,d,J=8.3 Hz), 7.54–7.58(2H,m), 7.17–7.35(7H,m), 7.03–7.09(1H,m), 4.70–4.77(1H,m), 3.63(1H,d,J=1.7 Hz), 3.33(1H,d,J=1.7 Hz), 3.09(1H,dd,J=5.4,13.7 Hz), 2.91(1H, dd,J=9.5,13.7 Hz).

Mass: FAB(–) m/e 353 (M–H)$^-$.

Preparation Example 54

Nα-(L-3-trans-Ethoxycarbonyloxirane-2-carbonyl)-Nε-t-butoxycarbonyl-L-lysine anilide Following a process similar to the process of Preparation Example 32, 15.0 g (32.93 mmol) of the compound obtained in Preparation Example 49 was catalytically hydrogenated. The thus-obtained amine derivative and 9.26 g (32.93 mmol) of ethyl 4-nitrophenyl L-trans-epoxysuccinate were subjected to condensation in accordance with a process similar to the process of Preparation Example 1, thereby obtaining 13.49 g of the title compound.

m.p.: 171°–173° C.

$^1$H-NMR (DMSO-d$_6$) δ: 10.10(1H,s), 8.75(1H,d,J=7.8 Hz), 7.57(2H,d,J=7.6 Hz), 7.29(2H,dd,J=8.3,8.3 Hz), 7.04 (2H,dd,J=7.3,7.3 Hz), 6.75(1H,br.t,J=5.4 Hz), 4.43(1H,dd, J=8.1,13.7 Hz), 4.12–4.23(2H,m), 3.76(1H,d,J=1.7 Hz), 3.60(1H,d,J=1.9 Hz), 2.88(2H,dd,J=6.4,12.7 Hz), 1.34(9H, s), 1.22(3H,t,J=7.1 Hz).

Mass: FAB(+) m/e 502 (M+K)$^+$. FAB(–) m/e 462 (M–H)$^-$.

Preparation Example 55

Nα-{L-3-trans-Carboxyoxirane-2-carbonyl)-Nε-t-butoxycarbonyl-L-lysine anilide

Following a process similar to the process of Preparation Example 2, 10.0 g (21.57 mmol) of the compound obtained in Preparation Example 54 was hydrolyzed to obtain 8.25 g of the title compound.

m.p.: 129°–133° C.

$^1$H-NMR (DMSO-d$_6$) δ: 10.10(1H,s), 8.71(1H,d,J=7.8 Hz), 7.52(2H,d,J=8.0 Hz), 7.29(2H,dd,J=8.0,8.0 Hz), 7.04 (1H,dd,J=7.3,7.3 Hz), 6.75(1H,br.t,J=5.2 Hz), 4.43(1H,dd, J=8.1,13.7 Hz), 3.71(1H,d,J=2.0 Hz), 3.47(1H,d,J=2.0 Hz), 2.89(2H,dd,J=6.4,12.7 Hz), 1.57–1.78(2H,m), 1.36(9H,s), 1.19–1.46(4H,m).

Mass: FAB(–) m/e 434 (M–H)$^-$.

Preparation Example 56

L-Phenylalanine isopropylamide hydrochloride

Following a process similar to the process of Preparation Example 11, a condensate was obtained from 1.0 g (2.59 mmol) of N-t-butoxycarbonyl-L-phenylalanine 4-nitrophenyl ester and 278 mg (4.70 mmol) of isopropylamine. This condensate was deblocked in accordance with a process similar to the process of Preparation Example 26, thereby obtaining 370 mg of the title compound.

$^1$H-NMR (DMSO-d$_6$) δ: 8.29(1H,d,J=7.6 Hz), 7.20–7.35 (5H,m), 3.91(1H,dd,J=6.8,7.0 Hz), 3.77(1H,dsep,J=6.6,7.0 Hz), 3.07(1H,dd,J=6.6,13.7 Hz), 2.99(1H,dd,J=7.8,13.7 Hz), 1.04(3H,d,J=6.6 Hz), 0.87(3H,d,J=6.6 Hz).

Mass: FAB(+) m/e 207 (MH)$^+$.

Preparation Example 57

L-Phenylalanine methylamide hydrochloride

Following a process similar to the process of Preparation Example 1, a condensate was obtained from 1.0 g (2.59 mmol) of N-t-butoxycarbonyl-L-phenylalanine 4-nitrophenyl ester and 0.3 ml (3.98 mmol) of a 40% aqueous solution of methylamine. This condensate was deblocked in accordance with a process similar to the process of Preparation Example 26, thereby obtaining 425 mg of the title compound.

m.p.: 199°–200° C.

$^1$H-NMR (DMSO-d$_6$) δ: 8.41(1H,s), 7.21–7.35(5H,m), 3.92(1H,m), 3.01(1H,ddd,J=7.2,7.6,13.6 Hz), 2.58(3H,d,J= 4.6 Hz).

Mass: FAB(+) m/e 179 (MH)$^+$.

Preparation Example 58

L-Phenylalanine dimethylamide hydrochloride

Following a process similar to the process of Preparation Example 1, a condensate was obtained from 3.0 g (7.77 mmol) of N-t-butoxycarbonyl-L-phenylalanine 4-nitrophenyl ester and 1.0 ml (11.11 mmol) of a 50% aqueous solution of dimethylamine. This condensate was deblocked in accordance with a process similar to the process of Preparation Example 26, thereby obtaining 1.5 g of the title compound.

m.p.: 216°–217° C.

$^1$H-NMR (DMSO-d$_6$) δ: 7.20–7.34(5H,m), 4.53(1H,br.t, J=7.1 Hz), 3.10(1H,dd,J=6.1,13.4 Hz), 2.90(1H,dd,J=8.2, 13.4 Hz), 2.79(3H,s), 2.60(3H,s).

Mass: FAB(+) m/e 193 (MH)$^+$.

Preparation Example 59

L-Phenylalanine ethylamide hydrochloride

Following a process similar to the process of Preparation Example 1, a condensate was obtained from 3.2 g (8.29 mmol) of N-t-butoxycarbonyl-L-phenylalanine 4-nitrophenyl ester and 0.8 ml (14.22 mmol) of a 80% aqueous solution of ethylamine. Using 1.8 g of the condensate, deblocking was conducted in accordance with a process similar to the process of Preparation Example 26, thereby obtaining 1.14 g of the title compound.

m.p.: 180°–182° C.

$^1$H-NMR (DMSO-d$_6$) δ: 7.20–7.34(5H,m), 3.90(1H,dd, J=7.0,7.0 Hz), 3.09(2H,m), 3.01(1H,q,J=6.2 Hz), 0.93(3H, t,J=7.2 Hz).

Mass: FAB(+) m/e 193 (MH)$^+$.

Preparation Example 60

L-Phenylalanine cyclohexylamide hydrochloride

Following a process similar to the process of Preparation Example 11, a condensate was obtained from 3.0 g (7.77 mmol) of N-t-butoxycarbonyl-L-phenylalanine 4-nitrophenyl ester and 1.73 g (17.48 mmol) of cyclohexylamine. This condensate was deblocked in accordance with a process similar to the process of Preparation Example 26, thereby obtaining 730 mg of the title compound.

m.p.: 148°–150° C.

$^1$ H-NMR (DMSO-d$_6$) δ: 8.20(1H,d,J=7.6 Hz), 7.20–7.35 (5H,m), 3.93(1H,dd,J=6.8,7.6 Hz), 3.43–3.55(1H,m), 3.04 (1H,dd,J=6.6,13.4 Hz), 2.97(1H,dd,J-7.8,13.7 Hz), 1.40–1.75(5H,m), 0.85–1.35(5H,m).

Mass: FAB(+) m/e 247 (MH)$^+$.

Preparation Example 61

N-{N-[(2S,3S)-3-trans-Carboxyoxirane-2-carbonyl]-L-phenylalanyl}-1,8-diaminooctane The title compound was synthesized in accordance with the process described in European Patent Publication No. 065447A1.

m.p.: >210° C. (decomposed).

$^1$H-NMR (DMSO-d$_6$) δ: 7.92(1H,br.s), 7.27–7.16(5H,m), 4.42(1H,dd,J=5.4,9.3 Hz), 3.23(1H,d,J=1.7 Hz), 3.16–3.09 (1H,m), 2.96–2.92(2H,m), 2.89(1H,d,J=2.0 Hz), 2.78(1H, dd,J=9.5,13.4 Hz), 2.72(2H,t,J=7.3 Hz), 1.53–1.50(1H,m), 1.36–1.20(11H,m).

Mass: FAB(+) m/e 406 (MH)$^+$.

Example 1

Nα-[L-3-trans-(2-phenylethylcarbamoyl)oxirane-2-carbonyl]-Nε-t-butoxycarbonyl-L-lysine-1-naphthylamide Triethylamine (1 ml) was added dropwise to a DMF solution (50 ml) of 785 mg (3.34 mmol) of the compound obtained in Preparation Example 2, 585 mg (3.80 mmol) of hydrous 1-hydroxybenzotriazole, 720 mg (3.76 mmol) of 1-ethyl-3-(3-dimethylaminopropyl)-carbodiimide hydrochloride and 1.24 g (3.34 mmol) of Nε-t-butoxycarbonyl-L-lysine-1-naphthylamide under cooling with ice water. After completion of the addition, the mixture was stirred at room temperature for 16 hours. The reaction mixture was concentrated under reduced pressure, and the residue was added with 1N hydrochloric acid and ethyl acetate to extract it. The extract was then washed with saturated brine. After the resultant organic layer was dried over magnesium sulfate and filtered, the solvent was distilled off under reduced pressure. The resultant crude product was recrystallized from ethanol-hexane to obtain 680 mg of the title compound.

m.p.: 205°–207° C.

$^1$H-NMR (DMSO-$d_6$) δ: 10.11(1H,s), 8.79(1H,d,J=7.6 Hz), 8.48(1H,d,J=5.6 Hz), 8.02(1H,d,J=8.4 Hz), 7.94(1H,d, J=8.4 Hz), 7.79(1H,d,J=8.3 Hz), 7.62–7.48(4H,m), 7.31–7.18(4H,m), 6.18(1H,br.t,J=5.1 Hz), 4.64(1H,dt,J=8.0, 7.8 Hz), 3.69(1H,d,J=1.7 Hz), 3.54(1H,d,J=1.7 Hz), 3.34 (2H,m), 2.94(2H,m), 2.74(1H,t,J=7.4 Hz), 1.90–1.25(6H, m), 1.44(9H,s).

Mass: FAB(+) m/e 611 (M+Na)$^+$ FAB(−) m/e 587 (M−H)$^−$.

Example 2

Nα-[L-3-trans-(2-phenylethylcarbamoyl)oxirane-2-carbonyl]-L-lysine-1-naphthylamide hydrochloride Trifluoroacetic acid was added to a methylene chloride solution (1 ml) of 100 mg (0.17 mmol) of the compound obtained in Example 1, followed by stirring at room temperature for 1 hour. The reaction mixture was concentrated under reduced pressure, and the residue was dissolved in ethyl acetate. Under cooling with ice water, a solution (1 ml) of 4N hydrochloric acid in methyl acetate was added to the residue solution. The solvent was distilled under reduced pressure out of the resultant mixture to obtain a crude product. The product was washed with ethyl acetate to obtain 89 mg of the title compound.

m.p.: 115°–116° C.

$^1$H-NMR (DMSO-$d_6$) δ: 10.15(1H,s), 8.83(1H,d,J=7.8 Hz), 8.52(1H,d,J=5.7 Hz), 8.03–7.17(12H,m), 4.67(1H,dt, J=7.8,3.3 Hz), 3.69(1H,s), 3.57(1H,s), 3.31(2H,dt,J=7.8,3.4 Hz), 2.83(2H,m), 2.73(2H,t,J=7.2 Hz), 1.91(1H,m), 1.80 (1H,m), 1.61(2H,m), 1.46(2H,m).

Mass: FAB(+) m/e 489 (MH)$^+$ FAB(−) m/e 487 (M−H)$^−$.

IR (KBr, cm$^{-1}$): 700.0, 725.0, 800.0, 1505.4, 1538.5, 1663.0.

Example 3

Nα-[L-3-trans-(2-phenylethylcarbamoyl)oxirane-2-carbonyl]-Nε-benzyloxycarbonyl-L-lysine dibenzylamide Following a process similar to the process of Example 1, a crude product was obtained from 800 mg (3.40 mmol) of the compound obtained in Preparation Example 2 and 1.69 g (3.40 mmol) of Nε-benzyloxycarbonyl-L-lysine dibenzylamide. The crude product was recrystallized from ethyl acetate-hexane to obtain 1.2 g of the title compound.

m.p.: 135°–136° C.

$^1$H-NMR (DMSO-$d_6$) δ: 8.86(1H,d,J=7.8 Hz), 8.48(1H, d,J=5.6 Hz), 7.40–7.13(20H,m), 4.99(2H,s), 4.76(1H,dt,J= 8.3,5.6 Hz), 4.67(1H,d,J=15.4 Hz), 4.64(1H,d,J=16.9 Hz), 4.48(1H,d,J=16.8 Hz), 4.26(1H,d,J=15.4 Hz), 3.62(1H,d,J= 1.5 Hz), 3.49(1H,d,J=1.5 Hz), 3.34(2H,m), 2.91(2H,dt,J= 6.3,6.0 Hz), 2.74(1H,d,J=7.5 Hz), 1.64–1.53(2H,m), 1.36–1.10(4H,m).

Mass: FAB(+) m/e 677 (MH)$^+$.

Example 4

Nα-[L-3-trans-(2-phenylethylcarbamoyl)oxirane-2-carbonyl]-L-lysine dibenzylamide hydrochloride Suspended in a mixed solution (5.5 ml) of methanolchloroform (10:1) were 100 mg (0.16 mmol) of the compound obtained in Example 3 and 100 mg of 10% palladium on carbon. The suspension was stirred at room temperature for 2 hours in a hydrogen atmosphere. The catalyst was separated by filtration from the reaction mixture, and the residue was filtered through a membrane filter having a pore size of 0.2 μm. The solvent was distilled under reduced pressure out of the filtrate, thereby obtaining 42 mg of the title compound.

m.p.: 113°–115° C.

$^1$H-NMR (DMSO-$d_6$) δ: 8.90(1H,d,J=7.6 Hz), 8.53(1H, m), 7.39–7.16(15H,m), 4.78(1H,m), 4.66(1H,d,J=15.1 Hz), 4.64(1H,d,J=16.8 Hz), 4.49(1H,d,J=17.1 Hz), 4.27(1H,d,J= 15.1 Hz), 3.63(1H,s), 3.51(1H,m), 3.38(2H,m), 2.75(1H,t, J=7.4 Hz), 2.68(2H,m), 1.63–1.60(2H,m), 1.48–1.44(2H,m), 1.43–1.24(2H,m).

Mass: FAB(+) m/e 543 (MH)$^+$. IR (KBr, cm$^{-1}$): 700.4, 760.0, 1045.0, 1536.0, 1644.7, 1648.4.

Example 5

Nα-[L-3-trans-(2-phenylethylcarbamoyl)oxirane-2-carbonyl]-Nε-benzyloxycarbonyl-L-lysine-9-fluorenylamide Following a process similar to the process of Example 1, a crude product was obtained from 800 mg (3.40 mmol) of the compound obtained in Preparation Example 2 and 1.63 g (3.40 mmol) of Nε-benzyloxycarbonyl-L-lysine-9-fluorenylamide. The crude product was dissolved in ethyl acetate, and water was added to the solution, thereby obtaining 648 mg of the title compound.

m.p.: 250°–252° C.

$^1$H-NMR (DMSO-$d_6$) δ: 8.68(1H,d,J=8.6 Hz), 8.62(1H, d,J=7.6 Hz), 8.49(1H,t,J=5.6 Hz), 7.86(2H,d,J=7.3 Hz), 7.46–7.17(16H,m), 6.01(1H,d,J=8.5 Hz), 5.00(2H,s), 4.32 (1H,dt,J=7.6,5.6 Hz), 3.65(1H,d,J=1.7 Hz), 3.52(1H,d,J=1.7 Hz), 3.34(2H,m), 2.98(2H,dt,J=6.1,6.1 Hz), 2.74(1H,t,J=7.6 Hz), 1.78–1.59(2H,m), 1.52–1.22(4H,m).

Mass: FAB(+) m/e 661 (MH)$^+$ FAB(+) m/e 683 (M+Na)$^+$.

Example 6

Nα-[L-3-trans-(2-phenylethylcarbamoyl)oxirane-2-carbonyl]-L-lysine-9-fluorenylamide hydrochloride Following a process similar to the process of Example 4, a crude product was obtained from 100 mg (0.15 mmol) of the compound obtained in Example 5. The crude product was recrystallized from methanol-ether to obtain 20 mg of the title compound.

m.p.: 205°–208° C.

$^1$H-NMR (DMSO-$d_6$) δ: 8.70(1H,d,J=8.2 Hz), 8.65–8.60 (2H,m), 8.33(1H,s), 8.00(2H,br.s), 7.86(2H,d,J=7.6 Hz), 7.47–7.19(10H,m), 6.01(1H,d,J=8.1 Hz), 4.35(1H,m), 3.58 (1H,s), 3.35(2H,m), 2.76(4H,m), 1.81–1.25(6H,m).

Mass: FAB(+) m/e 527 (MH)$^+$.

IR (KBr, cm$^{-1}$): 705.0, 744.1, 1540.4, 1639.9, 1655.9.

Example 7

Nα-[L-3-trans-(2-indanylcarbamoyl)oxirane-2-carbonyl]-Nε-benzyloxycarbonyl-L-lysine-2-indanylamide Following a process similar to the process of Example 1, a crude product was obtained from 800 mg (3.24 mmol) of the compound obtained in Preparation Example 4 and 1.63 g (3.80 mmol) of Nε-benzyloxycarbonyl-L-lysine-2-indanylamide. The crude product was washed with a mixed solution of ethyl acetate-methylene chloride, thereby obtaining 624 mg of the title compound.

m.p.: 218°–220° C.

$^1$H-NMR (DMSO-d$_6$) δ: 8.75(1H,d,J=7.0 Hz), 8.52(1H, d,J=8.3 Hz), 8.35(1H,t,J=7.1 Hz), 7.38–7.12(13H,m), 4.99 (2H,s), 4.49(1H,dqui,J=7.1,6.1 Hz), 4.23(1H,dt,J=8.3,5.6 Hz), 3.66(1H,d,J=1.7 Hz), 3.49(1H,d,J=2.0 Hz), 3.21–3.12 (4H,m), 2.95(2H,q,J=6.6 Hz), 2.84–2.69(4H,m), 1.60–1.51 (2H,m), 1.40–1.34(2H,m), 1.26–1.19(2H,m).

Mass: FAB(+) m/e 625 (MH)$^+$.

Example 8

Nα-[L-3-trans-(2-indanylcarbamoyl)oxirane-2-carbonyl]-L-lysine-2-indanylamide hydrochloride Following a process similar to the process of Example 4, a crude product was obtained from 100 mg (0.15 mmol) of the compound obtained in Example 7. The crude product was recrystallized from methanol-ether to obtain 73 mg of the title compound.

m.p.: 142°–143° C.

$^1$H-NMR (DMSO-d$_6$) δ: 8.84(1H,d,J=7.1 Hz), 8.59(1H, d,J=8.3 Hz), 8.42(1H,d,J=8.3 Hz), 7.82(2H,br.s), 7.22–7.13 (8H,m), 4.55–4.40(2H,m), 4.25(1H,m), 3.66(1H,d,J=1.2 Hz), 3.53(1H,d,J=1.2 Hz), 3.37–3.12(4H,m), 2.82–2.71(6H, m), 1.70–1.50(2H,m), 1.49–1.35(2H,m), 1.35–1.15(2H,m).

Mass: FAB(+) m/e 528 (MH)$^+$.

IR (KBr, cm$^{-1}$): 743.0, 905.0, 1543.6, 1650.4.

Example 9

Nα-[L-3-trans-(2-indanylcarbamoyl)oxirane-2-carbonyl]-Nε-benzyloxycarbonyl-L-lysine-9-fluorenylamide Following a process similar to the process of Example 1, a crude product was obtained from 247 mg (1.0 mmol) of the compound obtained in Preparation Example 4 and 527 mg (1.0 mmol) of Nε-benzyloxycarbonyl-L-lysine-9-fluorenylamide. The crude product was washed with a mixed solution of ethyl acetate-methylene chloride, thereby obtaining 330 mg of the title compound.

m.p.: >280° C.

$^1$H-NMR (DMSO-d$_6$) δ: 8.82(1H,d,J=7.1 Hz), 8.67(1H, d,J=8.3 Hz), 8.63(1H,d,J=7.6 Hz), 7.45–7.14(16H,m), 5.99 (1H,d,J=8.3 Hz), 5.00(2H,s), 4.49(1H,m), 4.32(1H,dt,J=7.6, 7.6 Hz), 3.70(1H,d,J=1.0 Hz), 3.55(1H,d,J=1.0 Hz), 3.20 (1H,dd,J=15.6,4.7 Hz), 3.16(1H,dd,J=15.6,5.2 Hz), 2.98 (2H,dt,J=6.4,6.4 Hz), 2.83(2H,dd,J=15.6,5.4 Hz), 1.60–1.20 (2H,m), 1.45–1.00(4H,m).

Mass: FAB(+) m/e 673 (MH)$^+$.

Example 10

Nα-[L-3-trans-(2-indanylcarbamoyl)oxirane-2-carbonyl]-L-lysine-9-fluorenylamide hydrochloride Following a process similar to the process of Example 4, a crude product was obtained from 100 mg (0.15 mmol) of the compound obtained in Example 9. The crude product was washed with a mixed solution of methanoldiisopropyl ether to obtain 20 mg of the title compound.

m.p. >214°–217° C.

$^1$H-NMR (DMSO-d$_6$) δ: 7.86(2H,d,J=7.8 Hz), 7.48–7.10 (8H,m), 6.00(1H,d,J=8.3 Hz), 4.58(1H,m), 4.25(1H,m), 3.70 (1H,s), 3.58(1H,s), 3.18(2H,dt,J=15.9,6.5 Hz), 2.83(2H,dd, J=16.1,5.9 Hz), 2.74(2H,t,J=6.9 Hz), 1.83–1.61(2H,m), 1.61–1.47(2H,m), 1.471.22(2H,m).

Mass: FAB(+) m/e 539 (MH)$^+$.

IR (KBr, cm$^{-1}$): 743.5, 900.0, 1542.1, 1638.0, 1653.6.

Example 11

Nα-[L-3-trans-(2-indanylcarbamoyl)oxirane-2-carbonyl]-Nε-t-butoxycarbonyl-L-lysine-1-naphthylamide Following a process similar to the process of Example 1, 749 mg of the title compound were obtained from 772 mg (3.12 mmol) of the compound obtained in Preparation Example 4 and 1.24 g (3.34 mmol) of Nε-t-butoxycarbonyl-L-lysine-1-naphthylamide.

m.p.: 239°–241° C.

$^1$H-NMR (DMSO-d$_6$) δ: 10.10(1H,s), 8.79(2H,t,J=7.3 Hz), 8.03–8.00(1H,m), 7.95–7.93(1H,m), 7.79(1H,d,J=8.1 Hz), 7.60–7.47(4H,m), 7.22–7.13(4H,m), 6.81(1H,br.t,J=4.1 Hz), 4.65–4.60(1H,m), 4.53–4.45(1H,m), 3.27(1H,d,J=1.7 Hz), 3.54(1H,d,J=1.7 Hz), 3.21–3.13(2H,m), 2.94(2H,br.d, J=3.2 Hz), 2.83(1H,d,J=5.8 Hz), 2.79(1H,d,J=5.9 Hz), 1.95–1.83(1H,m), 1.83–1.70(1H,m), 1.54–1.43(4H,m), 1.40 (9H,s).

Mass: FAB(−) m/e 599 (M−H)$^−$.

Example 12

Nα-[L-3-trans-(2-indanylcarbamoyl)oxirane-2-carbonyl]-L-lysine-1-naphthylamide hydrochloride Following a process similar to the process of Example 2, 158 mg of the title compound were obtained from 200 mg (0.33 mmol) of the compound obtained in Example 11.

m.p.: 153°–155° C.

$^1$H-NMR (DMSO-d$_6$) δ: 10.16(1H,s), 8.88–8.85(2H,m), 8.03–7.94(2H,m), 7.85(2H,br.s), 7.80(1H,d,J=8.4 Hz), 7.61–7.48(4H,m), 7.21–7.13(4H,m), 4.67–4.63(1H,m), 4.54–4.46(1H,m), 3.74(1H,d,J=2.0 Hz), 3.59(1H,d,J=1.6 Hz), 3.21–3.14(2H,m), 2.84–2.79(4H,m), 1.99–1.86(1H,m), 1.86–1.71(1H,m), 1.71–1.54(2H,m), 1.56–1.39(2H,m).

Mass: FAB(+) m/e 501 (MH)$^+$.

IR (KBr, cm$^{-1}$): 744.7, 771.1, 794.8, 1573.9, 1644.9.

Example 13

Nα-{L-3-trans-[(S)-1-carbamoyl-2-phenylethylcarbamoyl]oxirane-2-carbonyl}-Nε-t-butoxycarbonyl-L-lysine-1-naphthylamide Following a process similar to the process of Example 1, 315 mg of the title compound were obtained from 1.24 g (3.34 mmol) of the compound obtained in Preparation Example 6 and 750 mg (2.70 mmol) of Nε-t-butoxycarbonyl-L-lysine-1-naphthylamide.

m.p.: >300° C. (dec.).

$^1$H-NMR (DMSO-d$_6$) δ: 10.16(1H,s), 8.78(1H,d,J=8.1 Hz), 8.71(1H,d,J=8.3 Hz), 8.05–8.03(1H,m), 7.95–7.93(1H, m), 7.79(1H,d,J=8.1 Hz), 7.64(1H,br.s), 7.61–7.47(4H,m), 7.31–7.17(5H,m), 7.12(1H,br.s), 6.82(1H,br.t,J=5.2 Hz), 4.67–4.60(1H,m), 4.51–4.46(1H,m), 3.62(1H,d,J=1.5 Hz), 3.59(1H,d,J=1.5 Hz), 3.03(1H,dd,J=13.9,4.6 Hz), 2.92(2H, br.d,J=5.9 Hz), 2.80(1H,dd,J=13.6,10.0 Hz), 1.95–1.85(1H, m), 1.85–1.75(1H,m), 1.50–1.45(4H,m), 1.33(9H,s).

Mass: FAB(−) m/e 630 (M−H)$^−$.

Example 14

Nα-{L-3-trans-[(S)-1-carbamoyl-2-phenylethylcarbamoyl]oxirane-2-carbonyl}-L-lysine-1-naphthylamide hydrochloride Following a process similar to the process of Example 2, 61 mg of the title compound were obtained from 100 mg (0.16 mmol) of the compound obtained in Example 13.

m.p.: >300° C. (dec.).

$^1$H-NMR (DMSO-$d_6$) δ: 10.19(1H,s), 8.82(1H,d,J=7.8 Hz), 8.72(1H,d,J=8.5 Hz), 8.05–7.94(2H,m), 7.92(2H,br.s), 7.79(1H,d,J=9.5 Hz), 7.63–7.48(4H,m),. 7.30–7.17(5H,m), 7.12(1H,br.s), 4.70–4.61(1H,m), 4.52–4.43(1H,m), 3.65 (1H,d,J=1.7 Hz), 3.60(1H,d,J=1.7 Hz), 3.03(1H,dd,J=13.6, 4.1 Hz), 2.85–2.77(3H,m), 2.00–1.85(1H,m), 1.85–1.73(1H, m), 1.73–1.60(2H,m), 1.60–1.35(2H,m).

Mass: FAB(+) m/e 532 (MH)$^+$.

IR (KBr, cm$^{-1}$): 620.5, 1121.4, 1503.9, 1658.5.

Example 15

Nα-{L-3-trans-[(S)-1-carbamoyl-2-phenylethylcarbamoyl]oxirane-2-carbonyl)-Nε-benzyloxycarbonyl-L-lysine dibenzylamide Following a process similar to the process of Example 1, 197 mg of the title compound were obtained from 1.38 g (2.70 mmol) of the compound obtained in Preparation Example 6 and 750 mg (2.70 mmol) of Nε-benzyloxycarbonyl-L-lysine dibenzylamide.

m.p.: 183°–185° C.

$^1$H-NMR (DMSO-$d_6$) δ:

8.82 (1H,d,J=7.8 Hz), 8.67(1H,d,J=8.5 Hz), 7.62(1H, br.s), 7.32–7.10(15H,m), 5.00(2H,s), 4.76(1H,dd,J=13.6,6.8 Hz), 4.68(1H,d,J=15.1 Hz), 4.64(1H,d,J=13.4 Hz), 4.52–4.46(1H,d,J=13.9 Hz), 4.24(1H,d,J=15.3 Hz), 3.58 (1H,d,J=1.7 Hz), 3.53(1H,d,J=1.7 Hz), 3.03(1H,dd,J=13.6, 4.6 Hz), 2.91(2H,dd,J=12.2,6.1 Hz), 2.81(1H,dd,J=12.9,9.8 Hz), 2.63–2.53(2H,m), 1.35–1.14(4H,m).

Mass: FAB(+) m/e 758 (M+K)$^+$.

Example 16

Nα-{L-3-trans-[(S)-1-carbamoyl-2-phenylethylcarbamoyl]oxirane-2-carbonyl}-L-lysine dibenzylamide hydrochloride Following a process similar to the process of Example 4, the title compound was obtained from 90 mg (0.13 mmol) of the compound obtained in Example 15. The compound was recrystallized from ethyl acetate to obtain 52 mg of the title compound.

m.p.: 139°–142° C.

$^1$H-NMR (DMSO-$d_6$) δ: 8.86(1H,d,J=8.7 Hz), 8.68(1H, d,J=8.5 Hz), 7.77(2H,s), 7.63(1H,s), 7.39–7.10(15H,m), 4.80–4.74(1H,m), 4.66(1H,d,J=15.1 Hz), 4.63(1H,d,J=16.6 Hz), 4.50–4.45(1H,m), 4.45(1H,d,J=16.4 Hz), 4.23(1H,d,J= 15.4 Hz), 3.58(1H,d,J=1.5 Hz), 3.51(1H,d,J=1.7 Hz), 3.01 (1H,dd,J=13.4,2.6 Hz), 2.79(1H,dd,J=13.4,4.9 Hz), 2.66 (2H,br.s), 1.70–1.50(2H,m), 1.50–1.35(2H,m), 1.35–1.13 (2H,m).

Mass: FAB(+) m/e 586 (MH)$^+$.

IR (KBr, cm$^{-1}$): 701.0, 1452.9, 1530.0, 1642.8, 1665.8.

Example 17

Nα-[L-3-trans-(3-phenylpropylcarbamoyl)oxirane-2-carbonyl]-Nε-benzyloxycarbonyl-L-lysine-1-naphthylamide Following a process similar to the process of Preparation Example 2, 480 mg (1.73 mmol) of the compound obtained in Preparation Example 7 was hydrolyzed to obtain a crude product. The crude product was subjected to a condensation reaction with 765 mg (1.89 mmol) of Nε-benzyloxycarbonyl-L-lysine-1-naphthylamide in accordance with a process similar to the process of Example 1, thereby obtaining 334 mg of the title compound.

m.p.: 205°–208° C.

$^1$H-NMR (DMSO-$d_6$) δ: 10.11(1H,s), 8.81(1H,d,J=7.6 Hz), 8.42(1H,t,J=5.6 Hz), 8.03–7.15(18H,m), 5.00(2H,s), 4.65(1H,m), 3.70(1H,s), 3.55(1H,s), 3.16–3.02(4H,m), 2.57 (1H,t,J=7.6 Hz), 1.91–1.87(4H,m), 1.70–1.36(4H,m).

Mass: FAB(+) m/e 637 (MH)$^+$.

Example 18

Nα-[L-3-trans-(3-phenylpropylcarbamoyl)oxirane-2-carbonyl]-L-lysine-1-naphthylamide hydrochloride Suspended in a mixed solvent (10 ml) of methanolacetic acid (9:1) were 100 mg (0.16 mmol) of the compound obtained in Example 3, and 100 mg of 10% palladium on carbon were added thereto. The suspension was stirred at room temperature for 2 hours in a hydrogen atmosphere. The catalyst was separated by filtration from the reaction mixture, and the residue was filtered through a membrane filter having a pore size of 0.2 μm. The solvent was distilled under reduced pressure out of the filtrate, and the residue was added with toluene and further with 4N hydrochloric acid-ethyl acetate, thereby obtaining a crude product. The crude product was washed with ethyl acetate to obtain 70 mg of the title compound.

m.p.: 175°–177° C.

$^1$H-NMR (DMSO-$d_6$) δ: 10.19(1H,s), 8.86(1H,d,J=7.8 Hz), 8.54(1H,t,J=5.6 Hz), 8.03–7.15(12H,m), 4.67(1H,dt,J= 7.8,5.4 Hz), 3.72(1H,d,J=1.0 Hz), 3.61(1H,d,J=1.0 Hz), 3.12 (2H,m), 2.28(2H,m), 2.60(2H,t,J=7.8 Hz), 2.00–1.35(8H, m).

Mass: FAB(+) m/e 503 (MH)$^+$.

IR (KBr, cm$^{-1}$): 720.0, 795.0, 805.0, 910.0, 1506.0, 1540.5, 1646.1, 1653.7.

Example 19

Nα-[L-3-trans-(2,2-diphenylethylcarbamoyl)oxirane-2-carbonyl]-Nε-benzyloxycarbonyl-L-lysine-1-naphthylamide Following a process similar to the process of Preparation Example 2, 1 g (3.23 mmol) of the compound obtained in Preparation Example 8 was hydrolyzed to obtain a crude product. The crude product was subjected to a condensation reaction with 1.29 mg (3.19 mmol) of Nε-benzyloxycarbonyl-L-lysine-1-naphthylamide in accordance with a process similar to the process of Preparation Example 1, thereby obtaining 851 mg of the title compound.

m.p.: 238°–242° C.

$^1$H-NMR (DMSO-$d_6$) δ: 10.10(1H,s), 8.75(1H,d,J=7.8 Hz), 8.47(1H,t,J=5.6 Hz), 8.01–7.93(2H,m), 7.78(1H,d,J= 8.1 Hz), 7.60–7.47(4H,m), 7.38–7.17(16H,m), 5.77(2H,s), 4.66(1H,m), 4.21(1H,t,J=7.8 Hz), 3.76(1H,br.t,J=7.2 Hz), 3.60(1H,d,J=1.7 Hz), 3.51(1H,d,J=1.9 Hz), 3.02(2H,m), 1.85–1.76(2H,m), 1.53–1.35(4H,m).

Mass: FAB(+) m/e 699 (MH)$^+$.

Example 20

Nα-[L-3-trans-(2,2-diphenylethylcarbamoyl)oxirane-2-carbonyl]-L-lysine-1-naphthylamide hydrochloride Following a process similar to the process of Example 18, a crude product was obtained from 200 mg (0.29 mmol) of the compound obtained in Example 19. The crude product was washed with methanol-ethyl acetate, thereby obtaining 107 mg of the title compound.

m.p.: 160°–164° C.

$^1$H-NMR (DMSO-d$_6$) δ: 10.18(1H,s), 8.81(1H,d,J=7.8 Hz), 8.55(1H,t,J=5.6 Hz), 8.03–7.94(4H,m), 7.79(1H,d,J=8.0 Hz), 7.61–7.48(4H,m), 7.29–7.17(8H,m), 4.65(1H,dt,J=5.0,4.4 Hz), 4.22(1H,t,J=7.8 Hz), 3.77(2H,m), 3.62(1H,d,J=2.0 Hz), 3.56(1H,d,J=1.7 Hz), 2.80(2H,br.t,J=7.2 Hz), 1.96–1.85(1H,m), 1.85–1.72(1H,m), 1.72–1.56(2H,m), 1.56–1.36(2H,m).

Mass: FAB(+) m/e 565 (MH)$^+$.

IR (KBr, cm$^{-1}$): 702.1, 750.0, 780.0, 800.0, 901.0, 1498.1, 1505.9, 1534.2, 1539.9.

Example 21

Nα-{L-3-trans-benzylcarbamoyloxirane-2-carbonyl)-Nε-benzyloxycarbonyl-L-lysine-1-naphthylamide Following a process similar to the process of Example 1, 460 mg of the title compound were obtained from 210 mg (1.02 mmol) of the compound obtained in Preparation Example 10 and 452 mg (1.02 mmol) of Nε-benzyloxycarbonyl-L-lysine-1-naphthylamide.

m.p.: 138°–140° C.

$^1$H-NMR (DMSO-d$_6$) δ: 10.12(1H,s), 8.92(1H,d,J=6.1 Hz), 8.85(1H,t,J=7.8 Hz), 8.03–7.93(2H,m), 7.79(1H,d,J=8.0 Hz), 7.80–7.47(4H,m), 7.36–7.25(10H,m), 5.00(2H,s), 4.64(1H,dd,J=13.4,8.6 Hz), 4.37–4.25(2H,m), 3.75(1H,d,J=2.0 Hz), 3.61(1H,d,J=2.0 Hz), 3.03(2H,br.d,J=6.1 Hz), 1.94–1.83(1H,m), 1.83–1.72(1H,m), 1.55–1.33(4H,m).

Mass: FAB(+) m/e 609 (MH)$^+$.

Example 22

Nα-{L-3-trans-benzylcarbamoyloxirane-2-carbonyl)-L-lysine-1-naphthylamide hydrochloride Following a process similar to the process of Example 4, a crude product was obtained from 100 mg (0.16 mmol) of the compound obtained in Example 21. The crude product was purified by means of a preparative ODS column chromatography (manufactured by Kusano; acetonitrile-0.01M ammonium acetate (1:1)), thereby obtaining 11 mg of the title compound.

m.p.: 149°–152° C.

$^1$H-NMR (DMSO-d$_6$) δ: 10.15(1H,s), 8.95(1H,d,J=6.4 Hz), 8.91(1H,d,J=7.8 Hz), 8.02–7.94(2H,m), 7.80(1H,d,J=8.3 Hz), 7.61–7.49(4H,m), 7.34–7.24(5H,m), 4.69(1H,m), 4.34(1H,dd,J=14.7,7.5 Hz), 4.29(1H,dd,J=14.7,5.9 Hz), 3.75(1H,d,J=1.5 Hz), 3.63(1H,d,J=2.0 Hz), 2.78(2H,br.t,J=6.8 Hz), 1.95–1.82(1H,m), 1.82–1.75(1H,m), 1.60–1.52(2H,m), 1.52–1.40(2H,m).

Mass: FAB(+) m/e 475 (MH)$^+$.

IR (KBr, cm$^{-1}$): 700.4, 771.2, 795.0, 890.0, 1563.6, 1645.3.

Example 23

Nα-{L-3-trans-[(S)-1-(2-phenylethylcarbamoyl)-2-phenylethylcarbamoyl]oxirane-2-carbonyl}-Nε-benzyloxycarbonyl-L-lysine-1-naphthylamide Following a process similar to the process of Example 1, 1.74 g of the title compound were obtained from 1.13 g (2.95 mmol) of the compound obtained in Preparation Example 14 and 1.31 g (2.95 mmol) of Nε-t-benzyloxy-carbonyl-L-lysine-1-naphthylamide.

m.p.: 243°–254° C. (dec.).

$^1$H-NMR (DMSO-d$_6$) δ: 10.11(1H,s), 8.74(2H,t,J=8.8 Hz), 8.04–7.93(2H,m), 7.78(1H,d,J=8.3 Hz), 7.62(1H,d,J=8.3 Hz), 7.57–7.47(4H,m), 7.35–7.16(10H,m), 5.00(2H,s), 4.67–4.62(1H,m), 4.53–4.47(1H,m), 3.63(1H,d,J=1.7 Hz), 3.61(1H,d,J=1.7 Hz), 3.51–3.18(2H,m), 3.03(2H,br.d,J=8.5 Hz), 2.91(1H,dd,J=13.7,4.9 Hz), 2.76(1H,dd,J=13.7,9.5 Hz), 2.66(2H,t,J=7.3 Hz), 1.93–1.82(1H,m), 1.82–1.71(1H,m), 1.56–1.33(4H,m).

Mass: FAB(+) m/e 808 (M+K)$^+$.

Example 24

Nα-{L-3-trans-[(S)-1-(2-phenylethylcarbamoyl)-2-phenylethylcarbamoyl]oxirane-2-carbonyl}-L-lysine-1-naphthylamide hydrochloride Following a process similar to the process of Example 18, a crude compound was obtained from 150 mg (0.19 mmol) of the compound obtained in Example 23. The crude product was recrystallized from ethyl acetate to obtain 59 mg of the title compound.

m.p.: 162°–165° C.

$^1$H-NMR (DMSO-d$_6$) δ: 10.18(1H,s), 8.84(1H,d,J=7.8 Hz), 8.77(1H,d,J=8.6 Hz), 8.26(1H,t,J=6.0 Hz), 8.05–7.94(2H,m), 7.80(1H,d,J=8.3 Hz), 7.77(2H,br.s), 7.63–7.48(4H,m), 7.28–7.17(10H,m), 4.69–4.66(1H,m), 4.51–4.48(1H,m), 3.65(1H,d,J=2.0 Hz), 3.62(1H,d,J=2.0 Hz), 3.37–3.16(2H,m), 2.94–2.84(1H,dd,J=13.4,4.6 Hz), 2.83–2.73(3H,m), 2.66(1H,t,J=7.3 Hz), 2.00–1.80(1H,m), 1.80–1.75(1H,m), 1.75–1.55(2H,m), 1.55–1.31(2H,m).

Mass: FAB(+) m/e 636 (MH)$^+$.

IR (KBr, cm$^{-1}$): 700.5, 795.0, 1536.4, 1648.7.

Example 25

Nα-{L-3-trans-[(S)-1-benzylcarbamoyl-2-phenylethylcarbamoyl]oxirane-2-carbonyl)-Nε-benzyloxycarbonyl-L-lysine-1-naphthylamide Following a process similar to the process of Example 1, 2.0 g of the title compound were obtained from 1.1 g (3.0 mmol) of the compound obtained in Preparation Example 18 and 1.31 g (2.95 mmol) of Nε-benzyloxycarbonyl-L-lysine-1-naphthylamide.

m.p.: 196°–202° C.

$^1$H-NMR (DMSO-d$_6$) δ: 10.10(1H,s), 8.81(1H,d,J=8.6 Hz), 8.76(1H,d,J=7.6 Hz), 8.64(1H,d,J=5.9 Hz), 8.03–7.92 (2H,m), 7.77(1H,d,J=8.0 Hz), 7.61–7.46(5H,m), 7.34–7.12 (10H,m), 4.99(2H,s), 4.67– 4.55(2H,m), 4.31–4.19(2H,m), 3.63(1H,s), 3.04–2.98(3H,m), 2.86(1H,dd,J=13.7,9.5 Hz), 1.95–1.70(2H,m), 1.55–1.30(4H,m).

Mass: FAB(+) m/e 778 (M+Na)$^+$.

Example 26

Nα-{L-3-trans-[(S)-1-benzylcarbamoyl-2-phenylethylcarbamoyl]oxirane-2-carbonyl}-L-lysine-1-naphthylamide hydrochloride Following a process similar to the process of Example 18, a crude product was obtained from 150 mg (0.20 mmol) of the compound obtained in Preparation Example 25. The crude product was purified by means of a preparative ODS column chromatography (manufactured by Kusano;

acetonitrile-1% acetic acid (1:2)), thereby obtaining 9 mg of the title compound.

m.p.: 184°–189° C.

$^1$H-NMR (DMSO-d$_6$) δ: 10.14(1H,s), 8.82(1H,d,J=8.0 Hz), 8.66(1H,br.t,J=5.6 Hz), 8.04–7.94(2H,m), 7.80(1H,d, J=8.1 Hz), 7.63–7.48(4H,m), 7.30–7.13(10H,m), 4.67–4.57 (2H,m), 4.32–4.20(2H,m), 3.65(1H,d,J=1.5 Hz), 3.62(1H,d, J=2.0 Hz), 3.03(1H,dd,J=13.4,5.1 Hz), 2.85(1H,dd,J=13.4, 9.5 Hz), 2.78–2.72(2H,m), 1.95–1.70(2H,m), 1.64–1.50(2H, m), 1.50–1.34(2H,m).

Mass: FAB(+) m/e 622 (MH)$^+$.

IR (KBr, cm$^{-1}$): 699.5, 895.8, 1547.9, 1645.9.

Example 27

Nα-[L-3-trans-(dibenzylcarbamoyl)oxirane-2-carbonyl]-Nε-benzyloxycarbonyl-L-lysine-1-naphthylamide Following a process similar to the process of Example 1, 334 mg of the title compound were obtained from 400 mg (1.30 mmol) of the compound obtained in Preparation Example 20 and 508 mg (1.30 mmol) of Nε-benzyloxycarbonyl-L-lysine-1-naphthylamide.

m.p.: 218°–220° C.

$^1$H-NMR (DMSO-d$_6$) δ: 10.10(1H,s), 8.76(1H,d,J=8.0 Hz), 8.02–7.92(2H,m), 7.79(1H,d,J=8.3 Hz), 7.62(1H,d,J= 7.3 Hz), 7.53–7.47(4H,m), 7.35–7.18(10H,m), 4.99(2H,s), 4.72–4.65(3H,m), 4.58(1H,d,J=15.4 Hz), 4.46(1H,d,J=14.9 Hz), 4.00(1H,d,J=1.2 Hz), 3.81(1H,d,J=1.7 Hz), 3.01(2H, br.d,J=6.1 Hz), 1.92–1.70(2H,m), 1.55–1.31(4H,m).

Mass: FAB(−) m/e 697 (M−H)$^-$.

Example 28

Nα-[L-3-trans-(dibenzylcarbamoyl)oxirane-2-carbonyl]-L-lysine-1-naphthylamide hydrochloride Following a process similar to the process of Example 18, 83 mg of the title compound were obtained from 150 mg (0.21 mmol) of the compound obtained in Example 27.

m.p.: 135°–138° C.

$^1$H-NMR (DMSO-d$_6$) δ: 10.14(1H,s), 8.85(1H,d,J=8.0 Hz), 8.02–7.94(2H,m), 7.80(1H,d,J=8.3 Hz), 7.76(2H,br.d), 7.63(1H,d,J=6.8 Hz), 7.54–7.49(4H,m), 7.34–7.18(10H,m), 4.74–4.62(3H,m), 4.59(1H,d,J=14.9 Hz), 4.46(1H,d,J=14.9 Hz), 4.01(1H,d,J=1.7 Hz), 3.83(1H,d,J=1.7 Hz), 2.79(2H, br.s), 1.98–1.82(1H,m), 1.82–1.17(1H,m), 1.71–1.55(2H, m), 1.55–1.38(2H,m).

Mass: FAB(+) m/e 565 (MH)$^+$.

IR (KBr, cm$^{-1}$): 701.4, 773.0, 794.3, 1538.2, 1650.2.

Example 29

Nα-[L-3-trans-(1-naphthylcarbamoyl)oxirane-2-carbonyl]-Nε-t-butoxycarbonyl-L-lysine-1-naphthylamide Following a process similar to the process of Example 1, 240 mg of the title compound were obtained from 859 mg (3.34 mmol) of the compound obtained in Preparation Example 22 and 1.24 g (3.34 mmol) of the compound obtained in Preparation Example 24.

m.p.: 230°–235° C.

$^1$H-NMR (DMSO-d$_6$) δ: 10.52(1H,s), 10.16(1H,d,J=0.5 Hz), 8.95(1H,d,J=7.8 Hz), 8.07–7.50(14H,m), 6.83(1H, br.s), 4.72(1H,br.s), 4.03(1H,d,J=1.4 Hz), 3.95(1H,d,J=1.5 Hz), 2.97(2H.br.s), 2.00–1.75(2H,m), 1.54–1.42(4H,br.d), 1.54(9H,s).

Mass: FAB(+) m/e 649 (M+K)$^+$.

Example 30

Nα-[L-3-trans-(1-naphthylcarbamoyl)oxirane-2-carbonyl]-L-lysine-1-naphthylamide hydrochloride Following a process similar to the process of Example 2, 81 mg of the title compound were obtained from 100 mg (0.16 mmol) of the compound obtained in Preparation Example 29.

m.p.: 172°–174° C.

$^1$H-NMR (DMSO-d$_6$) δ: 10.19(1H,br.s), 9.01(1H,br.d,J= 7.1 Hz), 8.07–7.50(14H,m), 4.74(1H,br.s), 4.07(1H,d,J=1.7 Hz), 3.95(1H,d,J=1.7 Hz), 2.83(2H,br.t,J=7.0 Hz), 2.00–1.75(2H,m), 1.75–1.45(4H,m).

Mass: FAB(+) m/e 511 (MH)$^+$.

IR (KBr, cm$^{-1}$): 771.2, 793.5, 890.0, 1538.1, 1645.0, 1667.6.

Example 31

Nα-{L-3-trans-[(S)-1-carbamoyl-2-phenylethylcarbamoyl]oxirane-2-carbonyl)-Nε-acetyl-L-lysine-1-naphthylamide Suspended in methylene chloride (20 ml) were 100 mg (0.18 mmol) of the compound obtained in Example 14, and triethylamine (2 ml) and acetic anhydride (2 ml) were added thereto, followed by stirring at room temperature for 15 hours. Crystals were separated by filtration from the reaction mixture and washed with methylene chloride, thereby obtaining 74 mg of the title compound.

m.p.: 238°–242° C.

$^1$H-NMR (DMSO-d$_6$) δ: 10.15(1H,br.s), 8.79(1H,d,J=8.3 Hz), 8.67(1H,d,J=8.5 Hz), 8.04–7.94(2H,m), 7.80(1H,d,J= 8.3 Hz), 7.61(1H,s), 7.63–7.48(4H,m), 7.30–7.19(5H,m), 7.11(1H,s), 4.66–4.61(1H,m), 4.52–4.46(1H,m), 3.62(1H,d, J=2.0 Hz), 3.59(1H,d,J=2.0 Hz), 3.10–3.00(3H,m), 2.80(1H, dd,J=13.6,10.0 Hz), 1.90–1.75(2H,m), 1.78(3H,s), 1.55–1.35(4H,m).

Mass: FAB(+) m/e 574 (MH)$^+$.

IR (KBr, cm$^{-1}$): 701.8, 769.8, 900.0, 1536.7, 1649.3.

Example 32

Nα-{L-3-trans-[(S)-1-(2-phenylethylcarbamoyl)-2-phenylethylcarbamoyl]oxirane-2-carbonyl}-Nε-acetyl-L-lysine-1-naphthylamide Following a process similar to the process of Example 31, 74 mg of the title compound were obtained from 100 mg (0.18 mmol) of the compound obtained in Example 24.

m.p.: 245°–270° C. (dec.).

$^1$H-NMR (DMSO-d$_6$) δ: 10.10(1H,s), 8.73(1H,d,J=8.3 Hz), 8.21(1H,br.t,J=5.6 Hz), 8.03–7.92(2H,m), 7.81(1H,br.t, J=5.3 Hz), 7.61–7.46(4H,m), 7.30–7.15(10H,m), 4.66–4.61 (1H,m), 4.51–4.46(1H,m), 3.62(1H,d,J=2.0 Hz), 3.59(1H,d, J=1.7 Hz), 3.84–3.17(2H,m), 3.04(2H,br.d,J=6.1 Hz), 2.90 (1H,dd,J=13.4,4.6 Hz), 2.75(1H,dd,J=13.7,9.5 Hz), 2.65 (2H,t,J=7.3 Hz), 1.77(3H,s), 1.90–1.70(2H,m), 1.50–1.30 (4H,m).

Mass: FAB(+) m/e 678 (MH)$^+$.

IR (KBr, cm$^{-1}$): 700.4, 895.0, 1548.0, 1650.1.

Example 33

Nα-{L-3-trans-[(S)-1-(2-phenylethylcarbamoyl)-2-phenylethylcarbamoyl]oxirane-2-carbonyl}-Nε-propanoyl-L-lysine-1-naphthylamide Following a process similar to the process of Example 31, 97 mg of the title compound were obtained from 100 mg (0.18 mmol) of the compound obtained in Example 24 and propionic anhydride (0.5 ml).

m.p.: >270° C.

$^1$H-NMR (DMSO-d$_6$) δ: 10.12(1H,s), 8.76(1H,d,J=7.3 Hz), 8.75(1H,d,J=8.5 Hz), 8.23(1H,t,J=5.5 Hz), 8.03(1H,dd, J=7.7,1.3 Hz), 7.95(1H,m), 7.79(1H,d,J=8.3 Hz), 7.74(1H, d,J=5.4 Hz), 7.64–7.13(14H,m), 4.64(1H,m), 4.49(1H,m), 3.62(1H,d,J=1.7 Hz), 3.06(2H,m), 2.91(2H,dd,J=13.5,5.5 Hz), 2.76(2H,dd,J=13.4,9.3 Hz), 2.65(2H,t,J=7.6 Hz), 2.04 (2H,q,J-7.6 Hz), 1.95–1.60(2H,m), 1.60–1.25(4H,m), 0.98 (3H,t,J=7.6 Hz).

Mass: FAB(+) m/e 692 (MH)$^+$.

IR (KBr, cm$^{-1}$): 700.0, 748.2, 772.3, 794.4, 900.0, 1506.1, 1545.4, 1648.4.

Example 34

Nα-{L-3-trans-[(S)-1-(2-phenylethylcarbamoyl)-2-phenylethylcarbamoyl]oxirane-2-carbonyl)-Nε-t-butoxycarbonyl-L-lysine anilide Following a process similar to the process of Example 1, 100 mg of the title compound were obtained from 191 mg (0.50 mmol) of the compound obtained in Preparation Example 14 and 245 mg (0.50 mmol) of the compound obtained in Preparation Example 32.

m.p.: 228°–230° C.

$^1$H-NMR (DMSO-d$_6$) δ: 10.12(1H,s), 8.75–8.72(2H,m), 8.23(1H,br.t,J=5.6 Hz), 7.59(2H,d,J=8.3 Hz), 7.18–7.32 (12H,m), 7.05(1H,t,J=7.3 Hz), 6.77(1H,br.t,J=5.4 Hz), 4.51–4.39(2H,m), 3.57(2H,d,J=2.2 Hz), 3.24–3.16(2H,m), 2.93–2.87(3H,m), 2.75(1H,dd,J=9.8,13.7 Hz), 2.66(2H,t,J= 7.6 Hz), 1.78–1.58(2H,m), 1.47–1.22(4H,m), 1.34(9H,s).

Mass: FAB(+) m/e 708 (M+Na)$^+$.

Example 35

Nα-{L-3-trans-[(S)-1-(2-phenylethylcarbamoyl)-2-phenylethylcarbamoyl]oxirane-2-carbonyl}-L-lysine anilide hydrochloride Following a process similar to the process of Example 2, 78 mg of the title compound were obtained from 90 mg (0.13 mmol) of the compound obtained in Preparation Example 14 and 245 mg (0.50 mmol) of the compound obtained in Example 34.

m.p.: 131°–133° C.

$^1$H-NMR (DMSO-d$_6$) δ: 10.18(1H,s), 8.80(1H,d,J=7.8 Hz), 8.75(1H,d,J=8.5 Hz), 8.26(1H,br.t,J=5.4 Hz), 7.68(2H, br.s), 7.61(2H,d,J=8.0 Hz), 7.33–7.18(1H,m), 7.05(1H,t,J= 7.3 Hz), 4.53–4.41(1H,m), 3.60(1H,s), 3.58(1H,d,J=0.7 Hz), 3.31–3.20(2H,m), 2.91(1H,dd,J=4.3,13.6 Hz), 2.81–2.72 (2H,m), 2.67(2H,t,J=7.3 Hz), 1.79–1.70(1H,m), 1.70–1.61 (1H,m), 1.61–1.49(2H,m), 1.45–1.27(2H,m).

Mass: FAB(+) m/e 586 (MH)$^+$.

IR (KBr, cm$^{-1}$): 699.7, 1203.4, 1445.7, 1547.0, 1651.0.

Example 36

Nα-{L-3-trans-[(S)-1-carbamoyl-2-phenylethylcarbamoyl]oxirane-2-carbonyl}-Nε-t-butoxycarbonyl-L-lysine-2-methoxyanilide Following a process similar to the process of Example 1, 180 mg of the title compound were obtained from 139 mg (0.50 mmol) of the compound obtained in Preparation Example 6 and 176 mg (0.50 mmol) of the compound obtained in Preparation Example 34.

m.p.: 169°–170.5° C.

$^1$H-NMR (DMSO-d$_6$) δ: 9.24(1H,s), 8.69(1H,d,J=8.1 Hz), 8.66(1H,d,J=8.6 Hz), 7.90(1H,dd,J=7.9,1.3 Hz), 7.60 (1H,d,J=1.2 Hz), 7.32–7.01(8H,m), 6.92–6.87(1H,m), 6.77 (1H,t,J=5.4 Hz), 4.55(1H,m), 4.48(1H,dt,J=9.4,4.5 Hz), 3.82 (3H,s), 3.58(1H,d,J=1.9 Hz), 3.56(1H,d,J=1.7 Hz), 3.02(1H, dd,J=13.7,4.3 Hz), 2.89(2H,dt,J=7.3,5.4 Hz), 2.80(1H,dd,J= 13.7,9.8 Hz), 1.82–1.56(2H,m), 1.47–1.22(4H,m), 1.36(9H, s).

Mass: FAB(+) m/e 650 (M+K)$^+$.

Example 37

Nα-{L-3-trans-[(S)-1-carbamoyl-2-phenylethylcarbamoyl]oxirane-2-carbonyl}-L-lysine-2-methoxyanilide hydrochloride Following a process similar to the process of Example 2, 65 mg of the title compound were obtained from 100 mg (0.16 mmol) of the compound obtained in Example 36.

m.p.: 162°–165° C.

$^1$H-NMR (DMSO-d$_6$) δ: 9.27(1H,s), 8.78(1H,d,J=7.8 Hz), 8.69(1H,d,J=8.6 Hz), 7.96(1H,d,J=7.6 Hz), 7.63(1H,s), 7.30–7.03(6H,m), 6.91(1H,t,J=7.3 Hz), 4.57(1H,m), 4.49 (1H,dt,J=9.5,4.5 Hz), 3.83(3H,s), 3.61(1H,d,J=1.4 Hz), 3.57 (1H,d,J=2.0 Hz), 3.03(1H,dd,J=13.7,4.4 Hz), 2.80(1H,dd,J= 13.9,10.4 Hz), 2.77(2H,m), 1.91–1.50(4H,m), 1.46–1.28 (2H,m).

Mass: FAB(+) m/e 512 (MH)$^+$.

IR (KBr, cm$^{-1}$): 775.0, 1531.8, 1536.5, 1650.2, 1659.4, 1666.1.

Example 38

Nα-{L-3-trans-[(S)-1-(2-phenylethylcarbamoyl)-2-phenylethylcarbamoyl]oxirane-2-carbonyl}-Nε-t-butoxycarbonyl-L-lysine-2-methoxyanilide Following a process similar to the process of Example 1, 120 mg of the title compound were obtained from 191 mg (0.50 mmol) of the compound obtained in Preparation Example 14 and 176 mg (0.50 mmol) of the compound obtained in Preparation Example 34.

m.p.: 219°–223° C.

$^1$H-NMR (DMSO-d$_6$) δ: 9.25(1H,s), 8.74(1H,d,J=9.5 Hz), 8.72(1H,d,J=8.3 Hz), 8.23(1H,t,J=5.5 Hz), 7.90(1H,d, J=7.8 Hz), 7.29–7.17(10H,m), 7.10–7.03(2H,m), 6.90(1H,t, J=7.3 Hz), 6.77(1H,t,J=5.4 Hz), 4.60(1H,dt,J=8.5,4.6 Hz), 4.49(1H,m), 3.82(3H,s), 3.58(1H,s), 3.57(1H,s), 3.23(2H, m), 2.94–2.90(3H,m), 2.75(1H,dd,J=13.7,9.8 Hz), 2.66(2H, t,J=7.6 Hz), 1.83–1.56(2H,m), 1.50–1.21(4H,m), 1.36(9H, s).

Mass: FAB(+) m/e 738 (M+Na)$^+$.

Example 39

Nα-{L-3-trans-[(S)-1-(2-phenylethylcarbamoyl)-2-phenylethylcarbamoyl]oxirane-2-carbonyl}-L-lysine-2-methoxyanilide hydrochloride Following a process similar to the process of Example 2, 80 mg of the title compound were obtained from 116 mg (0.16 mmol) of the compound obtained in Example 38.

m.p.: 118°–120° C.

$^1$H-NMR (DMSO-d$_6$) δ: 9.28(1H,s), 8.79(1H,d,J=7.6 Hz), 8.74(1H,d,J=8.5 Hz), 8.26(1H,t,J=5.7 Hz), 7.32–7.04 (13H,m), 6.91(1H,dd,J=7.6,7.3 Hz), 4.61–4.46(2H,m), 3.82

(3H,s), 3.60(1H,d,J=1.7 Hz), 3.58(1H,d,J=1.7 Hz), 3.25(2H, m), 2.88(1H,m), 2.75(3H,m), 2.64(2H,m), 1.90–1.49(4H, m), 1.48–1.28(2H,m).

Mass: FAB(+) m/e 616 (MH)$^+$.

IR (KBr, cm$^{-1}$): 700.8, 749.1, 1462.5, 1495.4, 1536.4, 1649.9, 1657.7.

Example 40

Nα-{L-3-trans-[(S)-1-carbamoyl-2-phenylethylcarbamoyl]oxirane-2-carbonyl)-Nε-t-butoxycarbonyl-L-lysine-2-trifluoromethylanilide Following a process similar to the process of Example 1, 66 mg of the title compound were obtained from 83 mg (0.30 mmol) of the compound obtained in Preparation Example 6 and 117 mg (0.30 mmol) of the compound obtained in Preparation Example 36.

m.p.: 164°–167° C.

$^1$H-NMR (DMSO-d$_6$) δ: 9.73(1H,s), 8.65(1H,d,J=8.1 Hz), 7.73(1H,d,J=8.1 Hz), 7.67(1H,t,J=7.7 Hz), 7.60(1H,s), 7.45(2H,t,J=9.0 Hz), 7.30–7.17(5H,m), 7.11(1H,s), 6.77 (1H,br.s), 4.54–4.45(2H,m), 3.59(1H,d,J=1.0 Hz), 3.54(1H, d,J=1.7 Hz), 3.03–2.99(1H,m), 2.90–2.88(2H,m), 2.79(1H, dd,J=9.8,13.4 Hz), 1.80–1.70(1H,m), 1.80–1.66(1H,m), 1.45–1.20(4H,m), 1.38(9H,s).

Mass: FAB(+) m/e 672 (M+Na)$^+$.

IR (KBr, cm$^{-1}$): 1130.3, 1175.8, 1204.1, 1321.1, 1539.8, 1673.1

Example 41

Nα-{L-3-trans-[(S)-1-carbamoyl-2-phenylethylcarbamoyl]oxirane-2-carbonyl}-L-lysine-2-trifluoromethylanilide hydrochloride Following a process similar to the process of Example 2, 37 mg of the title compound were obtained from 58 mg (0.09 mmol) of the compound obtained in Example 40.

m.p.: 135°–138° C.

$^1$H-NMR (DMSO-d$_6$) δ: 9.77(1H,s), 8.70(1H,d,J=8.0 Hz), 8.65(1H,d,J=8.4 Hz), 7.75–7.44(6H,m), 7.29–7.19(7H, m), 7.11(1H,s), 4.58–4.45(2H,m), 3.61(1H,s), 3.56(1H,s), 3.04–2.29(1H,m), 2.82–2.75(3H,m), 1.86–1.73(1H,m), 1.61–1.44(2H,m), 1.44–1.23(2H,m).

Mass: FAB(+) m/e 550 (MH)$^+$.

Example 42

Nα-{L-3-trans-[(S)-1-(2-phenylethylcarbamoyl)-2-phenylethylcarbamoyl]oxirane-2-carbonyl}-Nε-t-butoxycarbonyl-L-lysine-2-trifluoromethylanilide Following a process similar to the process of Example 1, 36 mg of the title compound were obtained from 88 mg (0.23 mmol) of the compound obtained in Preparation Example 14 and 90 mg (0.23 mmol) of the compound obtained in Preparation Example 36.

m.p.: 225°–227.5° C.

$^1$H-NMR (DMSO-d$_6$) δ: 9.74(1H,s), 8.73(1H,d,J=8.5 Hz), 8.66(1H,d,J=8.1 Hz), 7.73(1H,d,J=7.8 Hz), 7.67(1H,t, J=7.6 Hz), 7.47–7.42(2H,m), 7.28–7.16(10H,m), 4.55–4.45 (2H,m), 3.59(1H,s), 3.56(1H,s), 3.45–3.17(2H,m), 2.90–2.89(2H,m), 2.75(1H,dd,J=9.8,13.4 Hz), 2.65(2H,t,J= 7.4 Hz), 1.80–1.75(1H,m), 1.75–1.60(1H,m), 1.45–1.25(4H, m), 1.36(9H,s).

Mass: FAB(+) m/e 776 (M+Na)$^+$.

Example 43

Nα-{L-3-trans-[(S)-1-(2-phenylethylcarbamoyl)-2-phenylethylcarbamoyl]oxirane-2-carbonyl)-L-lysine-2-trifluoromethylanilide hydrochloride Following a process similar to the process of Example 2, 27 mg of the title compound were obtained from 30 mg (0.04 mmol) of the compound obtained in Example 43.

m.p.: 132°–135.5° C.

$^1$H-NMR (DMSO-d$_6$) δ: 9.78(1H,s), 8.72(1H,d,J=7.3 Hz), 8.24(1H,d,J=5.6 Hz), 7.74(1H,d,J=7.8 Hz), 7.70–7.66 (4H,m), 7.49–7.43(2H,m), 7.28–7.16(8H,m), 4.58–4.46(2H, m), 3.61(1H,d,J=1.2 Hz), 3.57(1H,d,J=1.2 Hz), 3.31–3.08 (2H,m), 2.90(2H,dd,J=3.9,13.4 Hz), 2.86–2.72(3H,m), 2.65 (2H,t,J=7.8 Hz), 1.80–1.75(1H,m), 1.75–1.65(1H,m), 1.65–1.49(2H,m), 1.49–1.30(2H,m).

Mass: FAB(+) m/e 654 (MH)$^+$.

IR (KBr, cm$^{-1}$): 1134.6, 1205.5, 1321.1, 1540.2, 1653.6, 1675.3.

Example 44

Nα-{L-3-trans-[(S)-1-carbamoyl-2-phenylethylcarbamoyl]oxirane-2-carbonyl}-Nε-t-butoxycarbonyl-L-lysine indolinylamide Following a process similar to the process of Example 1, 74 mg of the title compound were obtained from 139 mg (0.50 mmol) of the compound obtained in Preparation Example 6 and 174 mg (0.50 mmol) of the compound obtained in Preparation Example 38.

m.p.: 125°–126° C.

$^1$H-NMR (DMSO-d$_6$) δ: 8.86(1H,d,J=7.6 Hz), 8.66(1H, d,J=8.5 Hz), 8.07(1H,d,J=8.1 Hz), 7.60(1H,s), 7.29–7.11 (9H,m), 7.01(1H,dd,J=7.6,7.3 Hz), 6.79(1H,br.t,J=5.4 Hz), 4.57(1H,m), 4.47(1H,dt,J=9.5,4.5 Hz), 4.24(1H,m), 4.17 (1H,m), 3.56(1H,d,J=2.0 Hz), 3.53(1H,d,J=1.7 Hz), 3.17 (2H,t,J=8.5 Hz), 3.02(1H,dd,J=13.6,9.8 Hz), 2.89(2H,m), 2.79(1H,dd,J=13.6,4.4 Hz), 1.84–1.69(1H,m), 1.67–1.53 (1H,m), 1.46–1.20(4H,m), 1.35(9H,s).

Mass: FAB(−) m/e 606 (M−H)$^-$.

Example 45

Nα-{L-3-trans-[(S)-1-carbamoyl-2-phenylethylcarbamoyl]oxirane-2-carbonyl}-L-lysine indolinylamide hydrochloride Following a process similar to the process of Example 2, 44 mg of the title compound were obtained from 50 mg (0.08 mmol) of the compound obtained in Example 44.

m.p.: 120°–123° C.

$^1$H-NMR (DMSO-d$_6$) δ: 8.92(1H,d,J=7.3 Hz), 8.65(1H, d,J=8.3 Hz), 8.08(1H,d,J=8.8 Hz), 7.61(1H,s), 7.29–7.11 (9H,m), 7.03(1H,dd,J=7.6,7.3 Hz), 4.62(1H,m), 4.48(1H,dt, J=9.3,4.6 Hz), 4.24(1H,m), 4.17(1H,m), 3.58(1H,d,J=2.0 Hz), 3.54(1H,d,J=1.7 Hz), 3.18(2H,t,J=8.3 Hz), 3.02(1H,dd, J=13.8,4.5 Hz), 2.82–2.74(3H,m), 1.86–1.30(6H,m).

Mass: FAB(+) m/e 508 (MH)$^+$.

IR (KBr, cm$^{-3}$): 1134.4, 1203.6, 1530.5, 1536.3, 1650.3, 1667.6, 1677.4.

Example 46

Nα-{L-3-trans-[(S)-1-(2-phenylethylcarbamoyl)-2-phenylethylcarbamoyl]oxirane-2-carbonyl}-Nε-t-butoxycarbonyl-L-lysine indolinylamide Following a process similar to the process of Example 1, 478 mg of the title compound were obtained from 382 mg (1.00 mmol) of the compound obtained in Preparation Example 14 and 374 mg (1.00 mmol) of the compound obtained in Preparation Example 38.

m.p.: 115°–118° C.

$^1$H-NMR (DMSO-$d_6$) δ: 8.88(1H,d,J=7.6 Hz), 8.73(1H, d,J=8.6 Hz), 8.23(1H,t,J=5.6 Hz), 8.08(1H,d,J=7.8 Hz), 7.34–7.13(12H,m), 7.02(1H,dt,J=7.4,0.7 Hz), 6.79(1H,t,J= 5.4 Hz), 4.58(1H,m), 4.49(1H,dt,J=9.7,4.9 Hz), 4.21(2H,m), 3.57(1H,d,J=2.0 Hz), 3.55(1H,d,J=1.7 Hz), 3.28–3.21(2H, m), 3.17(2H,t,J=8.4 Hz), 2.90(3H,m), 2.74(1H,dd,J=13.9, 9.8 Hz), 2.66(1H,t,J=7.2 Hz), 1.82–1.71(1H,m), 1.68–1.55 (1H,m), 1.45–1.21(4H,m), 1.35(9H,s).

Mass: FAB(−) m/e 710 (M−H)$^−$.

Example 47

Nα-{L-3-trans-[(S)-1-(2-phenylethylcarbamoyl)-2-phenylethylcarbamoyl]oxirane-2-carbonyl}-L-lysine indolinylamide hydrochloride Following a process similar to the process of Example 2, 84 mg of the title compound were obtained from 100 mg (0.14 mmol) of the compound obtained in Example 46.

m.p.: 118°–120° C.

$^1$H-NMR (DMSO-$d_6$) δ: 8.93(1H,d,J=7.8 Hz), 8.71(1H, d,J=8.5 Hz), 8.24(1H,d,J=5.6 Hz), 8.08(1H,d,J=5.8 Hz), 7.28–7.15(12H,m), 7.03(1H,t,J=7.3 Hz), 4.62(1H,m), 4.48 (1H,dt,J=9.3,4.9 Hz), 4.21(2H,m), 3.58(1H,d,J=2.0 Hz), 3.55(1H,d,J=1.7 Hz), 3.35(2H,m), 3.20(2H,m), 2.91(1H,dd, J=13.7,4.6 Hz), 2.79(2H,t,J=7.6 Hz), 2.74(1H,dd,J=13.4,7.4 Hz), 2.66(2H,t,J=7.4 Hz), 1.79–1.38(6H,m).

Mass: FAB(+) m/e 612 (MH)$^+$.

IR (KBr, cm$^{-1}$): 701.1, 722.0, 1133.6, 1203.0, 1483.0, 1530.7, 1536.4, 1650.4, 1658.8, 1665.8.

Example 48

Nα-{L-3-trans-[(S)-1-carbamoyl-2-phenylethylcarbamoyl]oxirane-2-carbonyl}-L-lysine-1-(4-chloronaphthyl)amide hydrochloride Following a process similar to the process of Example 1, 50 mg of a crude condensate was obtained from 58 mg (0.21 mmol) of the compound obtained in Preparation Example 6 and 85 mg (0.21 mmol) of the compound obtained in Preparation Example 40. The crude condensate was then deblocked in accordance with a process similar to the process of Example 2, and the resultant crude product was purified by means of a preparative ODS column chromatography (manufactured by Kusano; acetonitrile-water (1:2)), thereby obtaining 10 mg of the title compound.

m.p.: 130°–135° C.

$^1$H-NMR (DMSO-$d_6$) δ: 10.22(1H,s), 8.82(1H,d,J=6.7 Hz), 8.65(1H,d,J=8.3 Hz), 8.21(1H,d,J=7.6 Hz), 8.10(1H,d, J=7.6 Hz), 7.75–7.61(6H,m), 7.29–7.17(5H,m), 7.10(1H,s), 4.67–4.61(1H,m), 4.51–4.45(1H,m), 3.62(1H,d,J=1.7 Hz), 3.58(1H,d,J=1.4 Hz), 3.01(1H,dd,J=4.4,13.6 Hz), 2.85–2.76 (3H,m), 1.95–1.85(1H,m), 1.85–1.70(1H,m), 1.70–1.55(2H, m), 1.55–1.40(2H,m).

Mass: FAB(+) m/e 566 (MH)$^+$.

IR (KBr, cm$^{-1}$): 1133.6, 1206.2, 1540.6, 1675.6, 1683.6.

Example 49

Nα-{L-3-trans-[(S)-1-(2-phenylethylcarbamoyl)-2-phenylethylcarbamoyl]oxirane-2-carbonyl}-L-lysine-1-(4-chloronaphthyl)amide hydrochloride Following a process similar to the process of Example 1, 228 mg of a crude condensate was obtained from 191 mg (0.50 mmol) of the compound obtained in Preparation Example 14 and 203 mg (0.50 mmol) of the compound obtained in Preparation Example 40. The crude condensate was then deblocked in accordance with a process similar to the process of Example 2, and the resultant crude product was purified by means of a preparative ODS column chromatography (manufactured by Kusano; acetonitrile-water (1:2)), thereby obtaining 33 mg of the title compound.

m.p.: 163°–166° C.

$^1$H-NMR (DMSO-$d_6$) δ: 10.25(1H,s), 8.85(1H,d,J=7.8 Hz), 8.75(1H,d,J=8.5 Hz), 8.25(1H,t,J=5.4 Hz), 8.22(1H,d, J=7.8 Hz), 8.12(1H,d,J=8.0 Hz), 7.76–7.62(6H,m), 7.30–7.17(10H,m), 4.68–4.60(1H,m), 4.53–4.47(1H,m), 3.64(1H,d,J=1.7 Hz), 3.61(1H,d,J=1.7 Hz), 3.30–3.17(2H, m), 3.91(1H,dd,J=4.9,13.4 Hz), 2.84–2.72(3H,m), 2.65(2H, t,J=7.3 Hz), 1.95–1.85(1H,m), 1.85–1.70(1H,m), 1.70–1.55 (2H,m), 1.55–1.40(2H,m).

Mass: FAB(+) m/e 670 (MH)$^+$.

IR (KBr, cm$^{-1}$): 700.5, 1135.4, 1203.4, 1539.9, 1650.6.

Example 50

Nα-{L-3-trans-[(S)-1-propylcarbamoyl-2-phenylethylcarbamoyl]oxirane-2-carbonyl}-Nε-t-butoxycarbonyl-L-lysine-1-naphthylamide Following a process similar to the process of Example 1, 350 mg of the title compound were obtained from 346 mg (0.93 mmol) of the compound obtained in Preparation Example 42 and 284 mg (0.89 mmol) of the compound obtained in Preparation Example 45.

m.p.: 228°–231° C.

$^1$H-NMR (DMSO-$d_6$) δ: 10.10(1H,s), 8.74(2H,d,J=8.1 Hz), 8.07(1H,t,J=10.5 Hz), 8.03(1H,d,J=8.3 Hz), 7.95(1H, d,J=7.6 Hz), 7.79(1H,d,J=8.1 Hz), 7.45–7.66(4H,m), 7.15–7.34(5H,m), 7.50–7.80(1H,m), 4.57–4.68(1H,m), 4.47–4.56(1H,m), 3.63(1H,s), 3.60(1H,s), 3.02(1H,dd,J= 6.6,13.2 Hz), 2.86–3.05(4H,m), 2.80(1H,dd,J=9.0,13.2 Hz), 1.69–1.92(2H,m), 1.28–1.52(6H,m), 1.37(9H,s), 0.77(3H,t, J=7.3 Hz).

Mass: FAB(+) m/e 696 (M+Na)$^+$.

Example 51

Nα-{L-3-trans-[(S)-1-propylcarbamoyl-2-phenylethylcarbamoyl]oxirane-2-carbonyl-L-lysine-1-naphthylamide hydrochloride Following a process similar to the process of Example 2, 160 mg of the title compound were obtained from 225 mg (0.33 mmol) of the compound obtained in Example 50.

m.p.: 177°–181° C.

$^1$H-NMR (DMSO-$d_6$) δ: 8.11(1H,t,J=5.6 Hz), 8.00–8.07 (1H,m), 7.92–7.97(1H,m), 7.45–7.90(7H,m), 4.47–4.56(5H, m), 3.65(1H,d,J=1.7 Hz), 3.61(1H,d,J=1.7 Hz), 2.75–3.70 (6H,m), 1.35–1.96(8H,m), 0.78(3H,5,J=7.3 Hz).

Mass: FAB(+) m/e 574 (MH)$^+$.

IR (KBr, cm$^{-1}$): 700, 770, 805, 1545, 1650, 2940, 2965, 3060, 3290.

Example 52

Nα-{L-3-trans-[(R)-1-(2-phenylethylcarbamoyl)-2-phenylethylcarbamoyl]oxirane-2-carbonyl}-Nε-t-butoxycarbonyl-L-lysine-1-naphthylamide Following a process similar to the process of Example 1, 1.0 g (2.8 mmol) of the compound obtained in Preparation Example 42 and 850 mg (2.2 mmol) of the compound obtained in Preparation Example 48 were condensed to obtain 1.4 g of the title compound.

m.p.: 241°–242° C.

$^1$H-NMR (DMSO-d$_6$) δ: 10.09(1H,s), 8.74(2H,d,J=7.6 Hz), 8.65(1H,d,J=8.3 Hz), 8.15(1H,t,J=5.4 Hz), 8.00–8.05 (1H,m), 7.93–7.96(1H,m), 7.12–7.63(14H,m), 6.76–7.83 (1H,m), 4.61–4.70(1H,m), 4.43–4.52(1H,m), 3.66(1H,d,J=1.7 Hz), 3.64(1H,d,J=1.7 Hz), 3.19–3.44(2H,m), 2.86–3.03 (3H,m), 2.79(1H,dd,J=9.5,13.6 Hz), 2.68(2H,t,J=7.3 Hz), 1.70–1.93(2H,m), 1.27–1.53(13H,m).

Mass: FAB(−) m/e 734 (MH)−.

Example 53

Nα-{L-3-trans-[(R)-1-(2-phenylethylcarbamoyl)-2-phenylethylcarbamoyl]oxirane-2-carbonyl}-L-lysine-1-naphthylamide hydrochloride Following a process similar to the process of Example 2, 121 mg of the title compound were obtained from 300 mg (0.41 mmol) of the compound obtained in Example 52.

m.p.: 189°–193° C.

$^1$H-NMR (DMSO-d$_6$) δ: 10.18(1H,s), 8.80(1H,d,J=7.8 Hz), 8.69(1H,d,J=8.3 Hz), 8.22(1H,t,J=5.4 Hz), 7.85–8.06 (4H,m), 7.77–7.83(1H,m), 7.47–7.66(4H,m), 7.12–7.31 (10H,m), 4.61–4.72(1H,m), 4.42–4.53(1H,m), 3.67(1H,s), 3.66(1H,s), 3.19–3.42(2H,m), 2.93(1H,dd,J=4.9,13.9 Hz), 2.73–2.88(3H,m), 2.67(1H,t,J=7.1 Hz), 1.32–1.98(6H,m).

Mass: FAB(+) m/e 636 (MH)+.

IR (KBr, cm$^{-1}$): 700, 771, 895, 1540, 1649, 2876, 3060, 3290.

Example 54

Nα-{L-3-trans-[(S)-1-carbamoyl-2-phenylethylcarbamoyl]oxirane- 2-carbonyl) -Nε-t-butoxycarbonyl-L-lysine anilide Following a process similar to the process of Example 1, 354 mg (1.10 mmol) of the compound obtained in Preparation Example 50 and 298 mg (1.0 mmol) of the compound obtained in Preparation Example 6 were condensed to obtain 313 mg of the title compound.

m.p.: 192°–194.5° C.

$^1$H-NMR (DMSO-d$_6$) δ: 10.10(1H,s), 8.70(1H,d,J=7.8 Hz), 8.66(1H,d,J=8.5 Hz), 7.59(1H,d,J=7.6 Hz), 7.18–7.32 (7H,m), 7.11(1H,br.s), 7.05(1H,dd,J=7.4,7.4 Hz), 6.77(1H, br.t,J=5.4 Hz), 4.48(1H,dd,J=4.9,9.8 Hz), 4.42(1H,br.dd,J=8.0,13.6 Hz), 3.58(1H,d,J=2.0 Hz), 3.56(1H,d,J=1.7 Hz), 3.02 (1H,dd,J=4.6,13.9 Hz), 2.89(1H,br.dd,J=6.6,13.2 Hz), 2.79 (2H,dd,J=9.8,13.6 Hz), 1.36(9H,s), 1.15–1.46(4H,m).

Mass:

FAB(+) m/e 620 (M+K)+.

Example 55

Nα-{L-3-trans-[(S)-1-carbamoyl-2-phenylethylcarbamoyl]oxirane-2-carbonyl}-Nε-L-lysine anilide hydrochloride Following a process similar to the process of Example 2, 197 mg of the title compound were obtained from 220 mg (0.38 mmol) of the compound obtained in Example 54.

m.p.: 142°–145° C.

$^1$H-NMR (DMSO-d$_6$) δ: 10.18(1H,s), 8.77(1H,d,J=8.1 Hz), 8.67(1H,d,J=8.5 Hz), 7.70(2H,br.s), 7.62(1H,s), 7.61 (2H,d,J=7.6 Hz), 7.14(7H,m), 7.12(1H,br.s), 7.06(1H,dd,J=7.6,7.6 Hz), 4.43–4.51(2H,m), 3.60(1H,d,J=1.7 Hz), 3.57 (1H,d,J=1.7), 3.03(1H,dd,J=4.4,13.9 Hz), 2.72–2.85(3H,m), 1.60–1.81(2H,s), 1.47–1.60(2H,m), 1.25–1.47(2H,m).

Mass: FAB(+) m/e 482 (MH)+.

IR (KBr, cm$^{-1}$): 1203.4, 1445.5, 1533.1, 1669.2.

Example 56

Nα-{L-3-trans-[(S)-1-phenylcarbamoyl-2-phenylethylcarbamoyl]oxirane-2-carbonyl}-Nε-t-butoxycarbonyl-L-lysine-1-naphthylamide Following a process similar to the process of Example 1, 200 mg (0.52 mmol) of the compound obtained in Preparation Example 42 and 150 mg (0.42 mmol) of the compound obtained in Preparation Example 53 were condensed to obtain 215 mg of the title compound.

m.p.: 221°–223° C.

$^1$H-NMR (DMSO-d$_6$) δ: 10.23(1H,s), 10.11(1H,s), 8.97(1H,d,J=7.8 Hz), 8.77(1H, d,J=6.8 Hz), 7.89–8.08(2H,m), 7.75–7.83(1H,m), 7.43–7.67 (6H,m), 7.16–7.38(7H,m), 7.00–7.09(1H,m), 6.75–6,83(1H, m), 4.55–4.80(2H,m), 3.66(1H,s), 3.63(1H,s), 3.08(1H,dd, J=9.8,13.6 Hz), 2.81–3.02(3H,m), 1.67–1.93(2H,m), 1.25–1.53(13H,m).

Mass: FAB(+) m/e 730 (M+Na)+.

Example 57

Nα-{L-3-trans-[(S)-1-phenylcarbamoyl-2-phenylethylcarbamoyl]oxirane-2-carbonyl}-L-lysine-1-naphthylamide hydrochloride Following a process similar to the process of Example 2, 200 mg of the title compound were obtained from 200 mg (0.52 mmol) of the compound obtained in Example 56.

m.p.: 184°–186° C.

$^1$H-NMR (DMSO-d$_6$) δ: 10.27(1H,s), 10.16(1H,s), 8.98 (1H,d,J=8.3 Hz), 8.83(1H,d,J=7.8 Hz), 8.00–8.08(1H,m), 7.91–7.97(1H,m), 7.15–7.90(16H,m), 7.02–7.09(1H,m), 4.59–4.80(2H,m), 3.69(1H,d,J=1.7 Hz), 3.64(1H,d,J=1.7 Hz), 3.09(1H,dd,J=4.9,13.3 Hz), 2.91(1H,dd,J=9.8,13.4 Hz), 2.75–2.85(2H,m), 1.85–1.97(1H,m), 1.72–1.84(1H,m), 1.57–1.68(2H,m), 1.38–1.56(2H,m).

Mass: FAB(+) m/e 608 (MH)+.

IR (KBr, cm$^{-1}$): 697, 755, 794, 896, 1445, 1540, 1653, 30890, 3280.

Example 58

Nα-{L-3-trans-[(S)-1-propylcarbamoyl-2-phenylethylcarbamoyl]oxirane-2-carbonyl}-Nε-t-butoxycarbonyl-L-lysine anilide Following a process similar to the process of Example 1, 500 mg (1.15 mmol) of the compound obtained in Preparation Example 55 and 279 mg (1.15 mmol) of the compound obtained in Preparation Example 43 were condensed to obtain 609 mg of the title compound.

m.p.: 223°–225.5° C.

H-NMR (DMSO-d$_6$) δ: 10.10(1H,s), 8.93(1H,d,J=9.3 Hz), 8.71(1H,d,J=8.8 Hz), 8.09(1H,t,J=5.6 Hz), 7.58(2H,d, J=8.3 Hz), 7.17–7.31(7H,m), 7.04(1H,dd,J=7.3,7.3 Hz), 6.76(1H,br.t,J=5.4 Hz), 4.49(1H,dt,J=5.4,9.0 Hz), 4.40(1H, br.dd,J=8.6,13.4 Hz), 3.57(1H,d,J=1.7 Hz), 3.56(1H,d,J=1.7 Hz), 2.86–3.07(5H,m), 2.78(2H,dd,J=9.3,13.2 Hz), 1.56–1.75(2H,m), 1.34(9H,s), 1.17–1.44(6H,m), 0.77(3H,t, J=7.3 Hz).

Mass: FAB(+) m/e 662 (M+K)+.

Example 59

Nα-{L-3-trans-[(S)-1-propylcarbamoyl-2-phenylethylcarbamoyl]oxirane-2-carbonyl}-L-lysine anilide hydrochloride Following a process similar to the process of Example 2, 134 mg of the title compound were obtained from 150 mg (0.24 mmol) of the compound obtained in Example 58.

m.p.: 162°–164° C.

¹H-NMR (DMSO-d₆) δ: 10.17(1H,s), 8.76(1H,d,J=7.5 Hz), 8.73(1H,d,J=8.3 Hz), 7.70(2H,br.s), 7.59(2H,d,J=7.6 Hz), 7.17–7.32(7H,m), 7.05(1H,br.t,J=7.3 Hz), 4.42–4.52 (2H,m), 3.59(1H,d,J=1.7 Hz), 3.57(1H,d,J=1.7 Hz), 2.89–3.07(3H,m), 2.73–2.81(3H,m), 1.58–1.78(2H,m), 1.49–1.58(2H,m), 1.25–1.49(4H,m), 0.78(3H,t,J=7.6 Hz).

Mass: FAB(+) m/e 524 (MH)⁺.

IR (KBr, cm⁻¹): 698.1, 1136.6, 1203.4, 1445.8, 1544.5, 1647.9.

Example 60

Nα-{L-3-trans-[(S)-1-isopropylcarbamoyl-2-phenylethylcarbamoyl]oxirane-2-carbonyl}-Nε-t-butoxycarbonyl-L-lysine anilide Following a process similar to the process of Example 1, 500 mg (1.15 mmol) of the compound obtained in Preparation Example 56 and 237 mg (1.15 mmol) of the compound obtained in Preparation Example 56 were condensed to obtain 567 mg of the title compound.

m.p.: 215°–218° C.

¹H-NMR (DMSO-d₆) δ: 10.10(1H,s), 8.71(1H,d,J=4.6 Hz), 8.69(1H,d,J=5.8 Hz), 7.95(1H,d,J=7.8 Hz), 7.58(2H,d, J=8.3 Hz), 7.18–7.31(7H,m), 7.04(1H,dd,J=7.6,7.6 Hz), 6.76(1H,br.t,J=5.4 Hz), 4.48(1H,dt,J=5.6,8.8 Hz), 4.40(1H, br.dd,J=8.0,13.7 Hz), 3.74–3.82(1H,m), 3.58(1H,d,J=1.7 Hz), 3.56(1H,d,J=1.7 Hz), 2.86–2.93(3H,m), 2.78(2H,dd,J= 9.3,13.6 Hz), 1.56–1.74(2H,m), 1.34(9H,s), 1.16–1.45(4H, m), 1.03(3H,d,J=6.6 Hz).

Mass: FAB(+) m/e 662 (M+K)⁺.

Example 61

Nα-{L-3-trans-[(S)-1-isopropylcarbamoyl-2-phenylethylcarbamoyl]oxirane-2-carbonyl}-L-lysine anilide hydrochloride Following a process similar to the process of Example 2, 185 mg of the title compound were obtained from 200 mg (0.32 mmol) of the compound obtained in Example 60.

m.p.: 164°–169° C.

¹H-NMR (DMSO-d₆) δ: 10.19(1H,s), 8.78(1H,d,J=7.8 Hz), 8.71(1H,d,J=8.4 Hz), 7.75(2H,br.s), 7.57(2H,d,J=8.3 Hz), 7.18–7.33(7H,m), 7.06(1H,dd,J=7.6,7.6 Hz), 4.43–4.54 (2H,m), 3.75–3.84(1H,m), 3.61(1H,s), 3.59(1H,s), 2.99(2H, dd,J=5.4,13.4 Hz), 2.77–2.82(3H,m), 1.61–1.88(2H,m), 1.48–1.61(2H,m), 1.28–1.48(2H,m), 1.04(3H,d,J=6.6 Hz), 0.95(3H,d,J=6.6 Hz).

Mass: FAB(+) m/e 524 (MH)⁺.

IR (KBr, cm⁻¹): 699.2, 1182.8, 1203.4, 1446.1, 1541.6, 1652.2.

Example 62

Nα-{L-3-trans-[(S)-1-methylcarbamoyl-2-phenylethylcarbamoyl]oxirane-2-carbonyl) -Nε-t-butoxycarbonyl-L-lysine anilide Following a process similar to the process of Example 1, 1.0 g (2.30 mmol) of the compound obtained in Preparation Example 55 and 463 mg (2.30 mmol) of the compound obtained in Preparation Example 57 were condensed to obtain 1.06 g of the title compound.

m.p.: 220°–222° C.

¹H-NMR (DMSO-d₆) δ: 10.10(1H,s), 8.76(1H,d,J=8.3 Hz), 8.71(1H,d,J=7.8 Hz), 8.06(1H,q,J=4.6 Hz), 7.59(2H,d, J=7.6 Hz), 7.17–7.32(7H,m), 7.05(1H,t,J=7.6 Hz), 6.76(1H, t,J=5.6 Hz), 4.41–4.50(2H,m), 3.57(2H,dd,J=1.9,2.0 Hz), 2.96(1H,dd,J=4.9,13.6 Hz), 2.86(1H,dt,J=6.4,6.6 Hz), 2.78 (1H,dd,J=9.9,13.6 Hz), 2,57(3H,d,J=4.6 Hz), 1.57–1.76(2H, m), 1.35(9H,s), 1.20–1.46(4H,m).

Mass: FAB(+) m/e 634 (M+K)⁺.

Example 63

Nα-{L-3-trans-[(S)-1-methylcarbamoyl-2-phenylethylcarbamoyl]oxirane-2-carbonyl}-L-lysine anilide hydrochloride Following a process similar to the process of Example 2, 89 mg of the title compound were obtained from 100 mg (0.17 mmol) of the compound obtained in Example 62.

m.p.: 175°–178° C.

¹H-NMR (DMSO-d₆) δ: 10.14(1H,s), 8.77(1H,d,J=8.1 Hz), 8.75(1H,d,J=8.5 Hz), 8.07(1H,q,J=4.4 Hz), 7.59(2H,d, J=7.6 Hz), 7.18–7.34(7H,m), 7.07(1H,t,J=7.3 Hz), 4.43–4.50(2H,m), 3.58(2H,dd,J=1.7,2.0 Hz), 2.98(2H,dd,J= 4.8,13.2 Hz), 2.76–2.81(3H,m), 2.57(3H,d,J=4.4 Hz), 1.25–1.86(6H,m).

Mass: FAB(+) m/e 496 (MH)⁺.

IR (KBr, cm⁻¹): 705, 785, 1203, 1537, 1548, 1645, 1649.

Example 64

Nα-{L-3-trans-[(S)-1-dimethylcarbamoyl-2-phenylethylcarbamoyl]oxirane-2-carbonyl}-Nε-t-butoxycarbonyl-L-lysine anilide Following a process similar to the process of Example 1, 1.5 g (3.45 mmol) of the compound obtained in Preparation Example 55 and 788 mg (3.45 mmol) of the compound obtained in Preparation Example 58 were condensed to obtain 1.25 g of the title compound.

m.p.: 100°–102° C.

¹H-NMR (DMSO-d₆) δ: 10.10(1H,s), 8.93(1H,d,J=8.1 Hz), 8.72(1H,d,J=7.8 Hz), 7.58(1H,d,J=7.6 Hz), 7.19–7.31 (7H,m), 7.04(1H,t,J=7.4 Hz), 6.76(1H,t,J=5.6 Hz), 4.91(1H, dt,J=6.3,8.3 Hz), 4.40(1H,dt,J=5.4,8.0 Hz), 3.58(2H,s), 2.72–2.96(4H,m), 2.87(3H,s), 2.78(3H,s), 1.18–1.75(6H,m), 1.34(9H,s).

Mass: FAB(−) m/e 608 (M−H)⁻.

Example 65

Nα-{L-3-trans-[(S)-1-dimethylcarbamoyl-2-phenylethylcarbamoyl]oxirane-2-carbonyl}-L-lysine anilide hydrochloride Following a process similar to the process of Example 2, 70 mg of the title compound were obtained from 100 mg (0.16 mmol) of the compound obtained in Example 64.

m.p.: 123°–126° C.

¹H-NMR (DMSO-d₆) δ: 10.16(1H,s), 8.93(1H,d,J=8.3 Hz), 8.77(1H,d,J=7.8 Hz), 7.60(1H,d,J=8.8 Hz), 7.20–7.33 (7H,m), 7.07(1H,t,J=7.3 Hz), 4.92(1H,dt,J=6.3,8.3 Hz), 4.46 (1H,dt,J=5.1,8.6 Hz), 3.61(2H,s), 2.74–2.97(4H,m), 2.88 (3H,s), 2.79(3H,s), 1.22–1.84(6H,m).

Mass: FAB(+) m/e 510 (MH)⁺.

IR (KBr, cm⁻¹): 685, 750, 1220, 1315, 1540, 1653.

Example 66

Nα-{L-3-trans-[(S)-1-ethylcarbamoyl-2-phenylethylcarbamoyl]oxirane-2-carbonyl)-Nε-t-butoxycarbonyl-L-lysine anilide Following a process similar to the process of Example 1, 1.0 g (2.30 mmol) of the compound obtained in Preparation Example 55 and 252 mg (2.30 mmol) of the compound obtained in Preparation Example 59 were condensed to obtain 380 mg of the title compound.

m.p.: 220°–222° C.

$^1$H-NMR (DMSO-d$_6$) δ: 10.12(1H,s), 8.75(1H,d,J=9.3 Hz), 8.73(1H,d,J=8.0 Hz), 8.11(1H,t,J=5.5 Hz), 7.59(2H,d, J=8.5 Hz), 7.20–7.32(7H,m), 7.05(1H,t,J=7.2 Hz), 6.78(1H, m), 4.38–4.52(2H,m), 3.58(2H,d,J=4.4 Hz), 2.76–3.15(6H, m), 1.69–1.76(2H,m), 1.10–1.45(4H,m), 1.35(9H,s) 0.96 (3H,t,J=7.1 Hz).

Mass: FAB(+) m/e 632 (M+Na)$^+$.

Example 67

Nα-{L-3-trans-[(S)-1-ethylcarbamoyl-2-phenylethylcarbamoyl]oxirane-2-carbonyl)-L-lysine anilide hydrochloride Following a process similar to the process of Example 2, 88 mg of the title compound were obtained from 100 mg (0.16 mmol) of the compound obtained in Example 66.

m.p.: 160°–162° C.

$^1$H-NMR (DMSO-d$_6$) δ: 10.18(1H,s), 8.78(1H,d,J=8.3 Hz), 8.74(1H,d,J=8.3 Hz), 8.12(1H,t,J=5.2 Hz), 7.60(2H,d, J=8.0 Hz), 7.20–7.33(7H,m), 7.06(1H,t,J=8.3 Hz), 4.45–4.52(2H,m), 3.60(1H,s), 3.58(1H,s), 2.95–3.08(4H,m), 2.80(2H,m), 1.26–1.80(6H,m) 0.96(3H,t,J=7.2 Hz).

Mass: FAB(+) m/e 510 (MH)$^+$.

IR (KBr, cm$^{-1}$): 685, 750, 1220, 1315, 1540, 1653.

Example 68

Nα-{L-3-trans-[(S)-1-cyclohexylcarbamoyl-2-phenylethylcarbamoyl]oxirane-2-carbonyl}-Nε-t-butoxycarbonyl-L-lysine anilide Following a process similar to the process of Example 1, 400 mg (0.92 mmol) of the compound obtained in Preparation Example 55 and 260 mg (0.92 mmol) of the compound obtained in Preparation Example 60 were condensed to obtain 300 mg of the title compound.

m.p.: 243°–245° C.

$^1$H-NMR (DMSO-d$_6$) δ: 10.20(1H,s), 8.72(1H,d,J=7.6 Hz), 8.70(1H,d,J=8.8 Hz), 7.99(1H,d,J=7.1 Hz), 7.61(2H, m), 7.03–7.32(8H,m), 6.77(1H,m), 4.54(1H,m), 4.44(1H, m), 3.60(1H,s), 3.58(1H,s), 3.48(1H,m), 2.77–2.90(4H,m), 0.86–1.68(16H,m), 1.35(9H,s).

Mass: FAB(+) m/e 686 (M+Na)$^+$ FAB(+) m/e 702 (M+K)$^+$.

Example 69

Nα-{L-3-trans-[(S)-1-cyclohexylcarbamoyl-2-phenylethylcarbamoyl]oxirane-2-carbonyl}-L-lysine anilide hydrochloride Following a process similar to the process of Example 2, 89 mg of the title compound were obtained from 100 mg (0.15 mmol) of the compound obtained in Example 68.

m.p.: 177°–179° C.

$^1$H-NMR (DMSO-d$_6$) δ: 10.23(1H,s), 8.75(1H,d,J=7.8 Hz), 8.70(1H,d,J=8.6 Hz), 7.97(1H,d,J=7.8 Hz), 7.18–7.90 (9H,m), 7.06(1H,t,J=7.3 Hz), 4.40–4.60(2H,m), 3.62(1H,d, J=1.7 Hz), 3.59(1H,d,J=1.7 Hz), 3.36(1H,m), 2.76–2.91(4H, m), 0.95–1.90(16H,m).

Mass: FAB(+) m/e 586 (M+Na)$^+$.

IR (KBr, cm$^{-1}$): 710, 1204, 1548, 1650, 1657.

Test Example 1

Determination of inhibition rate against cathepsin L, B and H

One that extracted from a rat liver and completely purified in accordance with the method by Katsunuma, et al. [T. Towatari, N. Katsunuma, et al., (1978), J. Biochem., 84, 659–671] was used as cathepsin L, and as a substrate thereof, Z-Phe-Arg-MCA was used.

One that extracted from a rat liver and completely purified in accordance with the method by Katsunuma, et al. [T. Towatari, N. Katsunuma, et al., (1978), Biochem. Biophys. Res. Commun., 83, 513–520] was used as cathepsin B, and as a substrate thereof, Z-Arg-Arg-MCA was used.

A purified product was purchased from Sigma Co. and used as cathepsin H, and as a substrate thereof, Arg-MCA was used. Samples were prepared by dissolving each compound in a small amount of dimethyl sulfoxide and diluting the solution with an acetate buffer of pH 5.5 so as to give a predetermined concentration.

Each cathepsin was diluted with a diluent (0.1% Brij 35) to adjust its concentration to 0.3 U (0.1 U: a concentration at which 1.0 nmol of MCA is released per minute at 37° C.). To 500 μl of this solution, were added 250 μl of an activator/buffer (340 mM sodium acetate, 60 mM acetic acid, 4 mM disodium EDTA; pH 5.5). After the mixture was incubated for 1 minute at 30° C., the sample solution of the predetermined concentration and 20 ml of a substrate solution were added to conduct a reaction for 10 minutes. The reaction was stopped with 1 ml of a reaction terminator (100 mM sodium monochloroacetate, 30 ml sodium acetate, 70 ml acetic acid; pH 4.3) to determine the fluorescence intensity of aminomethylcoumarin isolated under fluorescence 460 nm in wavelength obtained by excitation at a wavelength of 370 nm using a fluorometer. IC$_{50}$ against cathepsin B was divided by IC$_{50}$ against cathepsin L to calculate a B/L value, and that value was used as an index to an inhibitory activity specific for cathepsin L. The results are shown in Table 1. Incidentally, the compound described in European Patent Publication No. 655447A1 was synthesized in accordance with Preparation Example 61 to determine its inhibitory concentrations against cathepsin B, L and H in the same manner as described above. The results thereof are also shown in Table 1.

TABLE 1

| Compound | IC$_{50}$ (M) | | | B/L |
| --- | --- | --- | --- | --- |
| | Cathepsin L | Cathepsin B | Cathepsin H | |
| Example 2 | 3.5 × 10$^{-8}$ | >10$^{-5}$ | >10$^{-5}$ | >285 |
| Example 6 | 9.6 × 10$^{-7}$ | — | — | — |
| Example 10 | 8.7 × 10$^{-7}$ | — | — | — |
| Example 12 | 4.0 × 10$^{-8}$ | >10$^{-5}$ | — | >250 |
| Example 14 | 1.5 × 10$^{-8}$ | >10$^{-5}$ | >10$^{-5}$ | >667 |
| Example 16 | 2.2 × 10$^{-7}$ | — | — | — |
| Example 24 | 3.0 × 10$^{-11}$ | 2.1 × 10$^{-6}$ | — | 70000 |
| Example 26 | 4.0 × 10$^{-10}$ | 3.0 × 10$^{-6}$ | 3.2 × 10$^{-6}$ | 7500 |
| Example 30 | 7.2 × 10$^{-8}$ | 6.8 × 10$^{-6}$ | 6.0 × 10$^{-6}$ | 94.4 |
| Example 31 | 7.0 × 10$^{-9}$ | — | — | — |
| Example 32 | 4.0 × 10$^{-11}$ | 7.0 × 10$^{-6}$ | 4.8 × 10$^{-6}$ | 17500 |
| Example 35 | 1.7 × 10$^{-9}$ | 1.1 × 10$^{-5}$ | – | 6470 |
| Example 37 | 6.4 × 10$^{-9}$ | 2.5 × 10$^{-5}$ | – | 3906 |
| Example 39 | 1.6 × 10$^{-9}$ | 1.2 × 10$^{-5}$ | – | 7500 |
| Example 43 | 3.0 × 10$^{-9}$ | 9.0 × 10$^{-5}$ | – | 30000 |
| Example 45 | 7.0 × 10$^{-8}$ | 4.0 × 10$^{-5}$ | – | 571 |
| Example 47 | 1.0 × 10$^{-10}$ | 1.5 × 10$^{-5}$ | – | 150000 |
| Example 48 | 4.4 × 10$^{10}$ | 3.1 × 10$^{-6}$ | – | 7045 |

TABLE 1-continued

| Compound | IC$_{50}$ (M) Cathepsin L | Cathepsin B | Cathepsin H | B/L |
|---|---|---|---|---|
| Example 49 | 1.7 × 10$^{-9}$ | 2.0 × 10$^{-6}$ | – | 1176 |
| Example 51 | <10$^{-10}$ | 8.5 × 10$^{-6}$ | – | >85000 |
| Example 53 | 9.0 × 10$^{-8}$ | 3.0 × 10$^{-5}$ | – | 333 |
| Example 55 | 1.8 × 10$^{-8}$ | 4.4 × 10$^{-5}$ | – | 2444 |
| Example 57 | 9.0 × 10$^{-9}$ | >10$^{-5}$ | – | >11111 |
| Example 59 | 2.7 × 10$^{-9}$ | >10$^{-5}$ | – | >3703 |
| Example 61 | 2.8 × 10$^{-9}$ | >10$^{-5}$ | – | >3571 |
| Example 63 | 5.2 × 10$^{-9}$ | >10$^{-5}$ | – | 1923 |
| Example 65 | 3.0 × 10$^{-8}$ | >10$^{-5}$ | – | >333 |
| Example 67 | 3.6 × 10$^{-8}$ | 6.8 × 10$^{-5}$ | – | 1570 |
| Example 69 | 8.5 × 10$^{-9}$ | >10$^{-5}$ | – | >1177 |
| Preparation Example 61 | 8.1 × 10$^{-10}$ | 2.3 × 10$^{-8}$ | – | 28.4 |

As apparent from Table 1, the invention compounds each have excellent inhibitory effect on cathepsin L, B and H, and their effects are particularly strong on cathepsin L.

Test Example 2

In vivo determination of inhibition rate against liver cathepsin L, B and H

Specimens were prepared by dissolving each compound in a small amount of dimethyl sulfoxide and diluting the solution with an acetate buffer so as to give a predetermined concentration. Using male rats 100–150 g in weight, each specimen was administered intraperitoneally to the rat in a dose of 0.3–1.0 mg/100 g of weight. The rat was sacrificed after 3 hours in which the concentration of the specimen within a lysosome became highest, and its concentrations within a serum and a cytoplasm became substantially zero. After a buffer was perfused into the liver to remove the blood, the liver was enucleated. The lysosome was destroyed by a fractional quantitative ultrasonication to dissolve a group of cathepsin out of the lysosome, and a supernatant was obtained by centrifugation. The fractional determination of cathepsin L, B and H in the supernatant was conducted in accordance with the Inubushi method [T. Inubushi, H. Kakegawa, Y. Kishino & N. Katsunuma, J. Biochem., 116, 282–284 (1994)].

INDUSTRIAL APPLICABILITY

The epoxysuccinamide derivatives according to the present invention have specifically inhibitory activity for cathepsin L and family enzymes thereof and hence are useful as agents for preventing and treating muscular dystrophy, muscular atrophy, myocardial infarction, apoplectic stroke, Alzheimer disease, disturbance of consciousness and dyskinesis upon head injury, multiple sclerosis, peripheral nerve neuropathy, cataract, inflammation, allergy, fulminant hepatitis, osteoporosis, (malignant) hypercalcemia, Paget disease, breast cancer, prostatic cancer, and prostatic hypertrophy, or agents for inhibiting cancerous proliferation and preventing metastasis and platelet aggregation inhibitors.

We claim:

1. An epoxysuccinamide derivative represented by general formula (1)

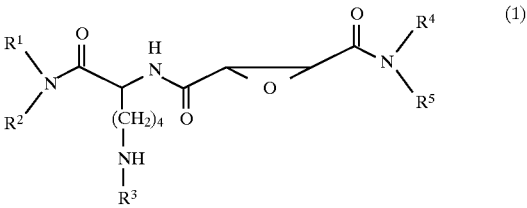

wherein R$^1$ and R$^2$ are the same or different from each other, and independently represent a hydrogen atom, a cyclic aromatic hydrocarbon group having 6–14 carbon atoms (which may have 1–3 substituents selected from an alkyl group having 1–6 carbon atoms, an alkoxy group having 1–6 carbon atoms, a halogen atom, a nitro group or a trifluoromethyl group), or an aralkyl group having 7–20 carbon atoms, or R$^1$ and R$^2$ represent, together with the adjacent nitrogen atom, an indolinyl group;

R$^3$ represents a hydrogen atom, an alkanoyl group having 1–7 carbon atoms, a benzoyl group, an alkoxycarbonyl group having 2–7 carbon atoms, or a benzyloxycarbonyl group;

R$^4$ represents a hydrogen atom or an aralkyl group having 7–20 carbon atoms; and R$^5$ represents a cyclic aromatic hydrocarbon group having 6–14 carbon atoms, or an aralkyl group having 7–20 carbon atoms, or R$^5$ represents, together with the adjacent nitrogen atom, an amino acid residue having 2–20 carbon atoms, the carboxyl group of which may be protected by an amino group, a C$_{1-6}$-alkylamino group, a di-C$_{1-6}$-alkylamino group, a C$_{3-6}$-cycloalkylamino group, an amino group substituted by an aromatic hydrocarbon group having 6–14 carbon atoms, or a C$_{7-20}$-aralkylamino group.

2. The epoxysuccinamide derivative or the salt thereof according to claim 1, wherein R$^1$ is a hydrogen atom, and R$^2$ is a phenyl or naphthyl group (which may have 1–3 substituents selected from an alkyl group having 1–6 carbon atoms, an alkoxy group having 1–6 carbon atoms, a halogen atom, a nitro group or a trifluoromethyl group).

3. The epoxysuccinamide derivative or the salt thereof according to any one of claims 1 to 2, wherein R$^4$ is a hydrogen atom, and R$^5$ is a phenyl, naphthyl or indanyl group, or an aralkyl group having 7–20 carbon atoms, or represents, together with the adjacent nitrogen atom, a phenylalanine residue, the carboxyl group of which may be protected by an amino group, a C$_{1-6}$-alkylamino group, a di-C$_{1-6}$-alkylamino group, a C$_{3-6}$-cycloalkylamino group, or a C$_{7-20}$-aralkylamino group.

4. A medicine comprising the epoxysuccinamide derivative or the salt thereof according to any one of claims 1 to 3 as an active ingredient.

5. The medicine according to claim 4, which is useful as an agent for preventing and treating osteopathy.

6. The medicine according to claim 4, which is useful as an agent for preventing and treating osteoporosis.

7. A medicinal composition comprising the epoxysuccinamide derivative or the salt thereof according to any one of claims 1 to 3 and a pharmaceutically acceptable carrier.

8. A method of treating osteopathy, which comprises administering an effective amount of the epoxysuccinamide derivative or the salt thereof according to any one of claims 1 to 3 to a patient.

9. The treating method according to claim 8, wherein the osteopathy is osteoporosis.

10. A process for preparing an epoxysuccinamide derivative represented by general formula (1)

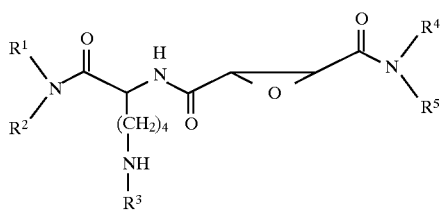 (1)

wherein $R^1$ and $R^2$ are the same or different from each other, and independently represent a hydrogen atom, a cyclic aromatic hydrocarbon group having 6–14 carbon atoms (which may have 1–3 substituents selected from an alkyl group having 1–6 carbon atoms, an alkoxy group having 1–6 carbon atoms, a halogen atom, a nitro group or a trifluoromethyl group), or aralkyl group having 7–20 carbon atoms, or $R^1$ and $R^2$ represent, together with the adjacent nitrogen atom, an indolinyl group;

- $R^3$ represents a hydrogen atom, an alkanoyl group having 1–7 carbon atoms, a benzoyl group, an alkoxycarbonyl group having 2–7 carbon atoms, or a benzyloxycarbonyl group;
- $R^4$ represents a hydrogen atom or an aralkyl group having 7–20 carbon atoms; and
- $R^5$ represents a cyclic aromatic hydrocarbon group having 6–14 carbon atoms, or aralkyl group having 7–20 carbon atoms, or $R^5$ represents, together with the adjacent nitrogen atom, an amino acid residue having 2–20 carbon atoms, the carboxyl group of which may be protected by an amino group, a $C_{1-6}$-alkylamino group, a di-$C_{1-6}$-alkylamino group, a $C_{3-6}$-cycloalkylamino group, an amino group substituted by an aromatic hydrocarbon group having 6–14 carbon atoms, or a $C_{7-20}$-aralkylamino group, or a salt thereof, which comprises reacting a carboxylic acid residue represented by the general formula (5)

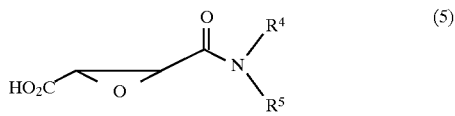 (5)

wherein $R^4$ and $R^5$ have the same meanings as defined above, and an amine represented by the general formula (6)

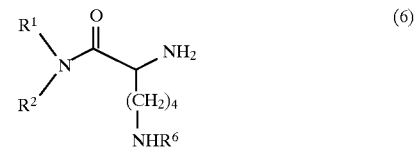 (6)

wherein $R^1$ and $R^2$ have the same meanings as defined above, and $R^6$ represents an acyl group, in the presence of a condensation agent, optionally separating the protecting group ($R^6$) for the amino group, and optionally reacting the amino group with an acylating agent.

* * * * *